(12) United States Patent
Shimamaki et al.

(10) Patent No.: US 8,324,331 B2
(45) Date of Patent: Dec. 4, 2012

(54) FLUORINE-CONTAINING COMPOUND AND POLYMERIC COMPOUND

(75) Inventors: Toshiharu Shimamaki, Hirakata (JP); Kenji Uenaga, Shijonawate (JP)

(73) Assignee: Daito Chemix Corporation, Osaka (JP)

( * ) Notice: Subject to any disclaimer, the term of this patent is extended or adjusted under 35 U.S.C. 154(b) by 331 days.

(21) Appl. No.: 12/639,677

(22) Filed: Dec. 16, 2009

(65) Prior Publication Data
US 2010/0168358 A1 Jul. 1, 2010

(51) Int. Cl.
*C08F 12/20* (2006.01)
*C07C 69/74* (2006.01)

(52) U.S. Cl. ........ 526/242; 560/122; 560/127; 560/128; 560/190; 560/192; 560/197

(58) Field of Classification Search .................. 526/242; 560/190
See application file for complete search history.

(56) References Cited

U.S. PATENT DOCUMENTS

| | | | |
|---|---|---|---|
| 5,945,517 A | 8/1999 | Nitta et al. | |
| 6,153,733 A | 11/2000 | Yukawa et al. | |
| 6,686,123 B2 * | 2/2004 | Lee et al. | 430/270.1 |
| 7,977,442 B2 * | 7/2011 | Maruyama et al. | 526/323.1 |
| 2009/0035699 A1 * | 2/2009 | Hasegawa et al. | 430/285.1 |

FOREIGN PATENT DOCUMENTS

| | | |
|---|---|---|
| JP | 09208554 A | 8/1997 |
| JP | 11-035551 | 2/1999 |
| JP | 11-035552 | 2/1999 |

(Continued)

OTHER PUBLICATIONS

D. Gil et al., "First Microprocessors with Immersion Lithography," Proceedings of SPIE (U.S.), vol. 5754 (2005), pp. 119-128.

(Continued)

*Primary Examiner* — Mark Eashoo
*Assistant Examiner* — Nicole M Buie-Hatcher
(74) *Attorney, Agent, or Firm* — Wood, Herron & Evans, LLP

(57) ABSTRACT

A compound represented by general formula (a-i) below, and a polymeric compound having a structural unit represented by general formula (a-ii) below (wherein R represents a hydrogen atom, a lower alkyl group or a halogenated lower alkyl group; X represents a divalent organic group represented by general formula (x-1) below; and $R^1$ represents an organic group having a fluorine atom).

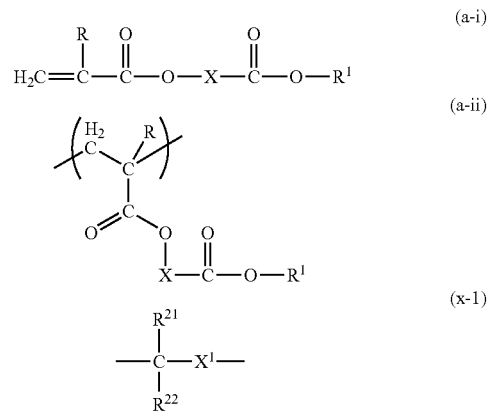

3 Claims, 1 Drawing Sheet

FOREIGN PATENT DOCUMENTS

| | | |
|---|---|---|
| JP | 11-035573 | 2/1999 |
| JP | 11-322707 | 11/1999 |
| WO | 2004/074242 | 9/2004 |
| WO | WO 2009110388 A1 * | 9/2009 |

OTHER PUBLICATIONS

Shun-Ichi Kodama et al., "Synthesis of Novel Fluoropolymer for 157 nm Photoresists by Cyclo-polymerization," Proceedings of SPIE (U.S.), vol. 4690 (2002), pp. 76-83.

* cited by examiner

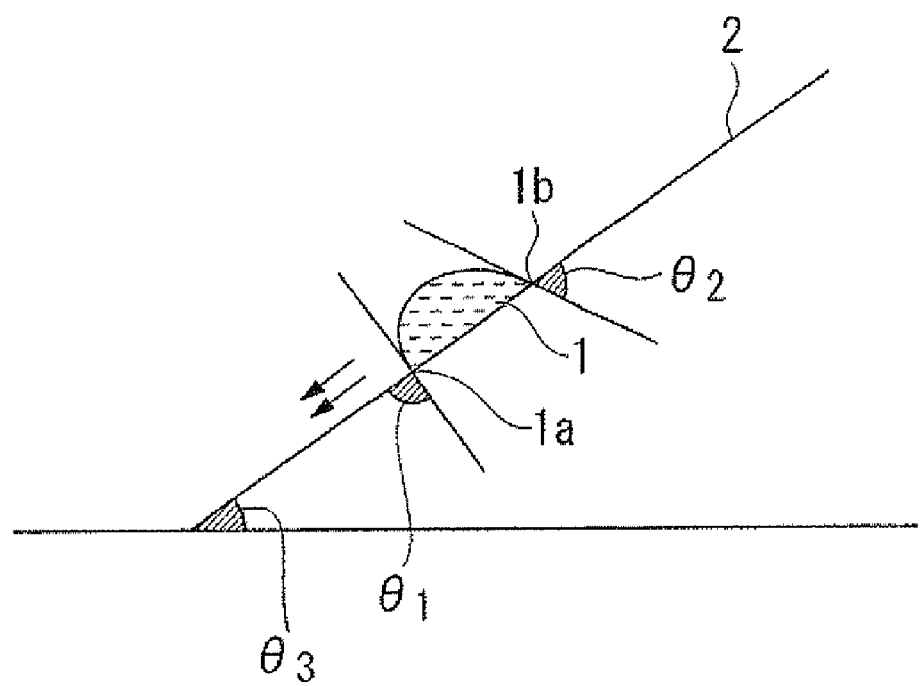

FLUORINE-CONTAINING COMPOUND AND POLYMERIC COMPOUND

TECHNICAL FIELD

The present invention relates to a novel fluorine-containing compound and a polymeric compound containing the fluorine-containing compound as a monomer unit, which is preferable as a component of a resist composition for immersion exposure (liquid immersion lithography).

BACKGROUND ART

In lithography techniques, for example, a resist film composed of a resist material is formed on a substrate, and the resist film is subjected to selective exposure of radial rays such as light or electron beam through a mask having a predetermined pattern, followed by development, thereby forming a resist pattern having a predetermined shape on the resist film.

For miniaturization of semiconductor devices, shortening of the wavelength of the exposure light source, and increasing of the numerical aperture (NA) of the projector lens have progressed. Currently, exposure apparatuses in which an ArF excimer laser having a wavelength of 193 nm is used as an exposure light source and NA=0.84 have been developed. As shortening the wavelength of the exposure light source progresses, it is required to improve various lithography properties of the resist material, such as the sensitivity to the exposure light source and a resolution capable of reproducing patterns of minute dimensions. As a resist material which satisfies these conditions, a chemically amplified resist is used, which includes a base resin that exhibits a changed solubility in an alkali developing solution under action of acid and an acid generator that generates acid upon exposure.

Currently, resins that contain structural units derived from (meth)acrylate esters within the main chain (acrylic resins) are now widely used as base resins for resists that use ArF excimer laser lithography, as they exhibit excellent transparency in the vicinity of 193 nm.

Here, the term "(meth)acrylic acid" is a generic term that includes either or both of acrylic acid having a hydrogen atom bonded to the α-position and methacrylic acid having a methyl group bonded to the α-position. The term "(meth)acrylate ester" is a generic term that includes either or both of the acrylate ester having a hydrogen atom bonded to the α-position and the methacrylate ester having a methyl group bonded to the α-position. The term "(meth)acrylate" is a generic term that includes either or both of the acrylate having a hydrogen atom bonded to the α-position and the methacrylate having a methyl group bonded to the α-position.

As a technique for further improving the resolution, a lithography method called liquid immersion lithography (hereafter, frequently referred to as "immersion exposure") is known in which exposure (immersion exposure) is conducted in a state where the region between the lens and the resist layer formed on a wafer is filled with a solvent (a immersion medium) that has a larger refractive index than the refractive index of air (see for example, Non-Patent Document 1).

According to this type of immersion exposure, it is considered that higher resolutions equivalent to those obtained using a shorter wavelength light source or a larger NA lens can be obtained using the same exposure light source wavelength, with no lowering of the depth of focus. Furthermore, immersion exposure can be conducted using a conventional exposure apparatus. As a result, it is expected that immersion exposure will enable the formation of resist patterns of higher resolution and superior depth of focus at lower costs. Accordingly, in the production of semiconductor devices, which requires enormous capital investment, immersion exposure is attracting considerable attention as a method that offers significant potential to the semiconductor industry, both in terms of cost and in terms of lithography properties such as resolution.

Immersion lithography is effective in forming patterns having various shapes. Further, immersion exposure is expected to be capable of being used in combination with currently studied super-resolution techniques, such as phase shift method and modified illumination method. Currently, as the immersion exposure technique, technique using an ArF excimer laser as an exposure source is being actively studied. Further, water is mainly used as the immersion medium.

In recent years, fluorine-containing compounds have been attracting attention for their properties such as water repellency and transparency, and active research and development of fluorine-containing compounds have been conducted in various fields. For example, in the fields of resist materials, currently, an acid-labile group such as a methoxymethyl group, tert-butyl group or tert-butoxycarbonyl group is being introduced into a fluorine-containing polymeric compound, and the fluorine-containing polymeric compound is used as a base resin for a chemically amplified positive resist. However, when such a fluorine-containing polymeric compound is used as a base resin for a positive resist, disadvantages are caused in that a large amount of an out gas is generated, and resistance to a dry-etching gas (etching resistance) is unsatisfactory.

Recently, as a fluorine-containing polymeric compound exhibiting excellent etching resistance, a fluorine-containing polymeric compound having an acid-labile group containing a cyclic hydrocarbon group has been reported (see, for example, Non-Patent Document 2).

DOCUMENTS OF RELATED ART

Non-Patent Documents

[Non-Patent Document 1] Proceedings of SPIE (U.S.), vol. 5754, pp. 119-128 (2005)
[Non-Patent Document 2] Proceedings of SPIE (U.S.), vol. 4690, pp. 76-83 (2002)

SUMMARY OF THE INVENTION

In immersion exposure, a resist material is required which exhibits not only general lithography properties (e.g., sensitivity, resolution, etching resistance and the like), but also properties suited for immersion lithography. For example, in immersion exposure, when the resist film comes in contact with the immersion medium, elution of a substance contained in the resist film into the immersion medium occurs. This elution of a substance causes phenomenon such as degeneration of the resist film and change in the refractive index of the immersion medium, thereby adversely affecting the lithography properties. The amount of the eluted substance is affected by the properties of the resist film surface (e.g., hydrophilicity, hydrophobicity and the like). For example, by enhancing the hydrophobicity of the resist film surface, the elution of a substance can be reduced. Further, when the immersion medium is water, and immersion exposure is performed using a scanning-type immersion exposure apparatus as disclosed in Non-Patent Document 1, a water tracking ability in which the immersion medium is capable of tracking the movement of the lens is required. When the water tracking ability is low, the exposure speed becomes low, and as a result, there is a possibility that the productivity is adversely affected. It is presumed that the water tracking ability can be improved by enhancing the hydrophobicity of the resist film (rendering the resist film hydrophobic).

Accordingly, it is presumed that the above-described characteristic problems of immersion lithography, which require a reduction in substance elution and an improvement in the water tracking ability, can be addressed by enhancing the hydrophobicity of the resist film surface. However, if the resist film is simply rendered hydrophobic, then adverse effects are seen on the lithography properties.

Therefore, in immersion lithography, development of a material which exhibits a satisfactory hydrophobicity and also exhibits both general lithography properties and properties required for immersion lithography becomes an important task. However, such a material has been essentially unknown in the art.

The present invention takes the above circumstances into consideration, with an object of providing a novel fluorine-containing compound and a polymeric compound containing the fluorine-containing compound as a monomer unit, which is preferable as a component of a resist composition for immersion exposure.

For solving the above-mentioned problems, the present inventors propose the following aspects.

Specifically, a first aspect of the present invention is a compound represented by general formula (a-i) shown below (hereafter, referred to as "fluorine-containing compound (A1)").

[Chemical Formula 1]

$$H_2C=\underset{R}{\overset{}{C}}-\underset{O}{\overset{O}{\underset{\parallel}{C}}}-O-X-\underset{}{\overset{O}{\underset{\parallel}{C}}}-O-R^1 \quad (a\text{-}i)$$

In formula (a-i), R represents a hydrogen atom, a lower alkyl group or a halogenated lower alkyl group; X represents a divalent organic group represented by general formula (x-1) shown below; and $R^1$ represents an organic group having a fluorine atom.

[Chemical Formula 2]

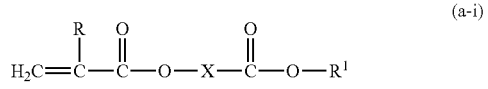

$$(x\text{-}1)$$

In formula (x-1), each of $R^{21}$ and $R^{22}$ independently represents an alkyl group which may be mutually bonded to form a ring; and $X^1$ represents an alkylene group or a divalent aliphatic cyclic group.

Further, a second aspect of the present invention is a polymeric compound having a structural unit represented by general formula (a-ii) shown below (hereafter, referred to as "polymeric compound (A2)").

[Chemical Formula 3]

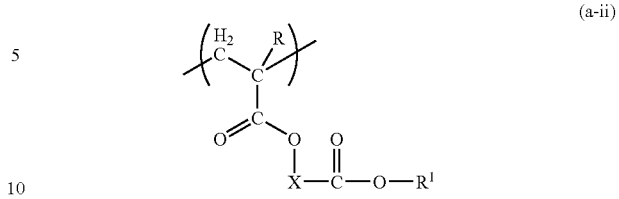

In formula (a-ii), R represents a hydrogen atom, a lower alkyl group or a halogenated lower alkyl group; X represents a divalent organic group represented by general formula (x-1) above; and $R^1$ represents an organic group having a fluorine atom.

In the present description and claims, the term "structural unit" refers to a monomer unit that contributes to the formation of a resin component (polymer).

The term "exposure" is used as a general concept that includes irradiation with any form of radiation.

The term "acid dissociable group" refers to an organic group that is dissociable by the action of an acid.

An "aliphatic cyclic group" refers to a monocyclic group or polycyclic group that has no aromaticity.

The term "alkyl group" includes linear, branched or cyclic, monovalent saturated hydrocarbon, unless otherwise specified.

A "lower alkyl group" is an alkyl group of 1 to 5 carbon atoms.

According to the present invention, there are provided a novel fluorine-containing compound and a polymeric compound containing the fluorine-containing compound as a monomer unit, which is preferable as a component of a resist composition for immersion exposure.

BRIEF DESCRIPTION OF THE DRAWINGS

FIG. 1 is an explanatory diagram of an advancing angle ($\theta_1$), a receding angle ($\theta_2$) and a sliding angle ($\theta_3$).

DETAILED DESCRIPTION OF THE INVENTION

[Fluorine-Containing Compound (A1)]

The fluorine-containing compound (A1) of the present invention is represented by the aforementioned general formula (a-i).

In general formula (a-i), R represents a hydrogen atom, a lower alkyl group or a halogenated lower alkyl group.

Specific examples of lower alkyl groups for R include linear or branched alkyl groups such as a methyl group, an ethyl group, a propyl group, an isopropyl group, an n-butyl group, an isobutyl group, a tert-butyl group, a pentyl group, an isopentyl group and a neopentyl group.

Specific examples of halogenated lower alkyl groups for R include groups in which part or all of the hydrogen atoms of the aforementioned lower alkyl group have been substituted with halogen atoms. Examples of the halogen atom include a fluorine atom, a chlorine atom, a bromine atom and an iodine atom, and a fluorine atom is particularly desirable.

As R, a hydrogen atom, a lower alkyl group or a fluorinated lower alkyl group is preferable, a hydrogen atom or a methyl group is more preferable, and a methyl group is particularly desirable.

In general formula (a-i), $R^1$ represents an organic group having a fluorine atom.

An "organic group having a fluorine atom" refers to an organic group in which part or all of the hydrogen atoms have been substituted with a fluorine atom.

As a preferable example of $R^1$, a fluorinated hydrocarbon group which may or may not have a substituent can be given. Among fluorinated hydrocarbon groups, a fluorinated, saturated hydrocarbon group or a fluorinated, unsaturated hydrocarbon group is preferable, and a fluorinated, saturated hydrocarbon group is particularly desirable.

A fluorinated hydrocarbon group "has a substituent" means that part or all of the hydrogen atoms within the fluorinated hydrocarbon group has been substituted with a group or atom other than hydrogen. Examples of substituents for the fluorinated hydrocarbon group include an alkyl group, an alkoxy group, a halogenated lower alkyl group and a halogen atom other than fluorine. The alkyl group as a substituent is preferably a lower alkyl group, and is the same as defined for the lower alkyl group for R above. The alkoxy group as a substituent preferably has 1 to 5 carbon atoms. The halogenated lower alkyl group as a substituent is the same as defined above for the halogenated lower alkyl group represented by R. Examples of halogen atoms other than fluorine include a chlorine atom, a bromine atom and an iodine atom.

$R^1$ may be linear, branched or cyclic, preferably linear or branched, and most preferably linear.

Further, $R^1$ preferably has 1 to 20 carbon atoms, more preferably 1 to 15, still more preferably 1 to 10, and most preferably 1 to 5.

It is preferable that the percentage of the hydrogen atoms substituted with fluorine atoms within $R^1$ be 25% or more, more preferably 40% or more, and most preferably 50% or more, as the hydrophobicity of the resist film during immersion exposure is enhanced. Further, it is preferable that the number of fluorine atoms bonded to $R^1$ on a carbon atom remote from the carbon atom bonded to the terminal oxygen atom of the "—X—C(=O)—O—" group in general formula (a-i) is large.

$R^1$ may be a group that is dissociable by the action of a base, such that the ester bond "—C(=O)—O—" having $R^1$ bonded thereto in general formula (a-i), i.e., "—C(=O)—O—$R^1$" is decomposed (hydrolyzed) to generate a hydrophilic group "—C(=O)—OH". In such a case, the component (A) containing the fluorine-containing compound (A1) or the polymeric compound (A2) described later becomes decomposable in an alkali developing solution. The expression "decomposable in an alkali developing solution" means that the group is decomposable by the action of an alkali developing solution (preferably decomposable by action of a 2.38% by weight aqueous solution of tetramethylammonium hydroxide (TMAH) at 23° C.), and exhibits increased solubility in the alkali developing solution. The component (A) containing such $R^1$ is a compound that is hardly soluble in an alkali developing solution prior to decomposition, and when the component (A) is decomposed by action of the developing solution, a carboxy group which is a hydrophilic group is formed, thereby exhibiting increased solubility in the alkali developing solution.

By using a resist composition for immersion exposure containing such a component (A), a resist pattern can be formed which is hydrophobic prior to coming in contact with an alkali developing solution (e.g., during immersion exposure), and becomes hydrophilic during alkali developing.

By using such a resist composition for immersion exposure in which the hydrophilicity is enhanced during alkali developing, generation of defects during immersion exposure can be effectively suppressed. More specifically, in liquid immersion lithography, when immersion exposure of a resist film is conducted, the solubility of the exposed portions in an alkali developing solution changes. For example, in the case of a positive resist composition, the solubility of the exposed portions in an alkali developing solution is increased, whereas in the case of a negative resist composition, the solubility of the exposed portions in an alkali developing solution is decreased. By conducting alkali developing, the exposed portions are removed in the case of a positive resist, whereas the unexposed portions are removed in the case of a negative resist, thereby enabling formation of a resist pattern. Generally, after alkali developing, defects (water mark defects and the like) due to the influence of the immersion medium such as water are likely to be generated on the surface of the resist film at unexposed portions in the case of a positive resist and exposed portions in the case of a negative resist. However, when the hydrophilicity of the resist film is enhanced during alkali developing, generation of such defects can be suppressed.

In general formula (a-i), X represents a divalent organic group represented by general formula (x-1), and has an acid dissociable portion.

An "acid dissociable portion" refers to a portion within the organic group which is dissociated from the organic group by action of acid generated upon exposure. Specifically, for example, a portion which forms a cyclic or chain-like tertiary alkyl ester with a carboxy group can be mentioned.

In general formula (x-1), each of $R^{21}$ and $R^{22}$ independently represents an alkyl group which may be linear, branched or cyclic, and preferably linear or branched.

The linear or branched alkyl group is preferably a linear or branched alkyl group of 1 to 5 carbon atoms, more preferably a methyl group or an ethyl group, and most preferably an ethyl group.

The cyclic alkyl group preferably has 4 to 15 carbon atoms, more preferably 4 to 12, and most preferably 5 to 10. Examples of cyclic alkyl groups include groups in which one or more hydrogen atoms have been removed from a monocycloalkane or a polycycloalkane such as a bicycloalkane, tricycloalkane or tetracycloalkane. Examples of such groups include groups in which one or more hydrogen atoms have been removed from a monocycloalkane such as cyclopentane or cyclohexane; and groups in which one or more hydrogen atoms have been removed from a polycycloalkane such as adamantane, norbornane, isobornane, tricyclodecane or tetracyclododecane. Among these examples, a group in which one or more hydrogen atoms have been removed from adamantane is preferable.

In general formula (x-1), $R^{21}$ and $R^{22}$ may be mutually bonded to form a ring structure. As the cyclic group formed by $R^{21}$ and $R^{22}$, the same groups as those described above for the aforementioned "alkyl group" can be mentioned. The cyclic group is preferably a 4- to 10-membered ring, more preferably a 5- to 7-membered ring.

In general formula (x-1), $X^1$ represents an alkylene group or a divalent aliphatic cyclic group.

As an example of the alkylene group for $X^1$, a group in which one hydrogen atom has been removed from an alkyl group for $R^{21}$ and $R^{22}$ can be given. As the alkylene group, a linear or branched alkylene group is preferable, more preferably a linear or branched alkylene group of 1 to 10 carbon atoms, and most preferably a linear or branched alkylene group of 1 to 5 carbon atoms.

As an example of the divalent aliphatic cyclic group for $X^1$, a group in which one hydrogen atom has been removed from an "aliphatic cyclic group" described later in relation to the structural unit (a1) can be given.

Among these examples, as $X^1$, an alkylene group is preferable.

The fluorine-containing compound (A1) is preferably a compound having a portion that forms a cyclic or chain-like tertiary alkyl ester with the carbonyl group as the acid dissociable portion X, more preferably a compound having a portion that forms a chain-like tertiary alkyl ester with the carbonyl group as the acid dissociable portion X, and still more preferably a compound represented by general formula (a-i-2) shown below.

[Chemical Formula 4]

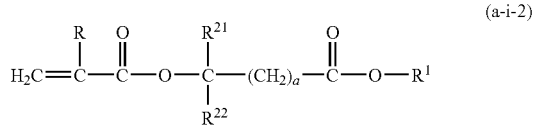

(a-i-2)

In the formula, R represents a hydrogen atom, a lower alkyl group or a halogenated lower alkyl group; $R^1$ represents an organic group having a fluorine atom; each of $R^{21}$ and $R^{22}$ independently represents an alkyl group which may be mutually bonded to form a ring; and a represents an integer of 1 to 10.

In general formula (a-i-2), R and $R^1$ are respectively the same as defined for R and $R^1$ in general formula (a-i). Further, $R^{21}$ and $R^{22}$ are respectively the same as defined for $R^{21}$ and $R^{22}$ in general formula (x-1).

In general formula (a-i-2), a represents an integer of 1 to 10, and preferably an integer of 1 to 5.

As the fluorine-containing compound (A1), one type of compound may be used alone, or two or more types of compounds may be used in combination.

The fluorine-containing compound (A1) per se can be preferably used as an additive in a resist composition for immersion exposure.

The fluorine-containing compound (A1) may be polymerized alone, or copolymerized with another polymerizable compound, so as to obtain a polymeric compound. Like the fluorine-containing compound (A1), such a polymeric compound can be preferably used as an additive in a resist composition for immersion exposure.

The fluorine-containing compound (A1) is useful as a monomer for producing the polymeric compound (A2) described below.

[Polymeric Compound (A2)]

The polymeric compound (A2) of the present invention is a polymeric compound having a structural unit derived from the aforementioned fluorine-containing compound (A1).

More specifically, the polymeric compound (A2) is a polymeric compound having a structural unit represented by general formula (a-ii) shown below (hereafter, this structural unit is referred to as "structural unit (a1)").

[Chemical Formula 5]

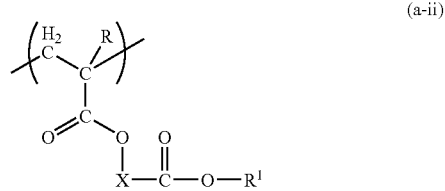

(a-ii)

In formula (a-ii), R represents a hydrogen atom, a lower alkyl group or a halogenated lower alkyl group; X represents a divalent organic group represented by general formula (x-1) shown below; and $R^1$ represents an organic group having a fluorine atom.

[Chemical Formula 6]

(x-1)

In formula (x-1), each of $R^{21}$ and $R^{22}$ independently represents an alkyl group which may be mutually bonded to form a ring; and $X^1$ represents an alkylene group or a divalent aliphatic cyclic group.

In general formula (a-ii), X, R and $R^1$ are respectively the same as defined for X, R and $R^1$ in general formula (a-i).

As a preferable example of the structural unit (a1), a structural unit represented by general formula (a-ii-1) shown below can be given.

[Chemical Formula 7]

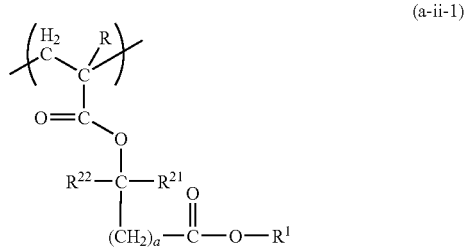

(a-ii-1)

In the formula, R represents a hydrogen atom, a lower alkyl group or a halogenated lower alkyl group; $R^1$ represents an organic group having a fluorine atom; each of $R^{21}$ and $R^{22}$ independently represents an alkyl group which may be mutually bonded to form a ring; and a represents an integer of 1 to 10.

In general formula (a-ii-1), R, $R^1$, $R^{21}$, $R^{22}$ and a are respectively the same as defined for R, $R^1$, $R^{21}$, $R^{22}$ and a in general formula (a-i-2).

Preferable examples of the structural unit represented by general formula (a-ii-1) are shown below.
[Chemical Formula 8]
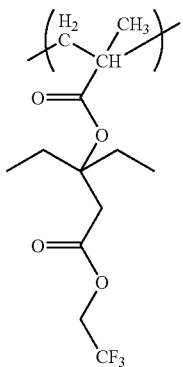
(c-1-20-1)
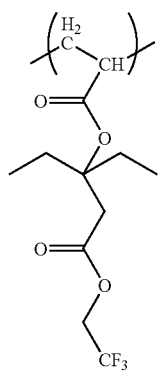
(c-1-20-2)
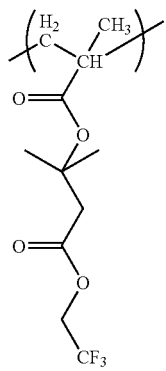
(c1-20-3)
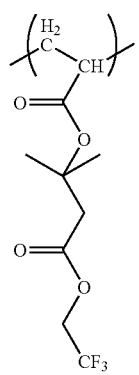
(c-1-20-4)
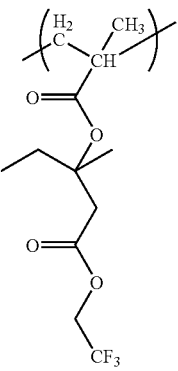
(c-1-20-5)
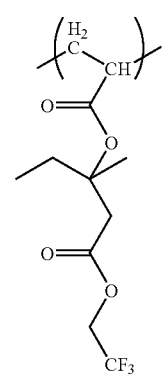
(c-1-20-6)
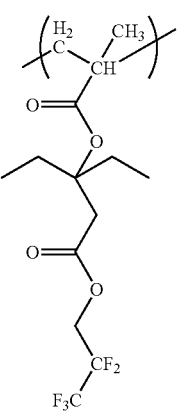
(c-1-20-7)
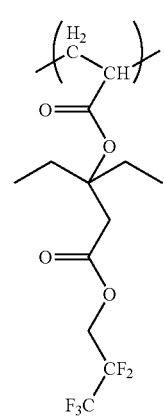
(c-1-20-8)

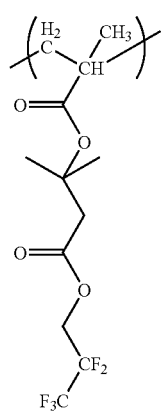
(c-1-20-9)
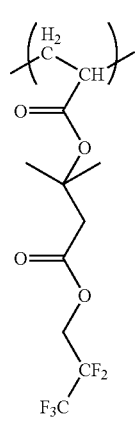
(c-1-20-10)
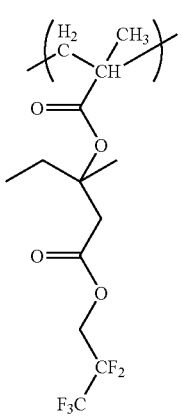
(c-1-20-11)
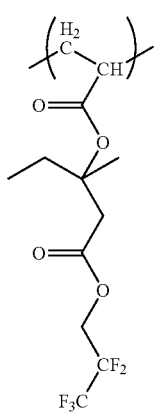
(c-1-20-12)
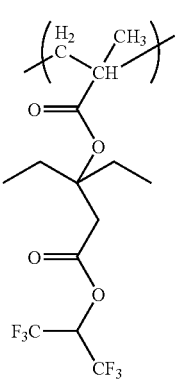
(c-1-20-13)
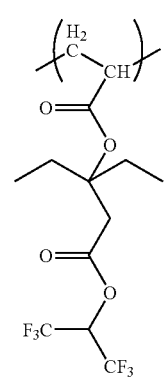
(c-1-20-14)
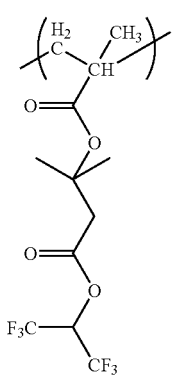
(c-1-20-15)
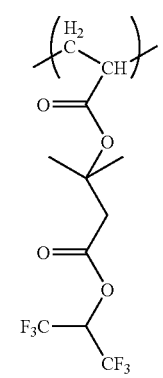
(c-1-20-16)

(c-1-20-17)
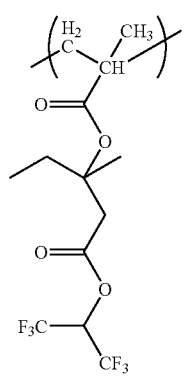
(c-1-20-18)
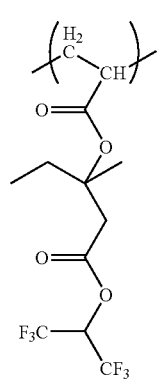
(c-1-20-19)
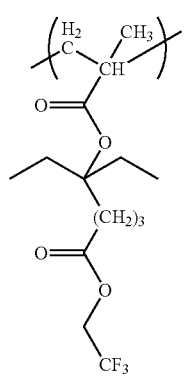
(c-1-20-20)
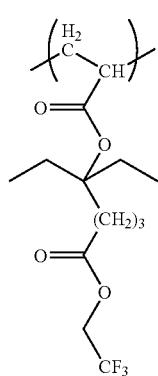
(c-1-20-21)
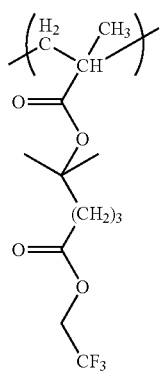
(c-1-20-22)
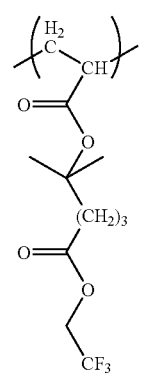
(c-1-20-23)
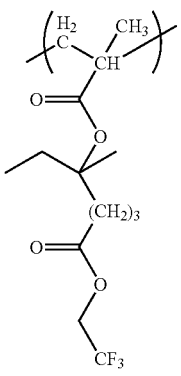
(c-1-20-24)
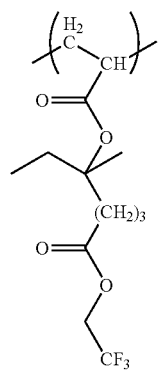

[Chemical Formula 9]
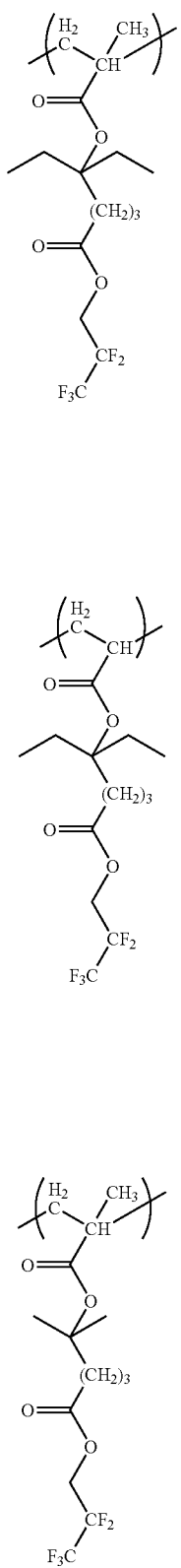
(c-1-20-25)
(c-1-20-26)
(c-1-20-27)
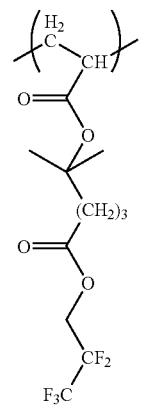
(c-1-20-28)
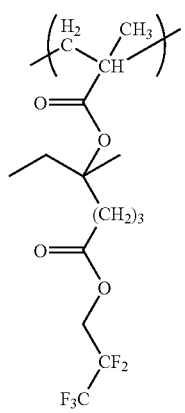
(c-1-20-29)
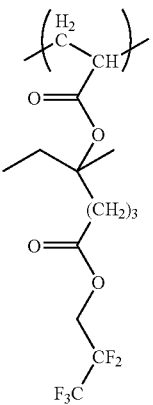
(c-1-20-30)
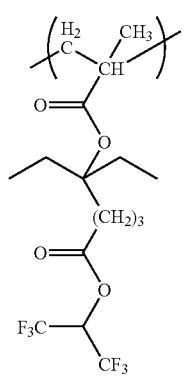
(c-1-20-31)

-continued
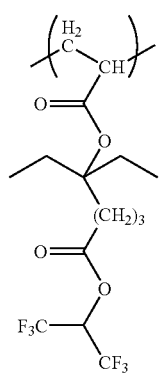
(c-1-20-32)
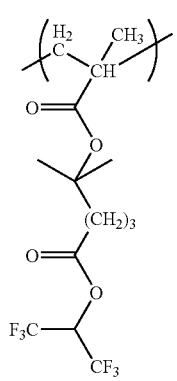
(c-1-20-33)
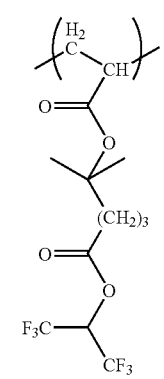
(c-1-20-34)
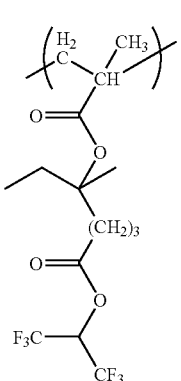
(c-1-20-35)
-continued
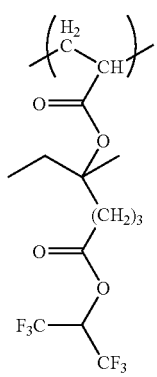
(c-1-20-36)
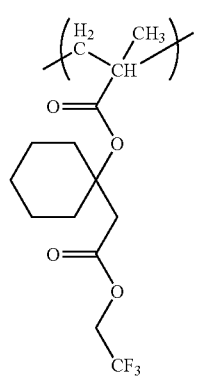
(c-1-20-37)
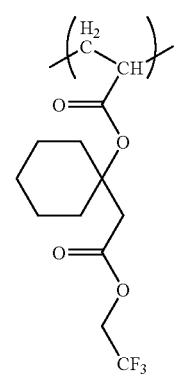
(c-1-20-38)
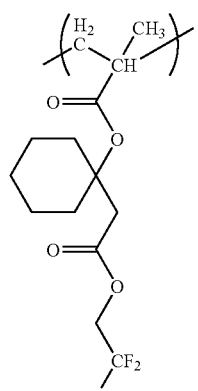
(c-1-20-39)

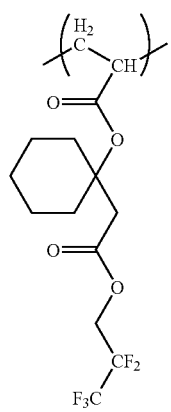 (c-1-20-40)
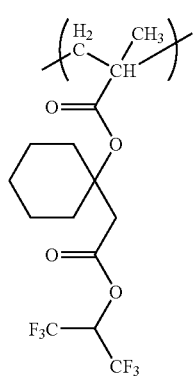 (c-1-20-41)
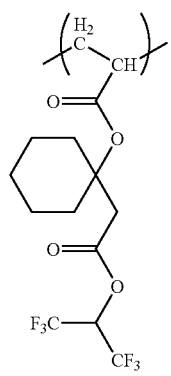 (c-1-20-42)
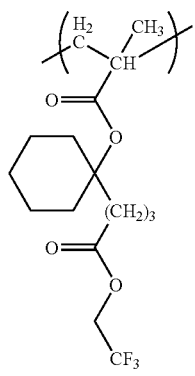 (c-1-20-43)
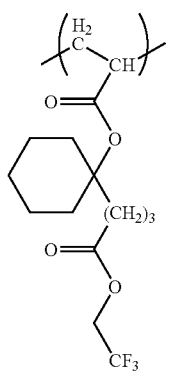 (c-1-20-44)
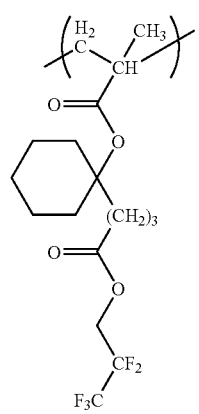 (c-1-20-45)
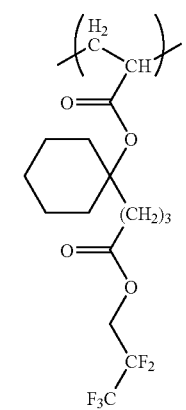 (c-1-20-46)
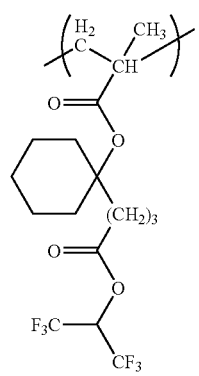 (c-1-20-47)

-continued
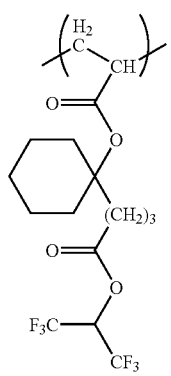
(c-1-20-48)
[Chemical Formula 10]
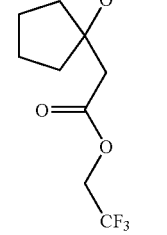
(c-1-20-49)
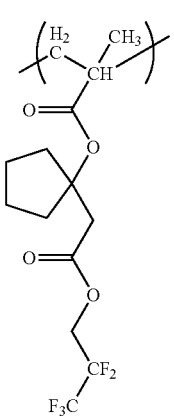
(c-1-20-50)
(c-1-20-51)
-continued
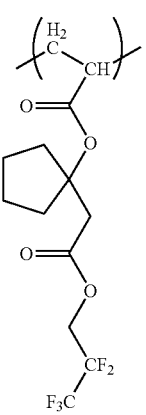
(c-1-20-52)
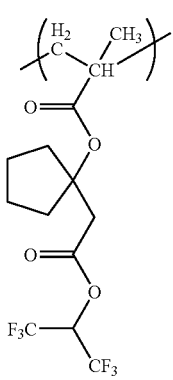
(c-1-20-53)
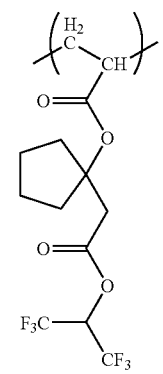
(c-1-20-54)
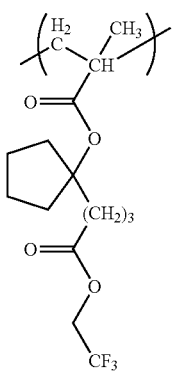
(c-1-20-55)

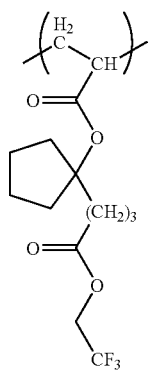
(c-1-20-56)
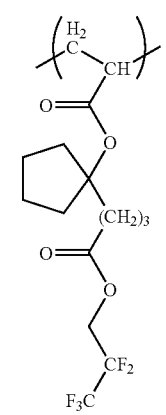
(c-1-20-57)
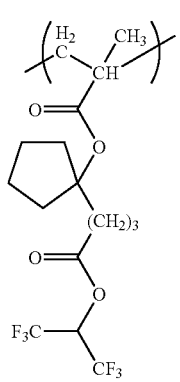
(c-1-20-58)
(c-1-20-59)
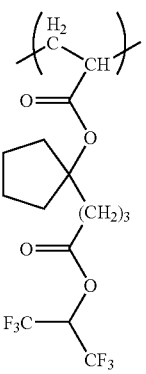
(c-1-20-60)
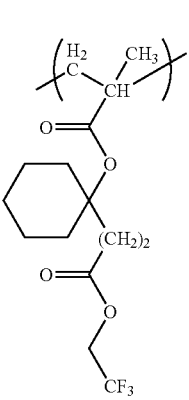
(c-1-20-61)
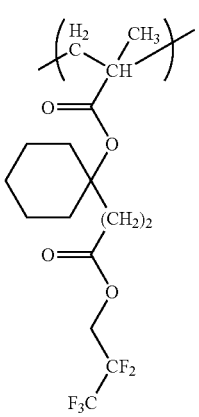
(c-1-20-62)
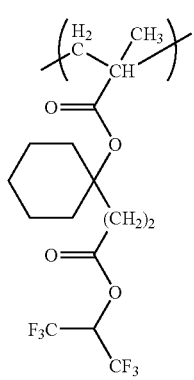
(c-1-20-63)

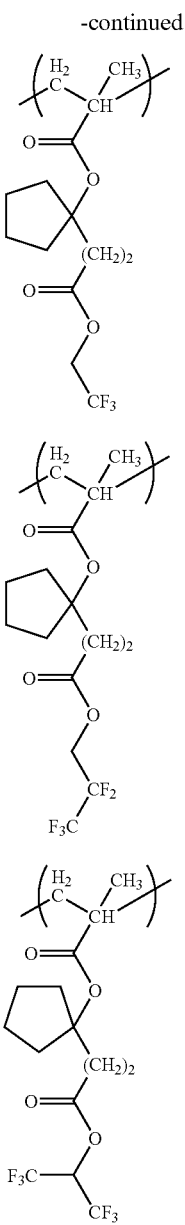

Among the structural units represented by formulas (c-1-20-1) to (c-1-20-66), structural units represented by formulas (c-1-20-1), (c-1-20-2), (c-1-20-7), (c-1-20-8), (c-1-20-13), (c-1-20-14), (c-1-20-19), (c-1-20-20), (c-1-20-25), (c-1-20-26), (c-1-20-31), (c-1-20-32) and (c-1-20-37) to (c-1-20-48) are preferable, and structural units represented by formulas (c-1-20-1), (c-1-20-2), (c-1-20-7), (c-1-20-8), (c-1-20-37) to (c-1-20-40) and (c-1-20-43) to (c-1-20-46) are particularly desirable.

In the polymeric compound (A2), as the structural unit (a1), one type of structural unit may be used alone, or two or more types of structural units may be used in combination.

In the polymeric compound (A2), the amount of the structural unit (a1) based on the combined total of all structural units constituting the polymeric compound (A2) is preferably 10 to 100 mol %, more preferably 30 to 100 mol %, still more preferably 40 to 100 mol %, and still more preferably 50 to 100 mol %. The amount of the structural unit (a1) may be even 100 mol %. When the amount of the structural unit (a1) is at least as large as the lower limit of the above-mentioned range, a high hydrophobicity can be achieved during formation of a resist pattern, and a resist film exhibiting excellent lithography properties can be obtained.

The polymeric compound (A2) may contain a structural unit other than the structural unit (a1), as long as the effects of the present invention are not impaired.

Such a structural unit is not particularly limited, and a structural unit derived from a compound copolymerizable with a compound from which the structural unit (a1) is derived can be preferably used. Examples of such structural units include the structural units (b1) to (b4) described later in relation to the resin component (B1) that exhibits increased solubility in an alkali developing solution under action of acid.

In the polymeric compound (A2), as the structural unit other than the structural unit (a1), one type of structural unit may be used alone, or two or more types of structural units may be used in combination.

The weight average molecular weight (Mw) (the polystyrene equivalent value determined by gel permeation chromatography) of the polymeric compound (A2) is not particularly limited, but is preferably 2,000 to 50,000, more preferably 3,000 to 30,000, and most preferably 4,000 to 25,000. When the weight average molecular weight is no more than the upper limit of the above-mentioned range, the resist composition exhibits a satisfactory solubility in a resist solvent. On the other hand, when the weight average molecular weight is at least as large as the lower limit of the above-mentioned range, dry etching resistance and the cross-sectional shape of the resist pattern becomes satisfactory.

Further, the dispersity (Mw/Mn) is preferably 1.0 to 5.0, more preferably 1.0 to 3.0, and most preferably 1.2 to 2.5. Here, Mn is the number average molecular weight.

As the polymeric compound (A2), one type of compound may be used alone, or two or more types of compounds may be used in combination.

The polymeric compound (A2) can be preferably used as an additive in a resist composition for immersion exposure.

As described above, the fluorine-containing compound (A1) or the polymeric compound (A2) according to the present invention can be preferably used as an additive (hereafter, referred to as "component (A)") for a resist composition for immersion exposure.

As the component (A), one type of fluorine-containing compound (A1) or polymeric compound (A2) may be used alone, or two or more types may be used in combination.

In the present invention, it is preferable to use the polymeric compound (A2) as the component (A). As the polymeric compound (A2), a polymeric compound having a structural unit represented by general formula (a-ii-1) is particularly desirable. Alternatively a combination of a fluorine-containing compound (A1) with a polymeric compound (A2) can be used as the component (A).

In a resist composition for immersion exposure containing the polymeric compound (A2) of the present invention, the amount of the component (A) relative to 100 parts by weight of the below-described resin component (B) that exhibits increased solubility in an alkali developing solution under action of acid is preferably 0.1 to 50 parts by weight, more preferably 0.1 to 40 parts by weight, still more preferably 0.3 to 30 parts by weight, and most preferably 0.5 to 15 parts by weight. When the amount of the component (A) is at least as large as the lower limit of the above-mentioned range, the hydrophobicity of a resist film formed using the resist composition for immersion exposure can be enhanced, so that the resist film exhibits hydrophobicity suitable for immersion exposure. On the other hand, when the amount of the component (A) is no more than the upper limit of the above-mentioned range, the lithography properties are improved.

<Production Method of Fluorine-Containing Compound (A1)>

In the production of the fluorine-containing compound (A1), for example, it is preferable to form the bond between the carbonyl group (—C(=O)—) within the carbonyloxy group (—C(=O)—O—) having $R^1$ bonded in general formula (a-i) and the oxygen atom (—O—) adjacent to the carbonyl group and bonded to the carbon atom. Further, it is preferable to react a group containing X with an α,β-unsaturated carbonyl compound or the like to form the structure "$H_2C=C(-R)-C(=O)-O-X-$".

More specifically, for example, a compound (a-i-2) which is preferable as the fluorine-containing compound (A1) can be produced as follows.

In a first step, a compound represented by general formula (a-i-01) shown below (hereafter, referred to as "compound (a-i-01)") is reacted with a compound represented by general formula (a-i-02) shown below (hereafter, referred to as "compound (a-i-02)") to obtain a compound represented by general formula (a-i-03) shown below (hereafter, referred to as "compound (a-i-03)").

Subsequently, in a second step, the compound (a-i-03) is reacted with a compound represented by general formula (a-i-04) shown below (hereafter, referred to as "compound (a-i-04)") to obtain a compound represented by general formula (a-i-05) shown below (hereafter, referred to as "compound (a-i-05)").

Thereafter, in a third step, the compound (a-i-05) is reacted with a compound represented by general formula (a-i-06) shown below (hereafter, referred to as "compound (a-i-06)") to thereby obtain a compound (a-i).

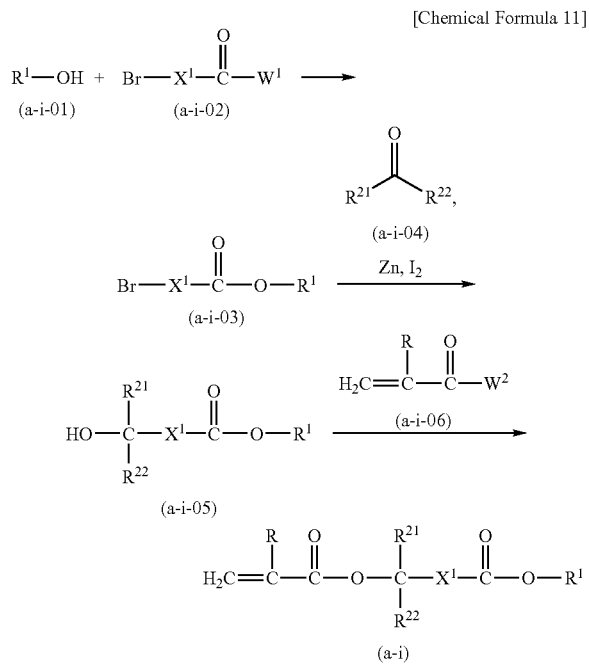

[Chemical Formula 11]

In the formula, R represents a hydrogen atom, a lower alkyl group or a halogenated lower alkyl group; and $R^1$ represents an organic group having a fluorine atom; each of $R^{21}$ and $R^{22}$ independently represents an alkyl group which may be mutually bonded to form a ring; $X^1$ represents an alkylene group or a divalent aliphatic cyclic group; and each of $W^1$ and $W^2$ independently represents a halogen atom.

In the formulas, R and $R^1$ are respectively the same as defined for R and $R^1$ in general formula (a-i), and $R^{21}$, $R^{22}$ and $X^1$ are respectively the same as defined for $R^{21}$, $R^{22}$ and $X^1$ in general formula (x-1).

In the formulas, each of $W^1$ and $W^2$ independently represents a halogen atom, preferably a chlorine atom or a bromine atom, and more preferably $W^1$ represents a bromine atom and $W^2$ represents a chlorine atom.

[First Step]

The first step is preferably performed, for example, by adding the compound (a-i-01) to a reaction solvent such as acetone, preferably in the presence of a base, more preferably in the presence of an organic base such as triethylamine, and adding the compound (a-i-02) thereto to effect a reaction. The compound (a-i-02) is preferably added in a dropwise manner, preferably over 1 to 5 hours, more preferably over 2 to 4 hours. The temperature during the addition of the compound (a-i-02) is preferably in the range of −5 to 15° C., more preferably −5 to 10° C. The reaction time following the addition of the compound (a-i-02) is preferably 0.5 to 7 hours, more preferably 1 to 4 hours. The reaction temperature is preferably −5 to 10° C., more preferably −5 to 5° C.

The amount of the compound (a-i-01) per 1 mole of the compound (a-i-02) is preferably 1 to 4 moles, more preferably 1.5 to 3 moles. The amount of the base per 1 mole of the compound (a-i-02) is preferably 1 to 5 moles, more preferably 2 to 3.5 moles.

Following the completion of the reaction, treatment such as extraction and washing may be conducted if desired. Then, the compound (a-i-03) may be separated and purified, or alternatively, the second step can be in situ performed without separation of the compound (a-i-03). The separation and purification can be conducted by a conventional method. For example, any one of concentration, solvent extraction, distillation, crystallization, re-crystallization and chromatography can be used alone, or two or more of these methods may be used in combination.

In the manner described above, the compound (a-i-03) can be obtained.

[Second Step]

The second step is preferably performed, for example, by adding the compound (a-i-04), a zinc powder, and iodine in a catalyst amount to a reaction solvent such as tetrahydrofuran (THF), and adding the compound (a-i-03) thereto to effect a reaction. The compound (a-i-03) is preferably added in a dropwise manner. The time for the dropwise addition is preferably 0.2 to 4 hours, and more preferably 0.3 to 2 hours. The temperature during the dropwise addition is preferably in the range of 30 to 70° C., more preferably 40 to 60° C. The reaction time following the addition of the compound (a-i-03) is preferably 0.5 to 7 hours, more preferably 1 to 4 hours. The reaction temperature is preferably the same as the temperature during the addition of the compound (a-i-03).

The amount of the compound (a-i-04) per 1 mole of the compound (a-i-03) is preferably 0.5 to 3 moles, more preferably 0.7 to 1.5 moles. The amount of the zinc powder per 1 mole of the compound (a-i-03) is preferably 0.7 to 3.5 moles, more preferably 1 to 2 moles.

The operation following the completion of the reaction can be conducted in the same manner as in the first step.

In the manner described above, the compound (a-i-05) can be obtained.

[Third Step]

In the third step, the compound (a-i-05) can be reacted with the compound (a-i-06) using the same reaction solvent as that used in the second step. The third step is preferably performed in situ following the second step without separation of the compound (a-i-05). In such a case, it is preferable to add a base, preferably an organic base such as triethylamine to the reaction solvent following the second step, and then add the compound (a-i-06). In the third step, the compound (a-i-06) is preferably added in a dropwise manner. The time for the dropwise addition is preferably over 0.2 to 4 hours, more preferably 0.3 to 2 hours. The temperature during the dropwise addition is preferably in the range of 10 to 40° C., more preferably 15 to 25° C. The reaction time following the addition of the compound (a-i-06) is preferably 0.5 to 7 hours, more preferably 1 to 4 hours. The reaction temperature is preferably the same as the temperature during the addition of the compound (a-i-06).

When the reaction is effected without separation of the compound (a-i-05), the amount of the compound (a-i-06) per 1 mole of the compound (a-i-03) is preferably 0.7 to 3 moles, more preferably 0.9 to 2 moles. The amount of the base may be the same as that of the compound (a-i-06).

After the completion of the reaction, various treatments, separation and purification can be conducted in the same manner as in the first step.

In the manner described above, the compound (a-i) can be obtained.

[Production Method of Polymeric Compound (A2)]

A polymeric compound (A2) can be produced, for example, by a conventional radical polymerization or the like of the monomers corresponding with each of the desired structural units (e.g., the aforementioned compound (a-i-2) and the like), using a radical polymerization initiator such as azobisisobutyronitrile (AIBN) or dimethyl 2,2'-azobis(butyrate).

<Resist Composition for Immersion Exposure>

The component (A) can be preferably used as a component of a resist composition for immersion exposure including a resin component (B) which exhibits increased solubility in an alkali developing solution under action of acid (hereafter, referred to as "component (B)") and an acid-generator component (C) which generates acid upon exposure (hereafter, referred to as "component (C)").

<Component (B)>

As the component (B), an organic compound typically used as a base component for a chemically amplified resist composition can be used alone, or two or more of such organic compounds can be mixed together.

Here, the term "base component" refers to an organic compound capable of forming a film, and is preferably an organic compound having a molecular weight of 500 or more. When the organic compound has a molecular weight of 500 or more, the film-forming ability is improved, and a resist pattern of nano level can be easily formed.

The organic compounds having a molecular weight of 500 or more that may be used as the base component are broadly classified into low molecular weight organic compounds having a molecular weight of 500 to less than 2,000 (namely, "low molecular weight materials") and high molecular weight organic compounds having a molecular weight of 2,000 or more (namely, "polymeric materials"). Generally, a non-polymer is used as the low molecular weight material. As a polymeric material, a resin (polymer or copolymer) is used, and the molecular weight of the resin is the polystyrene equivalent value determined by gel permeation chromatography (GPC). Hereafter, a "resin" refers to a resin having a molecular weight of 2,000 or more.

As the component (B), a resin which exhibits changed solubility in an alkali developing solution under action of acid may be used. Alternatively, as the component (B), a low molecular weight material which exhibits changed solubility in an alkali developing solution under action of acid may be used.

When the resist composition for immersion exposure containing the component (A) is a negative resist composition, for example, as the component (B), a base component that is soluble in an alkali developing solution is used, and a cross-linking agent is blended in the negative resist composition.

In the negative resist composition, when acid is generated from the component (C) upon exposure, the action of the generated acid causes cross-linking between the base component and the cross-linking agent, and the cross-linked portion becomes insoluble in an alkali developing solution. Therefore, in the formation of a resist pattern, by conducting selective exposure of a resist film formed by applying the negative resist composition onto a substrate, the exposed portions become insoluble in an alkali developing solution, whereas the unexposed portions remain soluble in an alkali developing solution, and hence, a resist pattern can be formed by alkali developing.

Generally, as the component (B) for a negative resist composition, a resin that is soluble in an alkali developing solution (hereafter, referred to as "alkali-soluble resin") is used.

As the alkali-soluble resin, it is preferable to use a resin having structural units derived from at least one of an α-(hydroxyalkyl)acrylic acid and a lower alkyl ester of an α-(hydroxyalkyl)acrylic acid, as such resins enable the formation of a satisfactory resist pattern with minimal swelling. Here, the term "α-(hydroxyalkyl)acrylic acid" refers to one or both of acrylic acid in which a hydrogen atom is bonded to the carbon atom on the α-position having the carboxyl group bonded thereto, and α-hydroxyalkylacrylic acid in which a hydroxyalkyl group (preferably a hydroxyalkyl group of 1 to 5 carbon atoms) is bonded to the carbon atom on the α-position.

As the cross-linking agent, typically, an amino-based cross-linking agent such as a glycoluril having a methylol group or alkoxymethyl group is preferable, as it enables formation of a resist pattern with minimal swelling. The amount of the cross-linker added is preferably within a range from 1 to 50 parts by weight, relative to 100 parts by weight of the alkali-soluble resin.

When the resist composition for immersion exposure containing the component (A) is a positive resist composition, as the component (B), a base component that exhibits increased solubility in an alkali developing solution under the action of acid is used. More specifically, the component (B) is substantially insoluble in an alkali developing solution prior to exposure, but when acid is generated from the component (C) upon exposure, the action of this acid causes an increase in the solubility of the base component in an alkali developing solution. Therefore, in the formation of a resist pattern, by conducting selective exposure of a resist film formed by applying the positive resist composition onto a substrate, the exposed portions changes from an insoluble state to a soluble state in an alkali developing solution, whereas the unexposed portions remain insoluble in an alkali developing solution, and hence, a resist pattern can be formed by alkali developing.

In the resist composition for immersion exposure, the component (B) is preferably a base component which exhibits increased solubility in an alkali developing solution under action of acid. That is, the resist composition for immersion exposure is preferably a positive resist composition.

The component (B) may be a resin component (B1) which exhibits increased solubility in an alkali developing solution under action of acid (hereafter, referred to as "component (B1)"), a low molecular weight material (B2) which exhibits increased solubility in an alkali developing solution under action of acid (hereafter, referred to as "component (B2)"), or a mixture of the component (B1) and the component (B2).

<Component (B1)>

As the component (B1), a resin component (base resin) typically used as a base component for a chemically amplified resist composition can be used alone, or two or more of such resin components can be mixed together, and a resin component containing a structural unit derived from an acrylate ester is preferable.

In the present description, the expression "structural unit derived from an acrylate ester" refers to a structural unit that is formed by the cleavage of the ethylenic double bond of an acrylate ester.

The term "acrylate ester" is a generic term that includes acrylate esters having a hydrogen atom bonded to the carbon atom on the α-position, and acrylate esters having a substituent (an atom other than a hydrogen atom or a group) bonded to the carbon atom on the α-position. As the substituent, a lower alkyl group or a halogenated lower alkyl group can be used.

With respect to the "structural unit derived from an acrylate ester", the "α-position (the carbon atom on the α-position)" refers to the carbon atom having the carbonyl group bonded thereto, unless specified otherwise.

With respect to the acrylate ester, specific examples of the lower alkyl group for the substituent at the α-position include linear or branched alkyl groups such as a methyl group, an ethyl group, a propyl group, an isopropyl group, an n-butyl group, an isobutyl group, a tert-butyl group, a pentyl group, an isopentyl group, and a neopentyl group.

Further, specific examples of the halogenated lower alkyl group include groups in which part or all of the hydrogen atoms of the aforementioned "lower alkyl group for the substituent at the α-position" have been substituted with halogen atoms. Examples of the halogen atom include a fluorine atom, a chlorine atom, a bromine atom and an iodine atom, and a fluorine atom is particularly desirable.

It is preferable that a hydrogen atom, a lower alkyl group or a halogenated lower alkyl group is bonded to the α-position of the acrylate ester, more preferably a hydrogen atom, a lower alkyl group or a fluorinated lower alkyl group. In terms of industrial availability, a hydrogen atom or a methyl group is particularly desirable.

It is particularly desirable that the component (B1) have a structural unit (b1) derived from an acrylate ester containing an acid dissociable, dissolution inhibiting group.

Further, it is preferable that the component (B1) have a structural unit (b2) derived from an acrylate ester containing a lactone-containing cyclic group, as well as the structural unit (b1).

Furthermore, it is preferable that the component (B1) have a structural unit (b3) derived from an acrylate ester containing a polar group-containing aliphatic hydrocarbon group, as well as the structural unit (b1), or the structural unit (b1) and the structural unit (b2).

Structural Unit (b1)

The structural unit (b1) is a structural unit derived from an acrylate ester containing an acid dissociable, dissolution inhibiting group.

As the acid dissociable, dissolution inhibiting group in the structural unit (b1), any of the groups that have been proposed as acid dissociable, dissolution inhibiting groups for the base resins of chemically amplified resists can be used, provided the group has an alkali dissolution-inhibiting effect that renders the entire component (B1) insoluble in an alkali developing solution prior to dissociation, and then following dissociation by action of acid, increases the solubility of the entire component (B1) in the alkali developing solution.

Generally, groups that form either a cyclic or chain-like tertiary alkyl ester with the carboxyl group of the (meth) acrylic acid, and acetal-type acid dissociable, dissolution inhibiting groups such as alkoxyalkyl groups are widely known. Here, the term "(meth)acrylate ester" is a generic term that includes either or both of the acrylate ester having a hydrogen atom bonded to the α-position and the methacrylate ester having a methyl group bonded to the α-position.

Here, a tertiary alkyl ester describes a structure in which an ester is formed by substituting the hydrogen atom of a carboxyl group with a chain-like or cyclic tertiary alkyl group, and a tertiary carbon atom within the chain-like or cyclic tertiary alkyl group is bonded to the oxygen atom at the terminal of the carbonyloxy group (—C(O)—O—). In this tertiary alkyl ester, the action of acid causes cleavage of the bond between the oxygen atom and the tertiary carbon atom.

The chain-like or cyclic alkyl group may have a substituent.

Hereafter, for the sake of simplicity, groups that exhibit acid dissociability as a result of the formation of a tertiary alkyl ester with a carboxyl group are referred to as "tertiary alkyl ester-type acid dissociable, dissolution inhibiting groups".

Examples of tertiary alkyl ester-type acid dissociable, dissolution inhibiting groups include aliphatic branched, acid dissociable, dissolution inhibiting groups and aliphatic cyclic group-containing acid dissociable, dissolution inhibiting groups.

In the present description and claims, the term "aliphatic" is a relative concept used in relation to the term "aromatic", and defines a group or compound that has no aromaticity.

The term "aliphatic branched" refers to a branched structure having no aromaticity.

The "aliphatic branched, acid dissociable, dissolution inhibiting group" is not limited to be constituted of only carbon atoms and hydrogen atoms (not limited to hydrocarbon groups), but is preferably a hydrocarbon group.

Further, the "hydrocarbon group" may be either saturated or unsaturated, but is preferably saturated.

Examples of aliphatic branched, acid dissociable, dissolution inhibiting groups include tertiary alkyl groups of 4 to 8 carbon atoms, and specific examples include a tert-butyl group, tert-pentyl group and tert-heptyl group.

The term "aliphatic cyclic group" refers to a monocyclic group or polycyclic group that has no aromaticity.

The "aliphatic cyclic group" within the structural unit (b1) may or may not have a substituent. Examples of substituents include lower alkyl groups of 1 to 5 carbon atoms, lower alkoxy groups of 1 to 5 carbon atoms, fluorine atom, fluorinated lower alkyl groups of 1 to 5 carbon atoms, and oxygen atom (=O).

The basic ring of the "aliphatic cyclic group" exclusive of substituents is not limited to be constituted from only carbon and hydrogen (not limited to hydrocarbon groups), but is preferably a hydrocarbon group. Further, the "hydrocarbon group" may be either saturated or unsaturated, but is preferably saturated. Furthermore, the "aliphatic cyclic group" is preferably a polycyclic group.

As such aliphatic cyclic groups, groups in which one or more hydrogen atoms have been removed from a monocycloalkane or a polycycloalkane such as a bicycloalkane, tricycloalkane or tetracycloalkane which may or may not be substituted with a lower alkyl group, a fluorine atom or a fluorinated alkyl group, may be used. Specific examples include groups in which one or more hydrogen atoms have been removed from a monocycloalkane such as cyclopentane and cyclohexane; and groups in which one or more hydrogen atoms have been removed from a polycycloalkane such as adamantane, norbornane, isobornane, tricyclodecane or tetracyclododecane.

As the aliphatic cyclic group-containing acid dissociable, dissolution inhibiting group, for example, a group which has a tertiary carbon atom on the ring structure of the cycloalkyl group can be used. Specific examples include 2-methyl-2-adamantyl group and a 2-ethyl-2-adamantyl group. Further, groups having an aliphatic cyclic group such as an adamantyl group, cyclohexyl group, cyclopentyl group, norbornyl group, tricyclodecyl group or tetracyclododecyl group, and a branched alkylene group having a tertiary carbon atom bonded thereto, as the groups bonded to the oxygen atom of the carbonyl group (—C(O)—O—) within the structural units represented by general formulas (b1"-1) to (b1"-6) shown below, can be used.

[Chemical Formula 12]

(b1"-1)

(b1"-2)

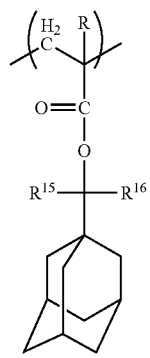

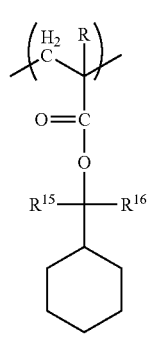

(b1"-3)

(b1"-4)

(b1"-5)

(b1"-6)

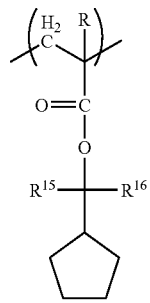

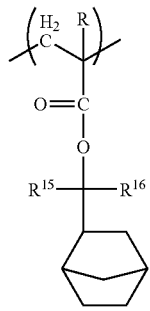

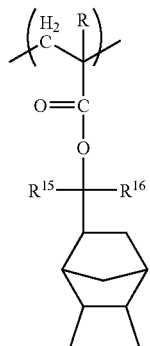

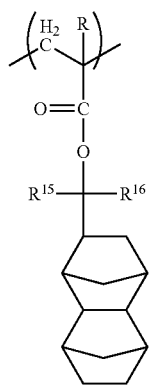

In the formulas, R represents a hydrogen atom, a lower alkyl group or a halogenated lower alkyl group; and $R^{15}$ and $R^{16}$ each independently represent an alkyl group (which may be linear or branched, and preferably has 1 to 5 carbon atoms).

In general formulas (b1"-1) to (b1"-6) above, the lower alkyl group or halogenated lower alkyl group for R are the same as the lower alkyl group or halogenated lower alkyl group which can be bonded to the α-position of the aforementioned acrylate ester.

An "acetal-type acid dissociable, dissolution inhibiting group" generally substitutes a hydrogen atom at the terminal of an alkali-soluble group such as a carboxy group or hydroxyl group, so as to be bonded with an oxygen atom. When acid is generated upon exposure, the generated acid acts to break the bond between the acetal-type acid dissociable, dissolution inhibiting group and the oxygen atom to which the acetal-type, acid dissociable, dissolution inhibiting group is bonded.

Examples of acetal-type acid dissociable, dissolution inhibiting groups include groups represented by general formula (p1) shown below.

[Chemical Formula 13]

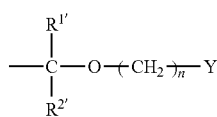

(p1)

In the formula, $R^{1'}$ and $R^{2'}$ each independently represent a hydrogen atom or a lower alkyl group; n represents an integer of 0 to 3; and Y represents a lower alkyl group or an aliphatic cyclic group.

In general formula (p1) above, n is preferably an integer of 0 to 2, more preferably 0 or 1, and most preferably 0.

As the lower alkyl group for $R^{1'}$ and $R^{2'}$, the same lower alkyl groups as those described above for R can be used, although a methyl group or ethyl group is preferable, and a methyl group is particularly desirable.

Further, it is preferable that at least one of $R^{1'}$ and $R^{2'}$ be a hydrogen atom. That is, it is preferable that the acid dissociable, dissolution inhibiting group (p1) is a group represented by general formula (p1-1) shown below.

[Chemical Formula 14]

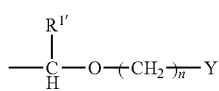

(p1-1)

In the formula, $R^{1'}$, n and Y are the same as defined above.

As the lower alkyl group for Y, the same as the lower alkyl groups for R above can be used.

As the aliphatic cyclic group for Y, any of the aliphatic monocyclic/polycyclic groups which have been proposed for conventional ArF resists and the like can be appropriately selected for use. For example, the same groups described above in connection with the "aliphatic cyclic group" can be used.

Further, as the acetal-type, acid dissociable, dissolution inhibiting group, groups represented by general formula (p2) shown below can also be used.

[Chemical Formula 15]

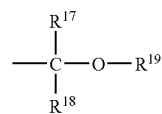

(p2)

In the formula, $R^{17}$ and $R^{18}$ each independently represent a linear or branched alkyl group or a hydrogen atom; and $R^{19}$ represents a linear, branched or cyclic alkyl group; or $R^{17}$ and $R^{19}$ each independently represents a linear or branched alkylene group, and the terminal of $R^{17}$ is bonded to the terminal of $R^{19}$ to form a ring.

The alkyl group for $R^{17}$ and $R^{18}$ preferably has 1 to 15 carbon atoms, and may be either linear or branched. As the alkyl group, an ethyl group or a methyl group is preferable, and a methyl group is most preferable. It is particularly desirable that either one of $R^{17}$ and $R^{18}$ is a hydrogen atom, and the other is a methyl group.

$R^{19}$ represents a linear, branched or cyclic alkyl group which preferably has 1 to 15 carbon atoms, and may be any of linear, branched or cyclic.

When $R^{19}$ represents a linear or branched alkyl group, it is preferably an alkyl group of 1 to 5 carbon atoms, more preferably an ethyl group or methyl group, and most preferably an ethyl group.

When $R^{19}$ represents a cycloalkyl group, it preferably has 4 to 15 carbon atoms, more preferably 4 to 12 carbon atoms, and most preferably 5 to 10 carbon atoms. As examples of the cycloalkyl group, groups in which one or more hydrogen atoms have been removed from a monocycloalkane or a polycycloalkane such as a bicycloalkane, tricycloalkane or tetracycloalkane, which may or may not be substituted with a fluorine atom or a fluorinated alkyl group, may be used. Examples of such groups include groups in which one or more hydrogen atoms have been removed from a monocycloalkane such as cyclopentane or cyclohexane; and groups in which one or more hydrogen atoms have been removed from a polycycloalkane such as adamantane, norbornane, isobornane, tricyclodecane or tetracyclododecane. Among these, a group in which one or more hydrogen atoms have been removed from adamantane is preferable.

In general formula (p2) above, $R^{17}$ and $R^{19}$ may each independently represent a linear or branched alkylene group (preferably an alkylene group of 1 to 5 carbon atoms), and the terminal of $R^{19}$ may be bonded to the terminal of $R^{17}$.

In such a case, a cyclic group is formed by $R^{17}$, $R^{19}$, the oxygen atom having $R^{19}$ bonded thereto, and the carbon atom having the oxygen atom and $R^{17}$ bonded thereto. Such a cyclic group is preferably a 4- to 7-membered ring, and more preferably a 4- to 6-membered ring. Specific examples of the cyclic group include tetrahydropyranyl group and tetrahydrofuranyl group.

As the structural unit (b1), it is preferable to use at least one member selected from the group consisting of structural units represented by formula (b1-0-1) shown below and structural units represented by formula (b1-0-2) shown below.

[Chemical Formula 16]

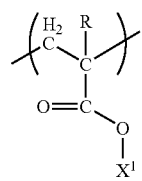

(b1-0-1)

In the formula, R represents a hydrogen atom, a lower alkyl group or a halogenated lower alkyl group; and $X^1$ represents an acid dissociable, dissolution inhibiting group.

[Chemical Formula 17]

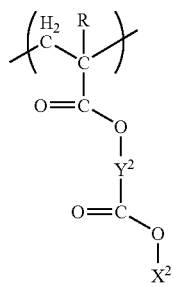

(b1-0-2)

In the formula, R represents a hydrogen atom, a lower alkyl group or a halogenated lower alkyl group; $X^2$ represents an acid dissociable, dissolution inhibiting group; and $Y^2$ represents a divalent linking group.

In general formula (b1-0-1) shown above, lower alkyl group and halogenated lower alkyl group for R are the same as the lower alkyl group and halogenated lower alkyl group which can be bonded to the α-position of the aforementioned acrylate ester.

$X^1$ is not particularly limited as long as it is an acid dissociable, dissolution inhibiting group. Examples thereof include the aforementioned tertiary alkyl ester-type acid dissociable, dissolution inhibiting groups and acetal-type acid dissociable, dissolution inhibiting groups, and tertiary alkyl ester-type acid dissociable, dissolution inhibiting groups are preferable.

In general formula (b1-0-2), R is the same as defined above.

$X^2$ is the same as defined for $X^1$ in general formula (b1-0-1).

As the divalent linking group for $Y^2$, an alkylene group, a divalent aliphatic cyclic group or a divalent linking group containing a hetero atom can be mentioned.

As the aliphatic cyclic group, the same as those used above in connection with the explanation of "aliphatic cyclic group" can be used, except that two hydrogen atoms have been removed therefrom.

When $Y^2$ represents an alkylene group, it preferably has 1 to 10 carbon atoms, more preferably 1 to 6, still more preferably 1 to 4, and most preferably 1 to 3.

When $Y^2$ represents a divalent aliphatic cyclic group, it is particularly desirable that the divalent aliphatic cyclic group be a group in which two or more hydrogen atoms have been removed from cyclopentane, cyclohexane, norbornane, isobornane, adamantane, tricyclodecane or tetracyclododecane.

When $Y^2$ represents a divalent linking group containing a hetero atom, examples thereof include —O—, —C(=O)—O—, —C(=O)—, —O—C(=O)—O—, —C(=O)—NH—, —NH— (H may be substituted with a substituent such as an alkyl group or an acyl group), —S—, —S(=O)$_2$—, —S(=O)$_2$—O—, and "-A-O—B— (wherein O is an oxygen atom, and each of A and B independently represents a divalent hydrocarbon group which may have a substituent)".

When $Y^2$ represents a divalent linking group —NH— and the H in the formula is replaced with a substituent such as an alkyl group or an acyl group, the substituent preferably has 1 to 10 carbon atoms, more preferably 1 to 8 carbon atoms, and most preferably 1 to 5 carbon atoms.

When $Y^2$ is "A-O—B", each of A and B independently represents a divalent hydrocarbon group which may have a substituent.

A hydrocarbon "has a substituent" means that part or all of the hydrogen atoms within the hydrocarbon group is substituted with groups or atoms other than hydrogen atom.

The hydrocarbon group for A may be either an aliphatic hydrocarbon group, or an aromatic hydrocarbon group. An "aliphatic hydrocarbon group" refers to a hydrocarbon group that has no aromaticity.

The aliphatic hydrocarbon group for A may be either saturated or unsaturated. In general, the aliphatic hydrocarbon group is preferably saturated.

As specific examples of the aliphatic hydrocarbon group for A, a linear or branched aliphatic hydrocarbon group, and an aliphatic hydrocarbon group having a ring in the structure thereof can be given.

The linear or branched aliphatic hydrocarbon group preferably has 1 to 10 carbon atoms, more preferably 1 to 8, still more preferably 2 to 5, and most preferably 2.

As a linear aliphatic hydrocarbon group, a linear alkylene group is preferable, and specific examples include a methylene group, an ethylene group [—$(CH_2)_2$—], a trimethylene group [—$(CH_2)_3$—], a tetramethylene group [—$(CH_2)_4$—] and a pentamethylene group [—$(CH_2)_5$—].

As the branched aliphatic hydrocarbon group, a branched alkylene group is preferable, and specific examples include alkylalkylene groups, e.g., alkylmethylene groups such as —CH($CH_3$)—, —CH($CH_2CH_3$)—, —C($CH_3$)$_2$—, —C($CH_3$)($CH_2CH_3$)—, —C($CH_3$)($CH_2CH_2CH_3$)— and —C($CH_2CH_3$)$_2$—; alkylethylene groups such as —CH($CH_3$)$CH_2$—, —CH($CH_3$)CH($CH_3$)—, —C($CH_3$)$_2$$CH_2$— and —CH($CH_2CH_3$)$CH_2$—; alkyltrimethylene groups such as —CH($CH_3$)$CH_2CH_2$— and —$CH_2$CH($CH_3$)$CH_2$—; and alkyltetramethylene groups such as —CH($CH_3$)$CH_2CH_2CH_2$— and —$CH_2$CH($CH_3$)$CH_2CH_2$—. As the alkyl group within the alkylalkylene group, a linear alkyl group of 1 to 5 carbon atoms is preferable.

The linear or branched aliphatic hydrocarbon group (chain-like aliphatic hydrocarbon group) may or may not have a substituent. Examples of the substituent include a fluorine atom, a fluorinated lower alkyl group of 1 to 5 carbon atoms, and an oxygen atom (=O).

As examples of the hydrocarbon group containing a ring, a cyclic aliphatic hydrocarbon group (a group in which two hydrogen atoms have been removed from an aliphatic hydrocarbon ring), and a group in which the cyclic aliphatic hydrocarbon group is bonded to the terminal of the aforementioned chain-like aliphatic hydrocarbon group or interposed within the aforementioned chain-like aliphatic hydrocarbon group, can be given.

The cyclic aliphatic hydrocarbon group preferably has 3 to 20 carbon atoms, and more preferably 3 to 12 carbon atoms.

The cyclic aliphatic hydrocarbon group may be either a polycyclic group or a monocyclic group. As the monocyclic group, a group in which two hydrogen atoms have been removed from a monocycloalkane of 3 to 6 carbon atoms is preferable. Examples of the monocycloalkane include cyclopentane and cyclohexane. As the polycyclic group, a group in which two hydrogen atoms have been removed from a polycycloalkane of 7 to 12 carbon atoms is preferable. Examples of the polycycloalkane include adamantane, norbornane, isobornane, tricyclodecane and tetracyclododecane.

The cyclic aliphatic hydrocarbon group may or may not have a substituent. Examples of the substituent include a lower alkyl group of 1 to 5 carbon atoms, a fluorine atom, a fluorinated lower alkyl group of 1 to 5 carbon atoms, and an oxygen atom (=O).

As A, a linear aliphatic hydrocarbon group is preferable, more preferably a linear alkylene group, still more preferably a linear alkylene group of 2 to 5 carbon atoms, and most preferably an ethylene group.

As the hydrocarbon group for B, the same divalent hydrocarbon groups as those described above for A can be used.

As B, a linear or branched aliphatic hydrocarbon group is preferable, and a methylene group or an alkylmethylene group is particularly desirable.

The alkyl group within the alkyl methylene group is preferably a linear alkyl group of 1 to 5 carbon atoms, more preferably a linear alkyl group of 1 to 3 carbon atoms, and most preferably a methyl group.

Specific examples of the structural unit (b1) include structural units represented by general formulas (b1-1) to (b1-4) shown below.

[Chemical Formula 18]

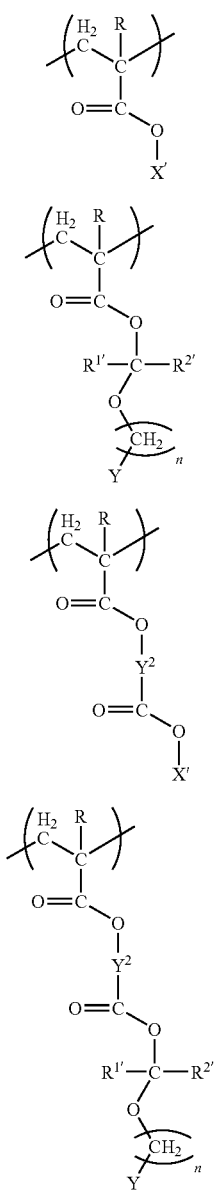

In the formulas, X' represents a tertiary alkyl ester-type acid dissociable, dissolution inhibiting group; Y represents a lower alkyl group of 1 to 5 carbon atoms or an aliphatic cyclic group; n represents an integer of 0 to 3; $Y^2$ represents an alkylene group, a divalent aliphatic cyclic group or "A-O—B" (wherein A and B are the same as defined above); R is the same as defined above; and each of $R^{1\prime}$ and $R^{2\prime}$ independently represents a hydrogen atom or a lower alkyl group of 1 to 5 carbon atoms.

Examples of the tertiary alkyl ester-type acid dissociable, dissolution inhibiting group for X' include the same tertiary alkyl ester-type acid dissociable, dissolution inhibiting groups as those described above for $X^1$.

As $R^{1\prime}$, $R^{2\prime}$, n and Y are respectively the same as defined for $R^{1\prime}$, $R^{2\prime}$, n and Y in general formula (p1) described above in connection with the "acetal-type acid dissociable, dissolution inhibiting group".

As examples of $Y^2$, the same groups as those described above for $Y^2$ in general formula (b1-0-2) can be given.

Specific examples of structural units represented by general formula (b1-1) to (b1-4) are shown below.

[Chemical Formula 19]

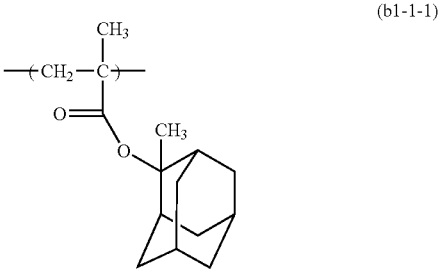

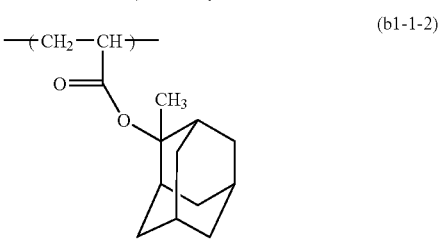

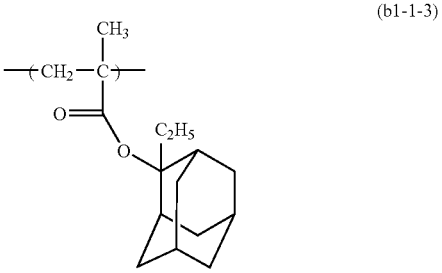

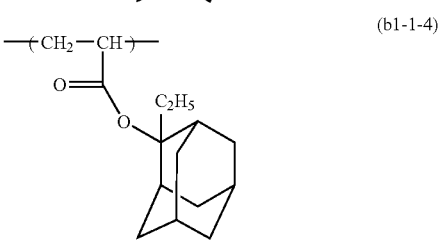

[Chemical Formula 20]

(b1-1-20) through (b1-1-33)

[Chemical Formula 21]
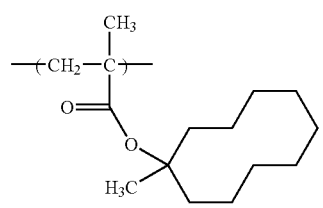 (b1-1-34)
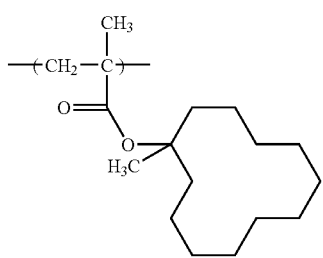 (b1-1-35)
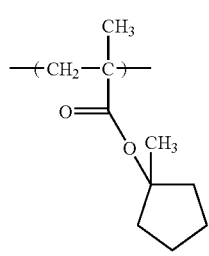 (b1-1-36)
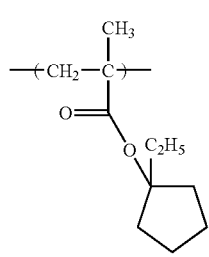 (b1-1-37)
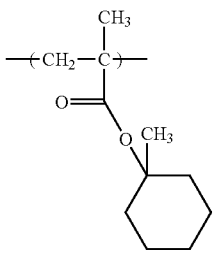 (b1-1-38)
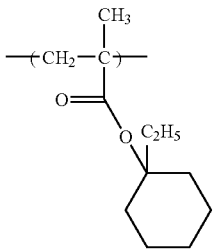 (b1-1-39)
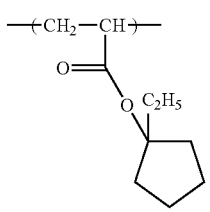 (b1-1-40)
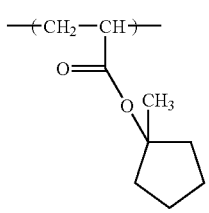 (b1-1-41)
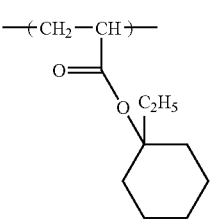 (b1-1-42)
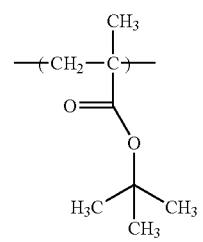 (b1-1-43)
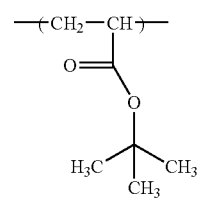 (b1-1-44)
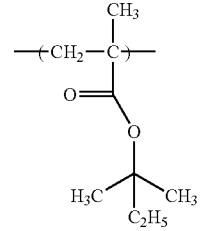 (b1-1-45)
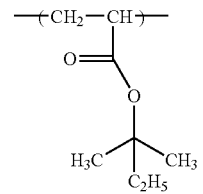 (b1-1-46)

(b1-1-47)
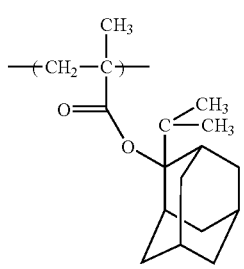
(b1-1-48)
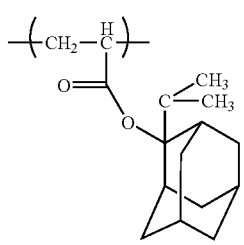
[Chemical Formula 22]
(b1-2-1)
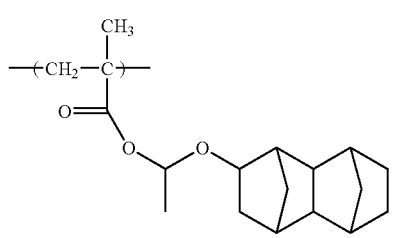
(b1-2-2)
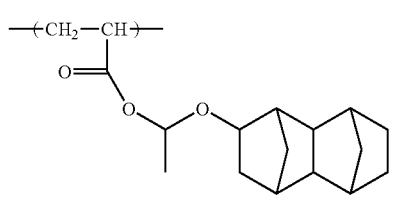
(b1-2-3)
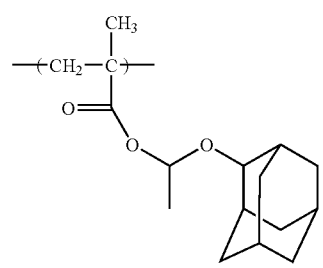
(b1-2-4)
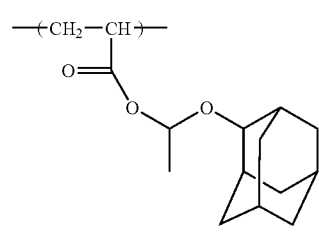
(b1-2-5)
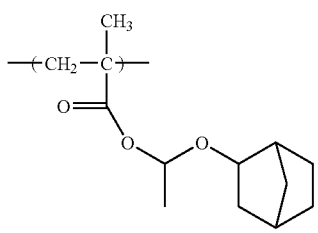
(b1-2-6)
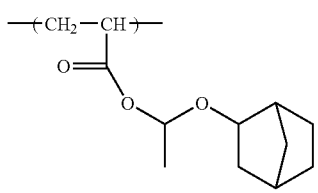
[Chemical Formula 23]
(b1-2-7)
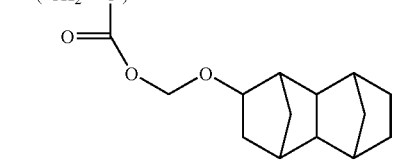
(b1-2-8)
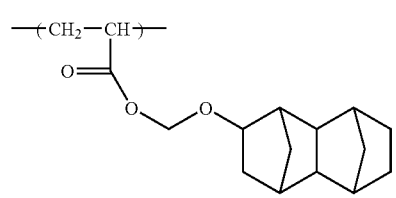
(b1-2-9)
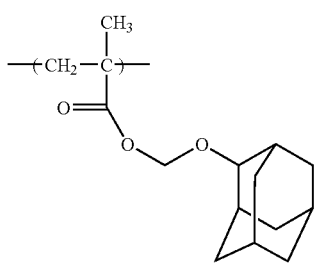
(b1-2-10)
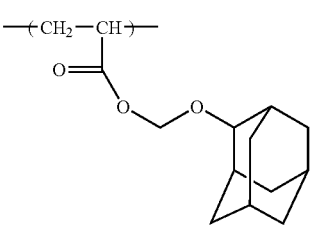
(b1-2-11)
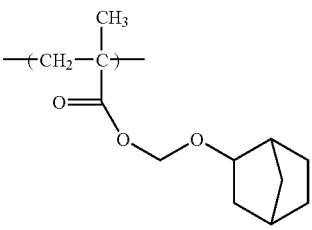

(b1-2-12) 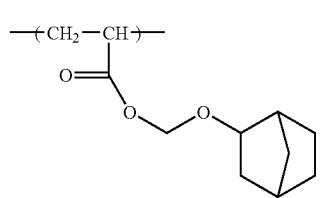
(b1-2-13) 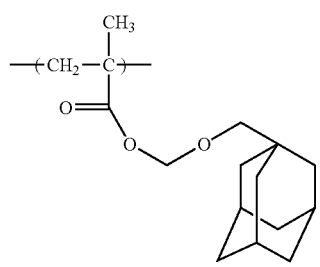
(b1-2-14) 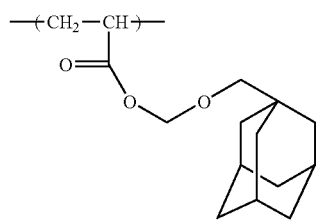
(b1-2-15) 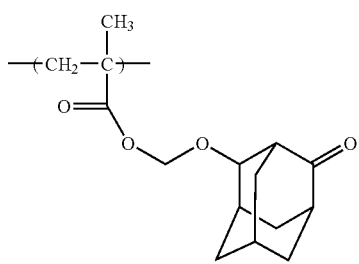
(b1-2-16) 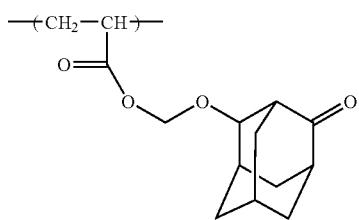
(b1-2-17) 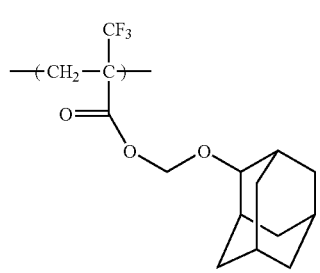
(b1-2-18) 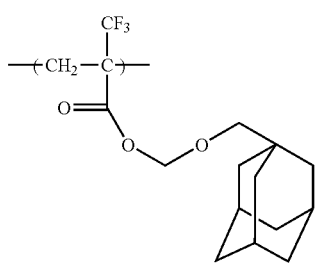
(b1-2-19) 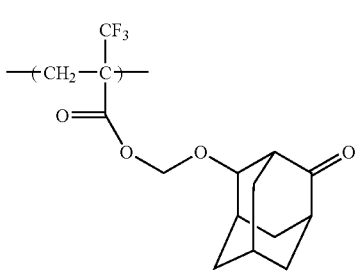
(b1-2-20) 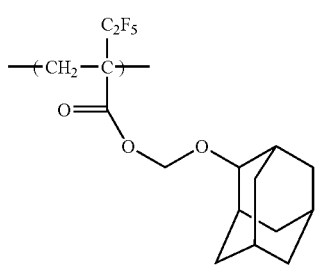
[Chemical Formula 24]
(b1-2-21) 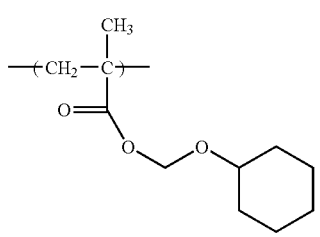
(b1-2-22) 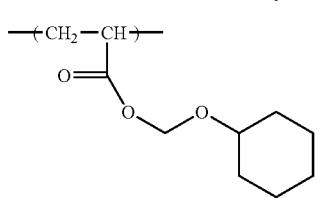
(b1-2-23) 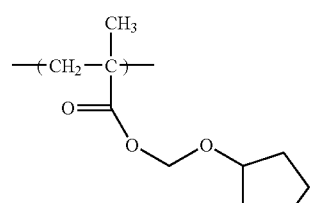
(b1-2-24) 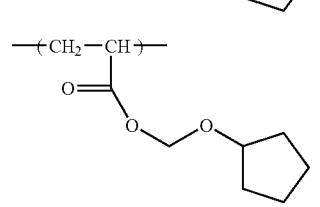

(b1-2-25)
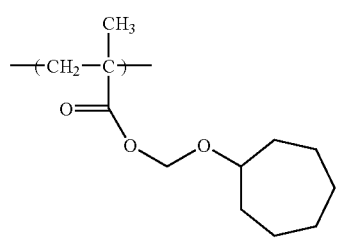
(b1-2-26)
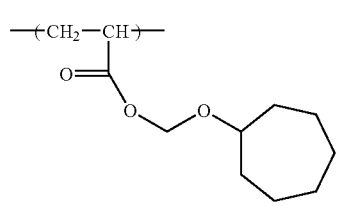
(b1-2-27)
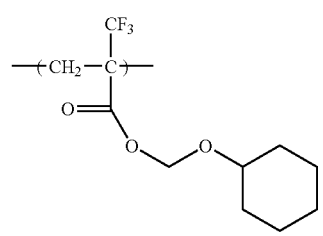
(b1-2-28)
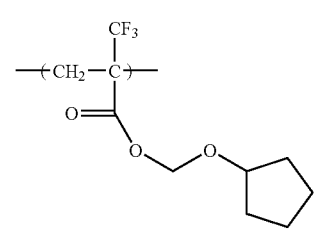
(b1-2-29)
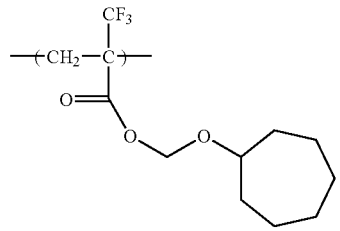
(b1-2-30)
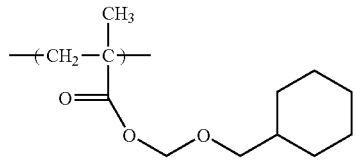
(b1-2-31)
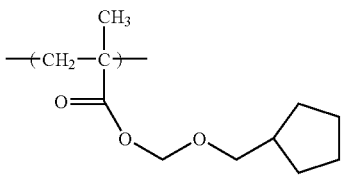
[Chemical Formula 25]
(b1-2-32)
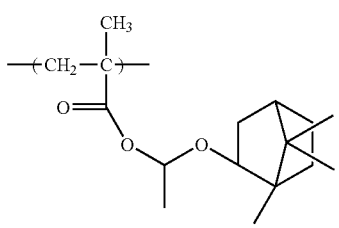
(b1-2-33)
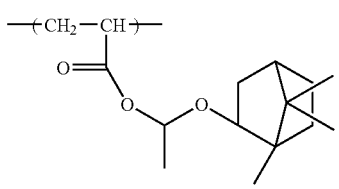
(b1-2-34)
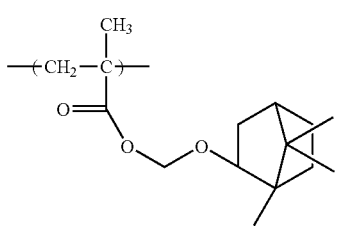
(b1-2-35)
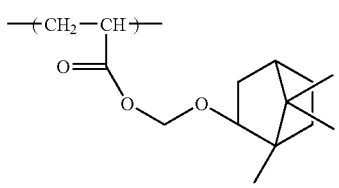
(b1-2-36)
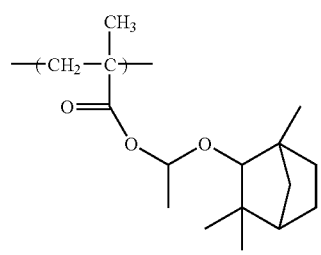
(b1-2-37)
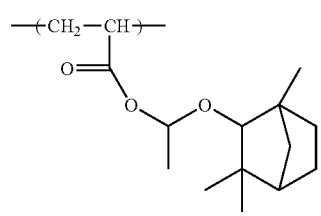
(b1-2-38)
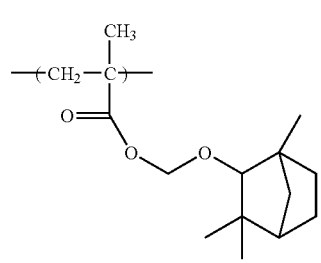

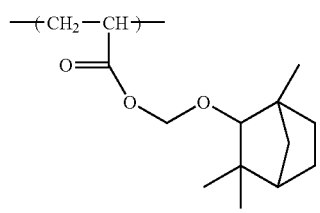 (b1-2-39)
[Chemical Formula 26]
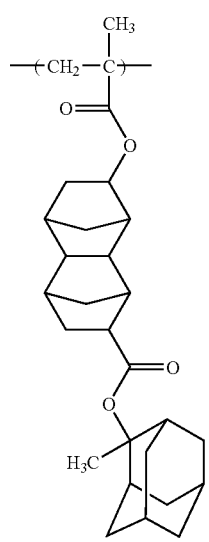 (b1-3-1)
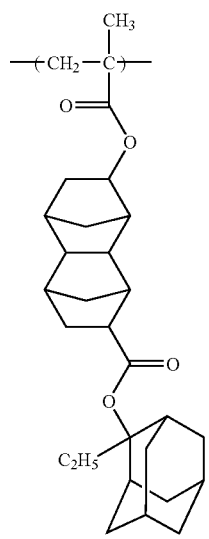 (b1-3-2)
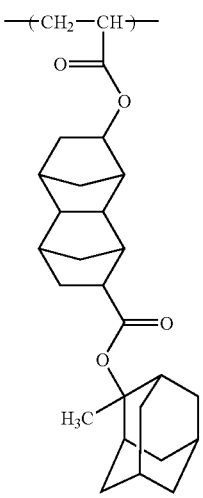 (b1-3-3)
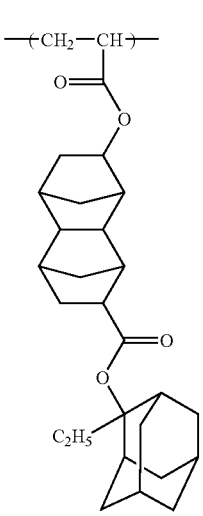 (b1-3-4)
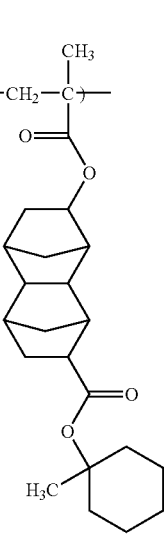 (b1-3-5)

(b1-3-6)
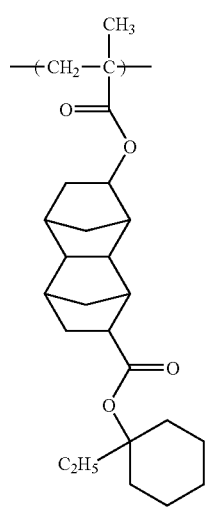
(b1-3-7)
(b1-3-8)
(b1-3-9)
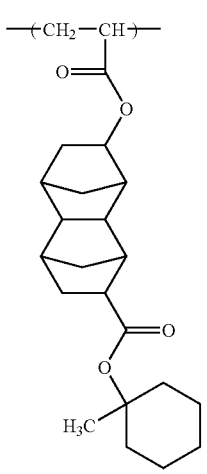
(b1-3-10)
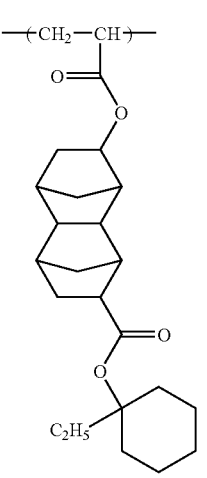
(b1-3-11)
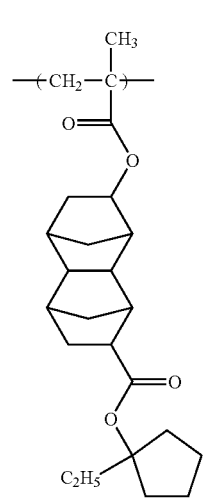

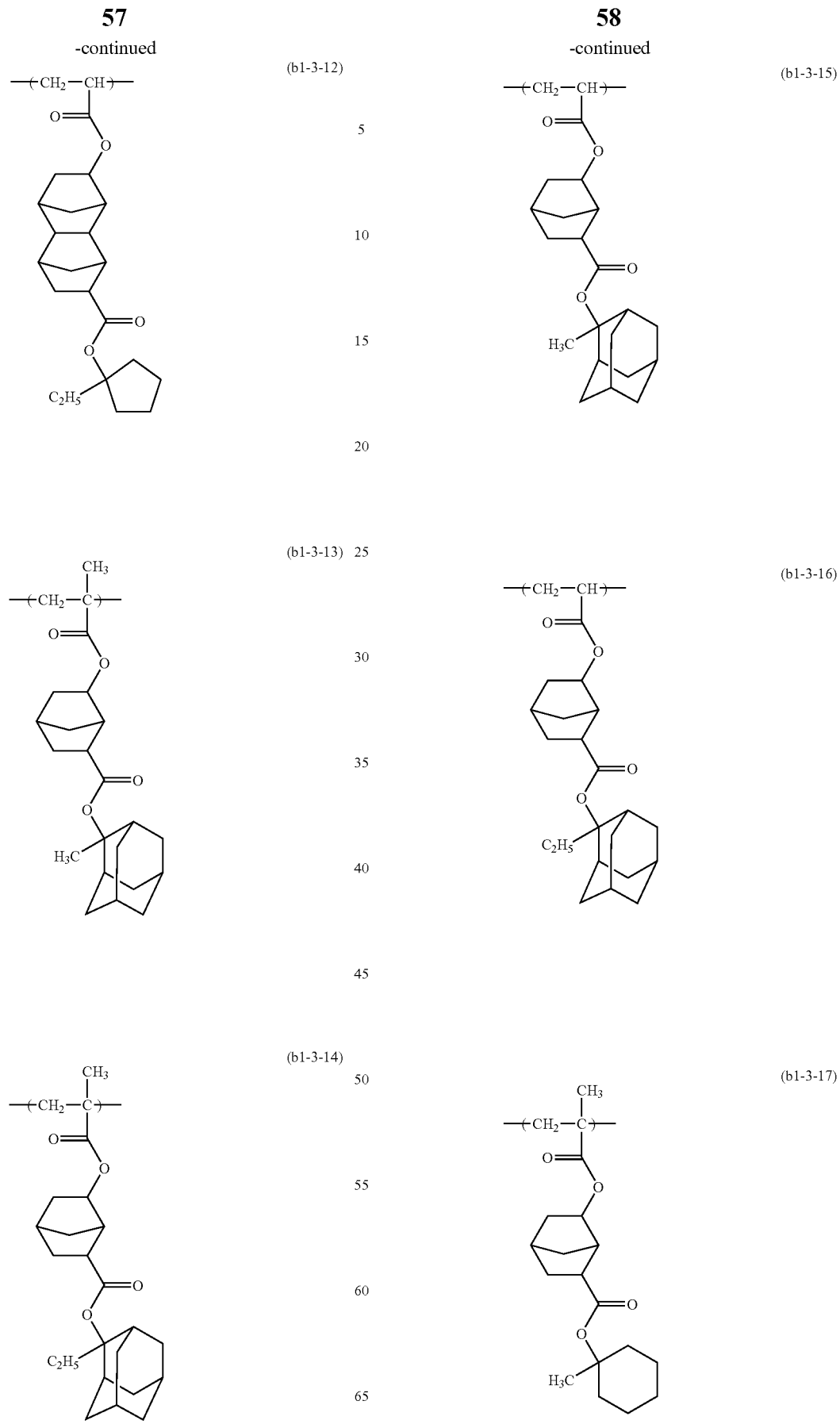

(b1-3-18)
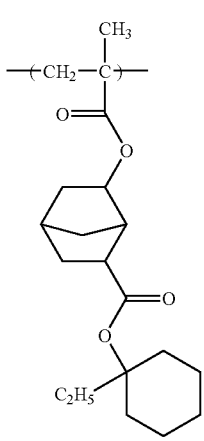
[Chemical Formula 27]
(b1-3-19)
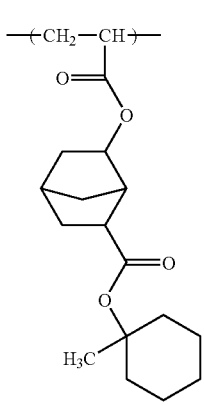
(b1-3-20)
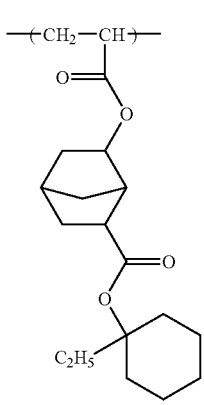
(b1-3-21)
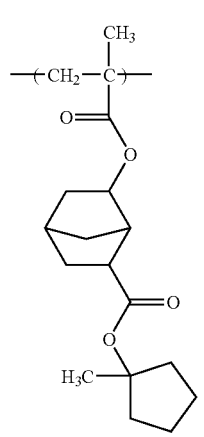
(b1-3-22)
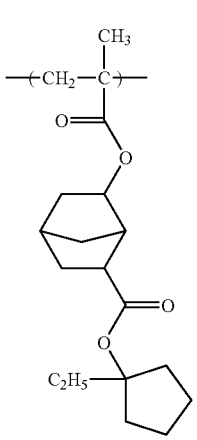
(b1-3-23)
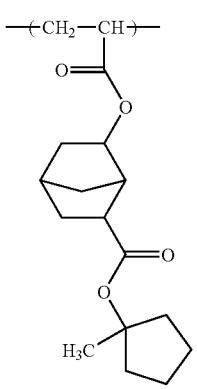
(b1-3-24)
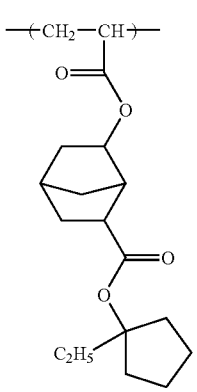
[Chemical Formula 28]
(b1-3-25)
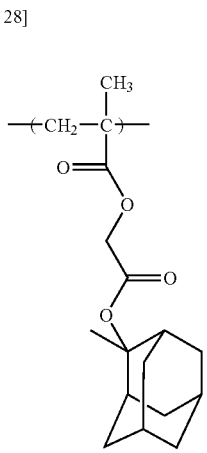

(b1-3-26) 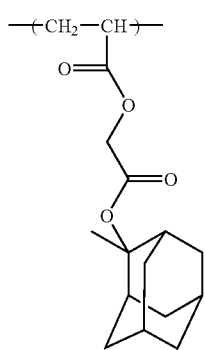
(b1-3-27) 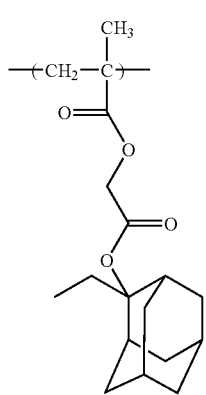
(b1-3-28) 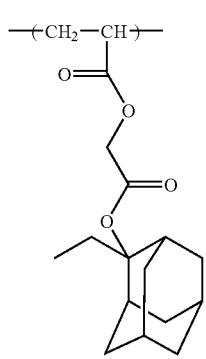
(b1-3-29) 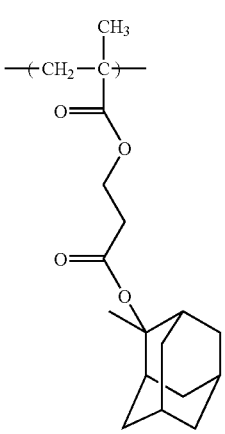
(b1-3-30) 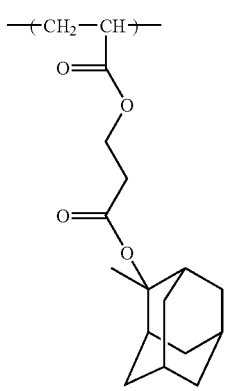
(b1-3-31) 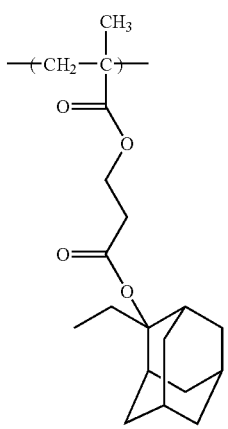
(b1-3-32) 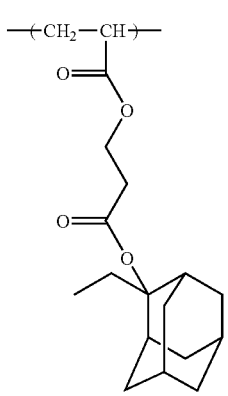
(b1-3-33) 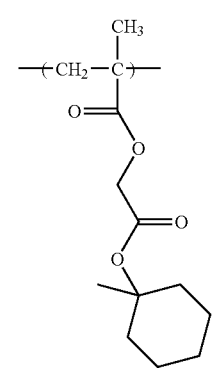

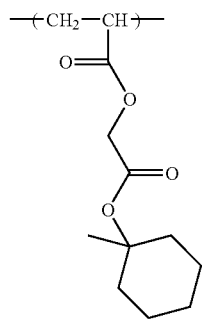 (b1-3-34)
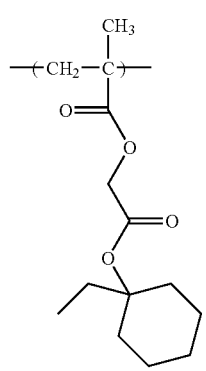 (b1-3-35)
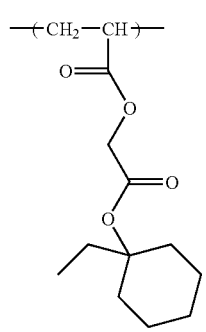 (b1-3-36)
[Chemical Formula 29]
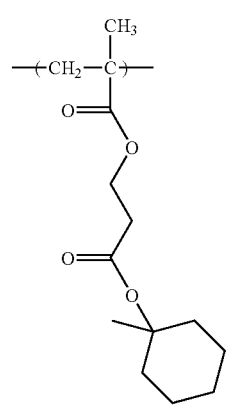 (b1-3-37)
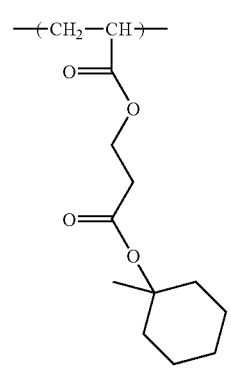 (b1-3-38)
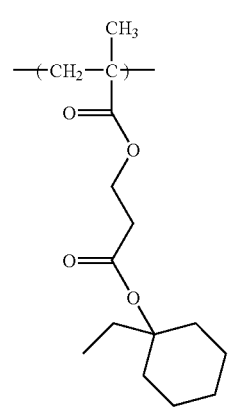 (b1-3-39)
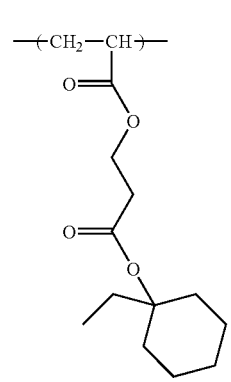 (b1-3-40)
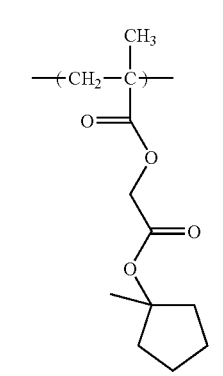 (b1-3-41)

-continued
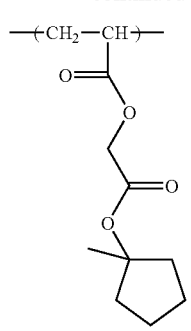 (b1-3-42)
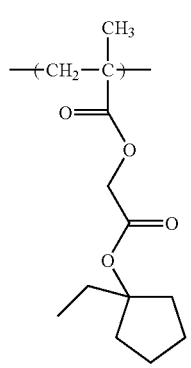 (b1-3-43)
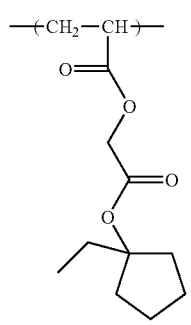 (b1-3-44)
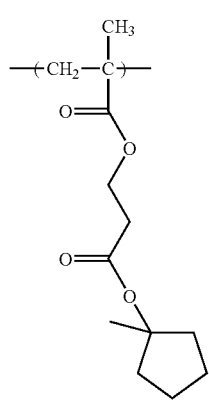 (b1-3-45)
-continued
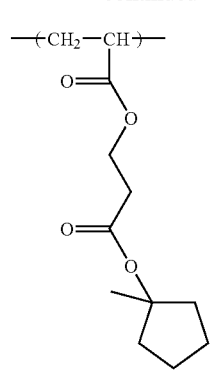 (b1-3-46)
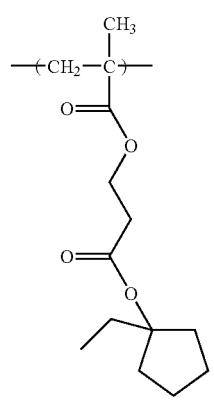 (b1-3-47)
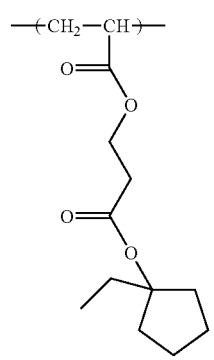 (b1-3-48)
[Chemical Formula 30]
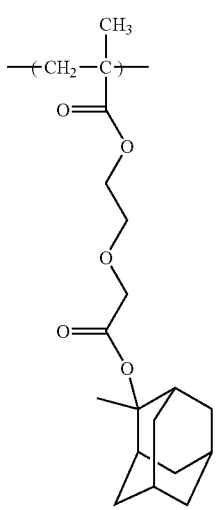 (b1-3-49)

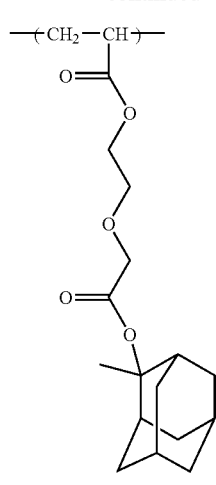 (b1-3-50)
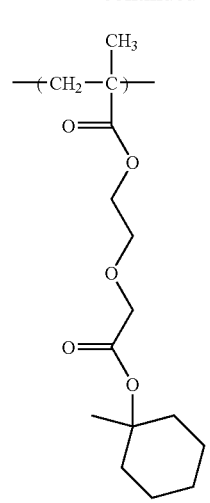 (b1-3-53)
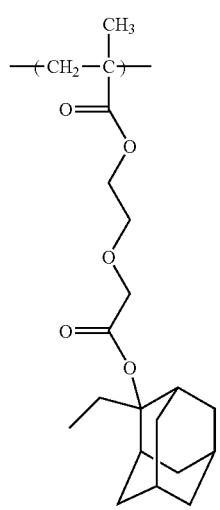 (b1-3-51)
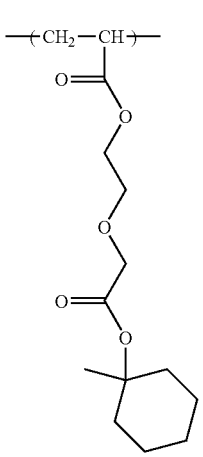 (b1-3-54)
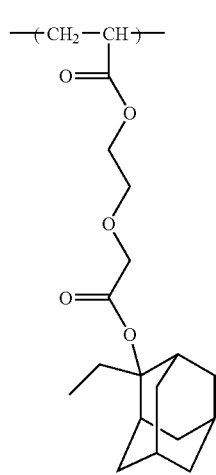 (b1-3-52)
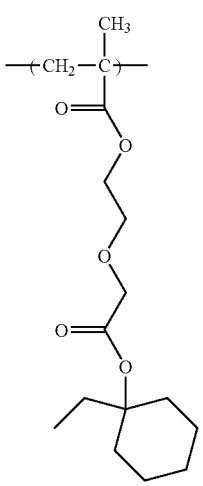 (b1-3-55)

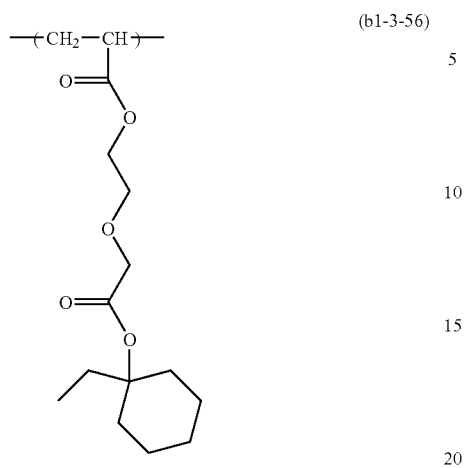
(b1-3-56)
[Chemical Formula 31]
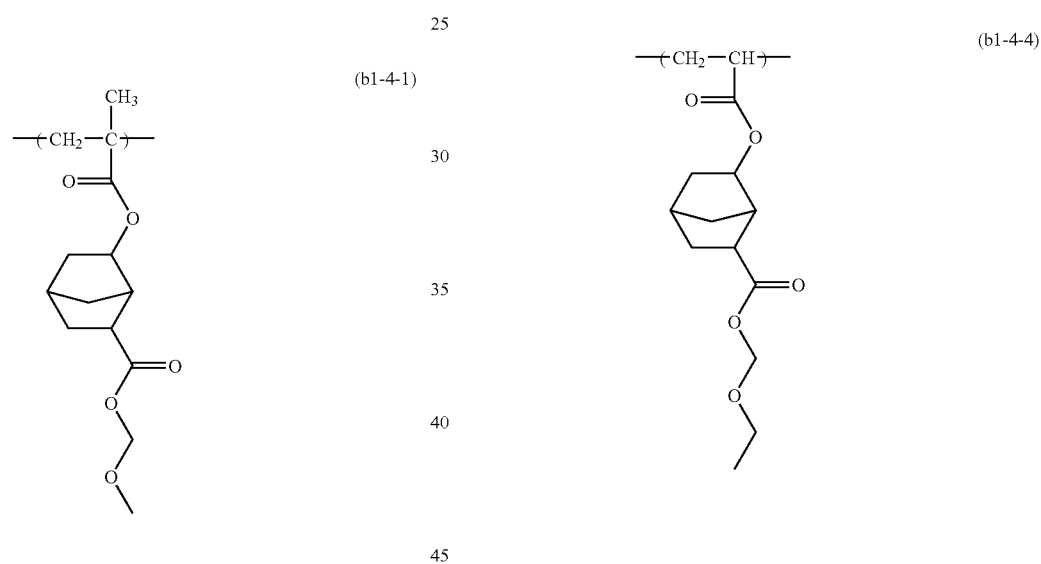
(b1-4-1)
(b1-4-2)
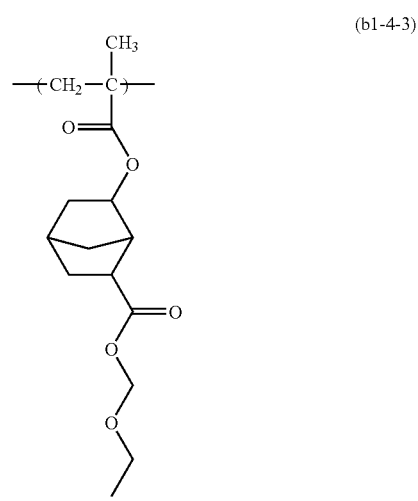
(b1-4-3)
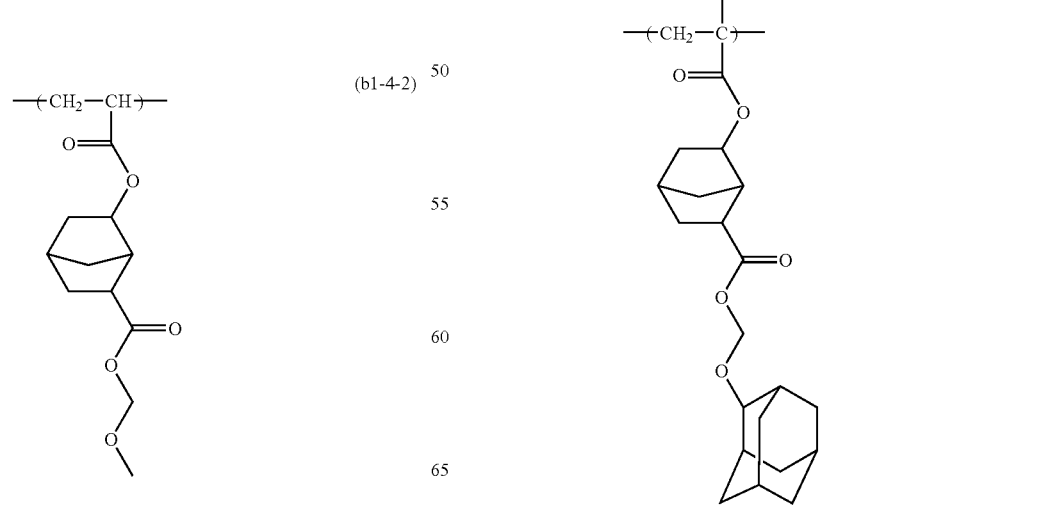
(b1-4-4)
(b1-4-5)

-continued (b1-4-6)
(b1-4-7)
(b1-4-8)
(b1-4-9)
(b1-4-10)
(b1-4-11)

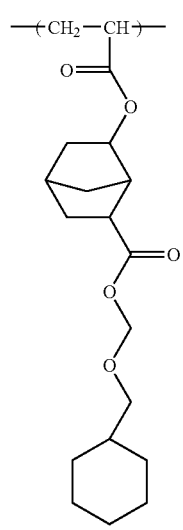 (b1-4-12)
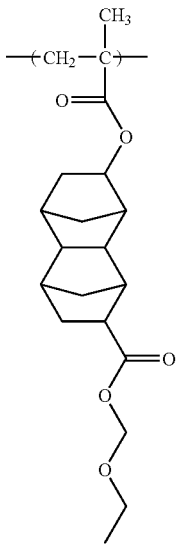 (b1-4-15)
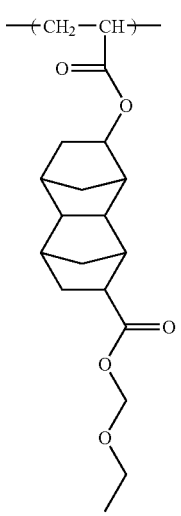 (b1-4-16)
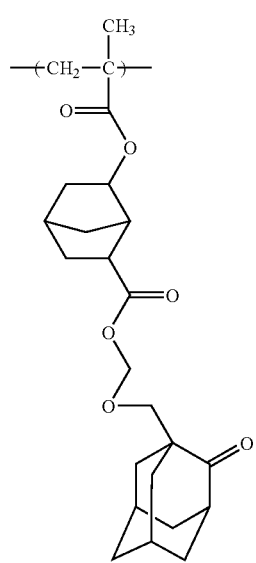 (b1-4-13)
(b1-4-14)
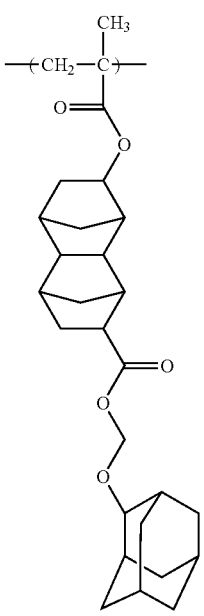 (b1-4-17)

[Chemical Formula 32]
(b1-4-18)
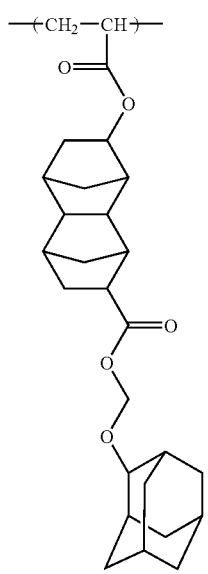
(b1-4-19)
(b1-4-20)
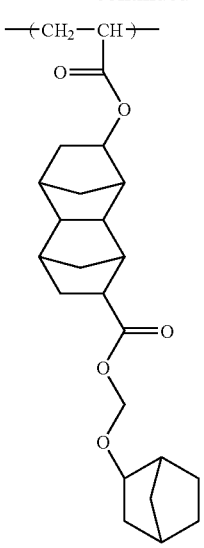
(b1-4-21)
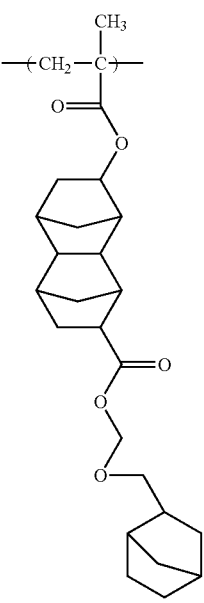
(b1-4-22)
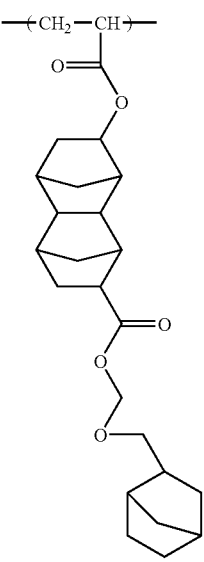

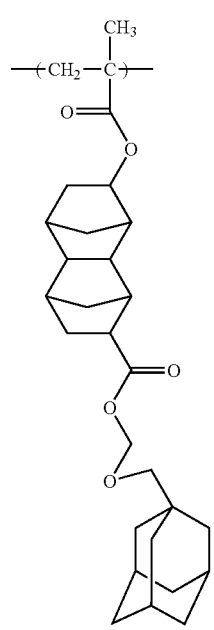
(b1-4-23)
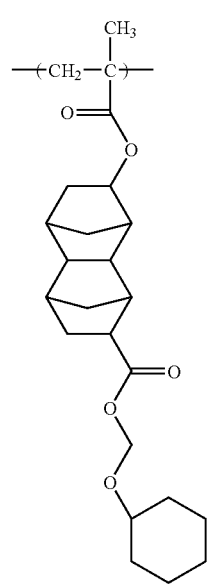
(b1-4-25)
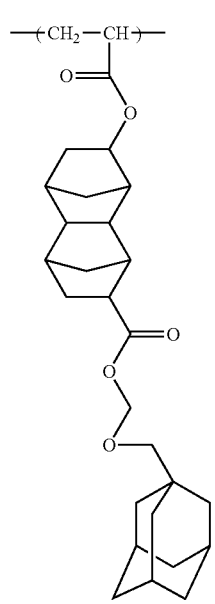
(b1-4-24)
(b1-4-26)

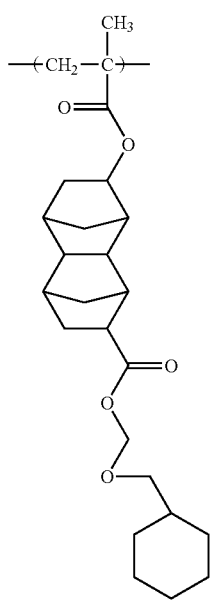 (b1-4-27)

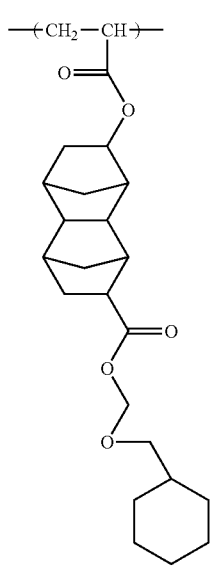 (b1-4-28)

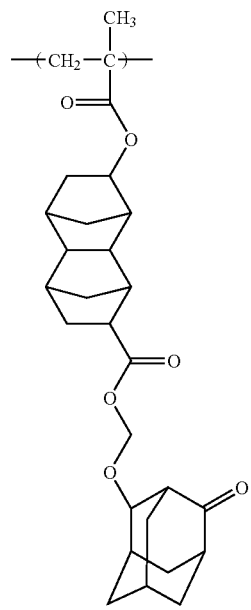 (b1-4-29)

(b1-4-30)

As the structural unit (b1), one type of structural unit may be used, or two or more types may be used in combination.

Among these, structural units represented by general formula (b1-1) are preferable. More specifically, at least one structural unit selected from the group consisting of structural units represented by formulas (b1-1-1) to (b1-1-7) and (b1-1-36) to (b1-1-42) is more preferable.

Further, as the structural unit (b1), structural units represented by general formula (b1-1-01) shown below which includes the structural units represented by formulas (b1-1-1) to (b1-1-5), and structural units represented by general formula (b1-1-02) shown below which includes the structural units represented by formulas (b1-1-36) to (b1-1-42) are also preferable.

[Chemical Formula 33]

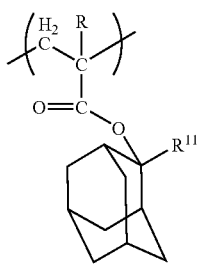

(b1-1-01)

In the formula, R represents a hydrogen atom, a lower alkyl group or a halogenated lower alkyl group; and $R^{11}$ represents a lower alkyl group.

[Chemical Formula 34]

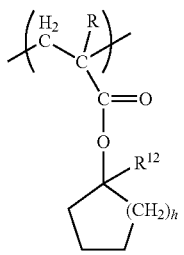

(b1-1-02)

In the formula, R represents a hydrogen atom, a lower alkyl group or a halogenated lower alkyl group; $R^{12}$ represents a lower alkyl group; and h represents an integer of 1 to 3.

In general formula (b1-1-01), R is the same as defined above. The lower alkyl group for is the same as the lower alkyl group for R above, and is preferably a methyl group or an ethyl group.

In general formula (b1-1-02), R is the same as defined above. The lower alkyl group for $R^{12}$ is the same as the lower alkyl group for R above. $R^{12}$ is preferably a methyl group or an ethyl group, and most preferably an ethyl group. h is preferably 1 or 2, and most preferably 2.

As the structural unit (b 1), one type of structural unit may be used, or two or more types may be used in combination.

In the component (B1), the amount of the structural unit (b1) based on the combined total of all structural units constituting the component (B1) is preferably 10 to 80 mol %, more preferably 20 to 70 mol %, and still more preferably 25 to 50 mol %. When the amount of the structural unit (b1) is at least as large as the lower limit of the above-mentioned range, a pattern can be easily formed using a resist composition prepared from the component (B1). On the other hand, when the amount of the structural unit (b1) is no more than the upper limit of the above-mentioned range, a good balance can be achieved with the other structural units.

Structural Unit (b2)

The structural unit (b2) is a structural unit derived from an acrylate ester containing a lactone-containing cyclic group.

The term "lactone-containing cyclic group" refers to a cyclic group including one ring containing a —O—C(O)— structure (lactone ring). The term "lactone ring" refers to a single ring containing a —O—C(O)— structure, and this ring is counted as the first ring. A lactone-containing cyclic group in which the only ring structure is the lactone ring is referred to as a monocyclic group, and groups containing other ring structures are described as polycyclic groups regardless of the structure of the other rings.

When the component (B1) is used for forming a resist film, the lactone-containing cyclic group of the structural unit (b2) is effective in improving the adhesion between the resist film and the substrate, and increasing the compatibility with the developing solution containing water.

As the structural unit (b2), there is no particular limitation, and an arbitrary structural unit may be used.

Specific examples of lactone-containing monocyclic groups include groups in which one hydrogen atom has been removed from γ-butyrolactone. Further, specific examples of lactone-containing polycyclic groups include groups in which one hydrogen atom has been removed from a lactone ring-containing bicycloalkane, tricycloalkane or tetracycloalkane.

More specifically, examples of the structural unit (b2) include structural units represented by general formulas (b2-1) to (b2-5) shown below.

[Chemical Formula 35]

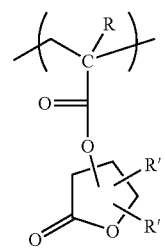

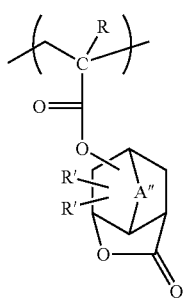

(b2-5)

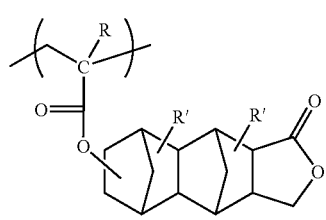

In the formulas, R represents a hydrogen atom, a lower alkyl group or a halogenated lower alkyl group; R' represents a hydrogen atom, a lower alkyl group, an alkoxy group of 1 to 5 carbon atoms or —COOR", wherein R" represents a hydrogen atom or a linear, branched or cyclic alkyl group of 1 to 15 carbon atoms; m represents 0 or 1; and A" represents an oxygen atom, a sulfur atom, or an alkylene group of 1 to 5 carbon atoms which may contain an oxygen atom or a sulfur atom.

In general formulas (b2-1) to (b2-5), R is the same as defined for R in the structural unit (b1).

The lower alkyl group for R' is the same as the lower alkyl group for R in the structural unit (b1).

When R" is a linear or branched alkyl group, it preferably has 1 to 10 carbon atoms, more preferably 1 to 5 carbon atoms.

When R" is a cyclic alkyl group (cycloalkyl group), it preferably has 3 to 15 carbon atoms, more preferably 4 to 12 carbon atoms, and most preferably 5 to 10 carbon atoms. As examples of the cycloalkyl group, groups in which one or more hydrogen atoms have been removed from a monocycloalkane or a polycycloalkane such as a bicycloalkane, tricycloalkane or tetracycloalkane, which may or may not be substituted with a fluorine atom or a fluorinated alkyl group, may be used. Examples of such groups include groups in which one or more hydrogen atoms have been removed from a monocycloalkane such as cyclopentane or cyclohexane; and groups in which one or more hydrogen atoms have been removed from a polycycloalkane such as adamantane, norbornane, isobornane, tricyclodecane or tetracyclododecane.

In the structural units represented by general formulas (b2-1) to (b2-5), in consideration of industrial availability, R' is preferably a hydrogen atom.

Specific examples of alkylene groups of 1 to 5 carbon atoms for A" include a methylene group, an ethylene group, an n-propylene group, an isopropylene group, —O—CH$_2$—, —CH$_2$—O—CH$_2$—, —S—CH$_2$— and —CH$_2$—S—CH$_2$—.

Specific examples of structural units represented by general formulas (b2-1) to (b2-5) are shown below.

[Chemical Formula 36]

(b2-1-1)

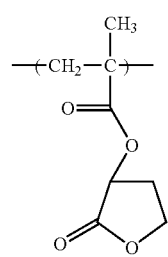

(b2-1-2)

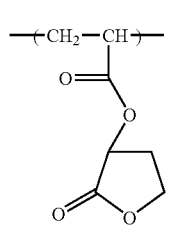

(b2-1-3)

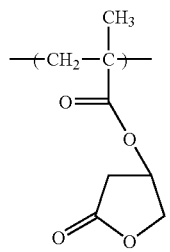

(b2-1-4)

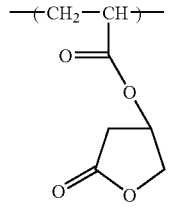

(b2-1-5)

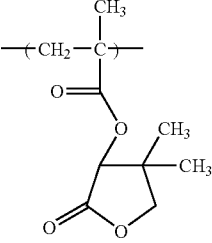

(b2-1-6)

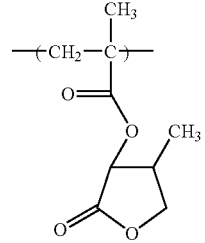

[Chemical Formula 37]

(b2-2-1)

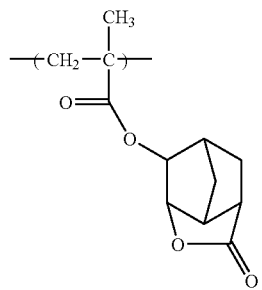

(b2-2-2) 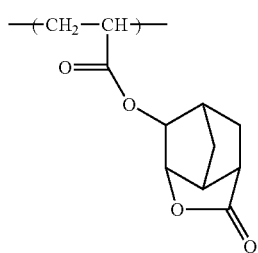
(b2-2-3) 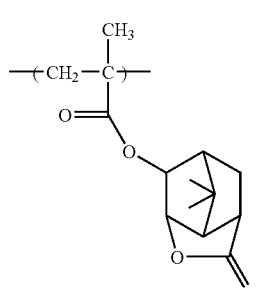
(b2-2-4) 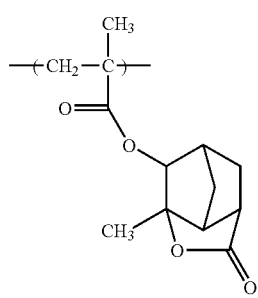
(b2-2-5) 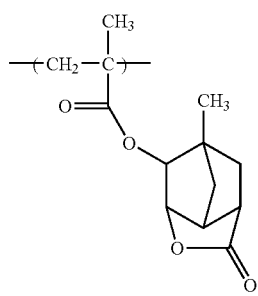
(b2-2-6) 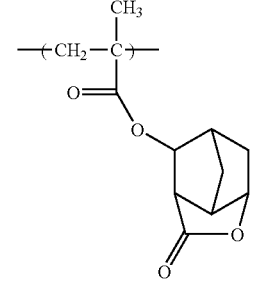
(b2-2-7) 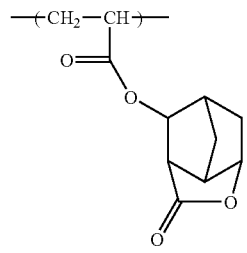
(b2-2-8) 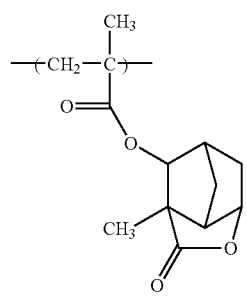
(b2-2-9) 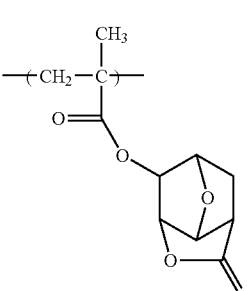
(b2-2-10) 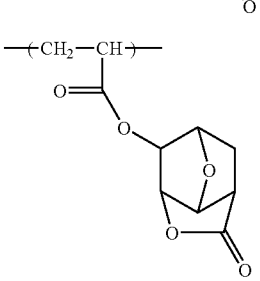
(b2-2-11) 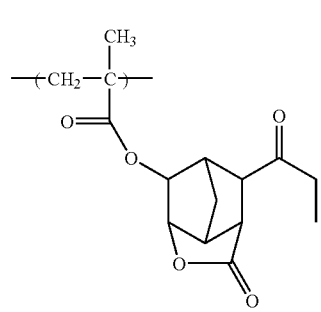
(b2-2-12) 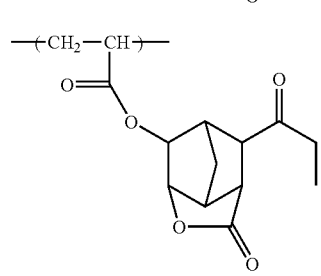

(b2-2-13)
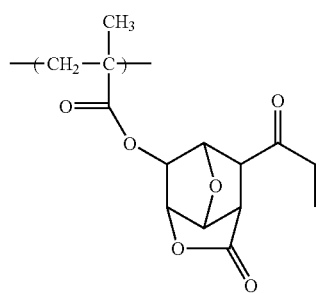
(b2-2-14)
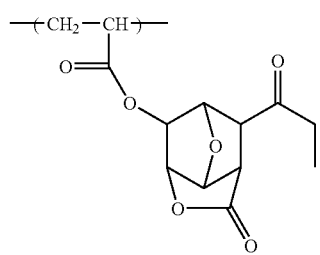
[Chemical Formula 38]
(b2-3-1)
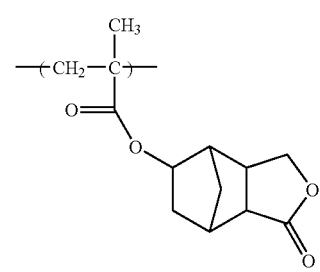
(b2-3-2)
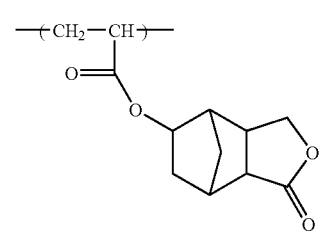
(b2-3-3)
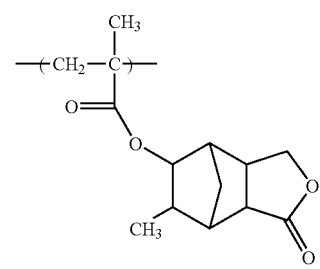
(b2-3-4)
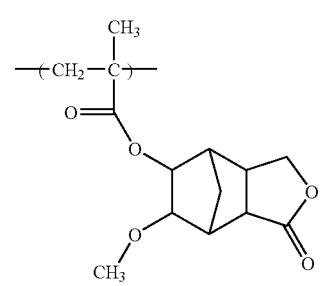
(b2-3-5)
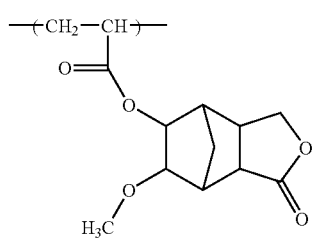
(b2-3-6)
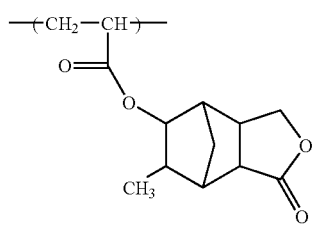
(b2-3-7)
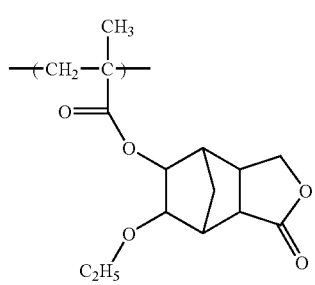
(b2-3-8)
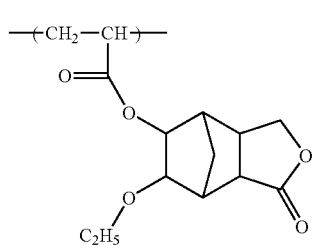
(b2-3-9)
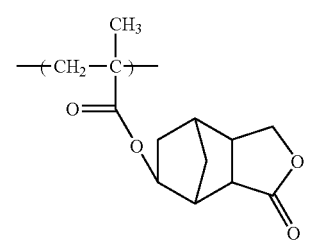
(b2-3-10)
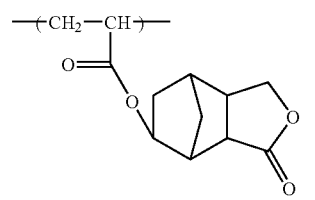

[Chemical Formula 39]
(b2-4-1)
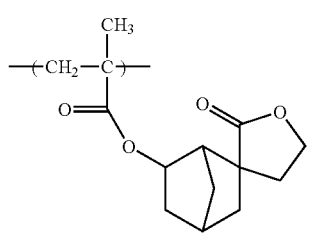
(b2-4-2)
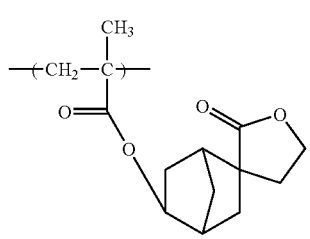
(b2-4-3)
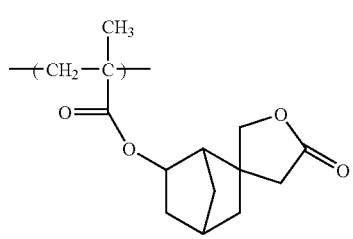
(b2-4-4)
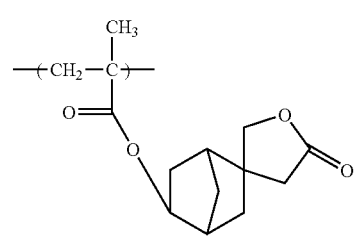
(b2-4-5)
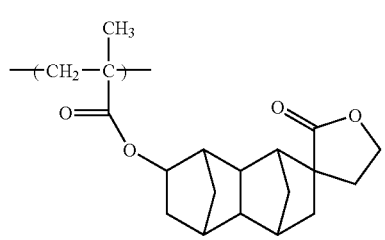
(b2-4-6)
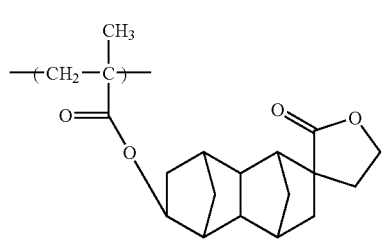
(b2-4-7)
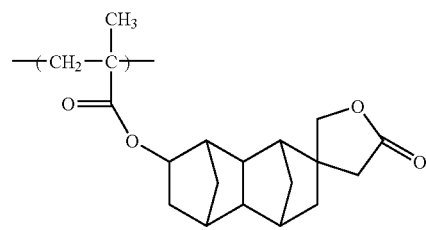
(b2-4-8)
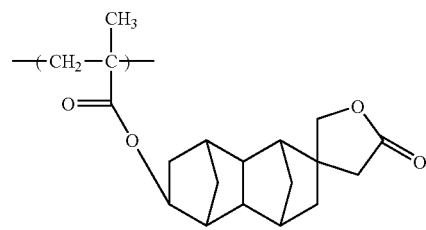
(b2-4-9)
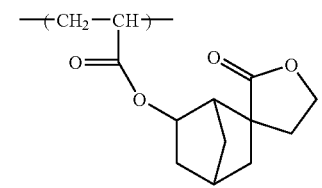
(b2-4-10)
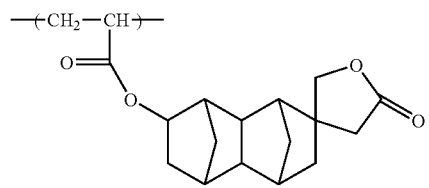
(b2-4-11)
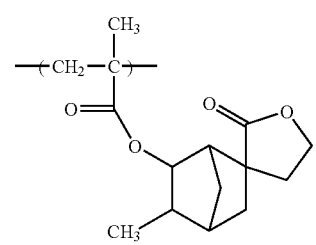
(b2-4-12)
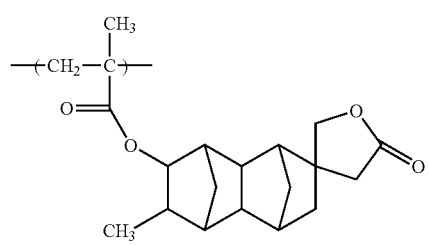

-continued

[Chemical Formula 40]

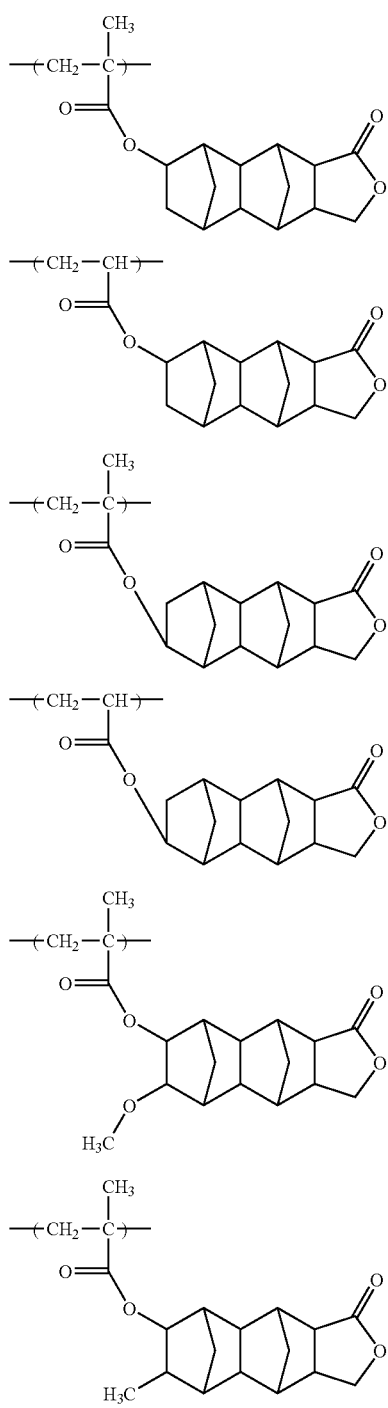

(b2-5-1)
(b2-5-2)
(b2-5-3)
(b2-5-4)
(b2-5-5)
(b2-5-6)

As the structural unit (b2), at least one structural unit selected from the group consisting of formulas (b2-1) to (b2-5) is preferable, and at least one structural unit selected from the group consisting of formulas (b2-1) to (b2-3) is more preferable. Of these, it is preferable to use at least one structural unit selected from the group consisting of structural units represented by formulas (b2-1-1), (b2-1-2), (b2-2-1), (b2-2-2), (b2-2-9), (b2-2-10), (b2-3-1), (b2-3-2), (b2-3-9) and (b2-3-10).

As the structural unit (b2), one type of structural unit may be used, or two or more types may be used in combination.

In the component (B1), the amount of the structural unit (b2) based on the combined total of all structural units constituting the component (B1) is preferably 5 to 60 mol %, more preferably 10 to 50 mol %, and still more preferably 20 to 50 mol %. When the amount of the structural unit (b2) is at least as large as the lower limit of the above-mentioned range, the effect of using the structural unit (b2) can be satisfactorily achieved. On the other hand, when the amount of the structural unit (b2) is no more than the upper limit of the above-mentioned range, a good balance can be achieved with the other structural units.

Structural Unit (b3)

The structural unit (b3) is a structural unit derived from an acrylate ester containing a polar group-containing aliphatic hydrocarbon group.

When the component (B1) includes the structural unit (b3), the hydrophilicity of the component (B1) is improved, and hence, the compatibility of the component (B1) with the developing solution is improved. As a result, the alkali solubility of the exposed portions improves, which contributes to favorable improvements in the resolution.

Examples of the polar group include a hydroxyl group, cyano group, carboxyl group, or hydroxyalkyl group in which some of the hydrogen atoms of the alkyl group have been substituted with fluorine atoms, although a hydroxyl group is particularly desirable.

Examples of the aliphatic hydrocarbon group include linear or branched hydrocarbon groups (preferably alkylene groups) of 1 to 10 carbon atoms, and polycyclic aliphatic hydrocarbon groups (polycyclic groups). These polycyclic groups can be selected appropriately from the multitude of groups that have been proposed for the resins of resist compositions designed for use with ArF excimer lasers. The polycyclic group preferably has 7 to 30 carbon atoms.

Of the various possibilities, structural units derived from an acrylate ester that include an aliphatic polycyclic group that contains a hydroxyl group, cyano group, carboxyl group or a hydroxyalkyl group in which part of the hydrogen atoms of the alkyl group have been substituted with fluorine atoms are particularly desirable. Examples of the polycyclic group include groups in which two or more hydrogen atoms have been removed from a bicycloalkane, tricycloalkane, tetracycloalkane or the like. Specific examples include groups in which two or more hydrogen atoms have been removed from a polycycloalkane such as adamantane, norbornane, isobornane, tricyclodecane or tetracyclododecane. Of these polycyclic groups, groups in which two or more hydrogen atoms have been removed from adamantane, norbornane or tetracyclododecane are preferred industrially.

When the aliphatic hydrocarbon group within the polar group-containing aliphatic hydrocarbon group is a linear or branched hydrocarbon group of 1 to 10 carbon atoms, the structural unit (b3) is preferably a structural unit derived from a hydroxyethyl ester of acrylic acid. On the other hand, when the hydrocarbon group is a polycyclic group, structural units represented by formulas (b3-1), (b3-2) and (b3-3) shown below are preferable.

[Chemical Formula 41]

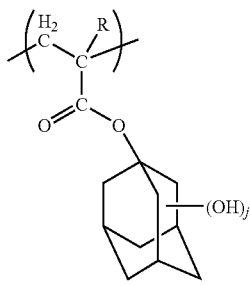
(b3-1)

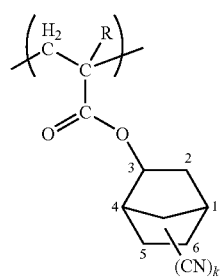
(b3-2)

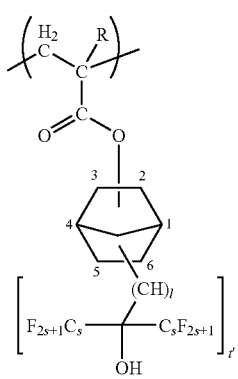
(b3-3)

In the formulas, R is the same as defined above; j represents an integer of 1 to 3; k represents an integer of 1 to 3; t' represents an integer of 1 to 3; l represents an integer of 1 to 5; and s represents an integer of 1 to 3.

In formula (b3-1), j is preferably 1 or 2, and more preferably 1. When j is 2, it is preferable that the hydroxyl groups be bonded to the 3rd and 5th positions of the adamantyl group. When j is 1, it is preferable that the hydroxyl group be bonded to the 3rd position of the adamantyl group. j is preferably 1, and it is particularly desirable that the hydroxyl group be bonded to the 3rd position of the adamantyl group.

In formula (b3-2), k is preferably 1. The cyano group is preferably bonded to the 5th or 6th position of the norbornyl group.

In formula (b3-3), t' is preferably 1. l is preferably 1. s is preferably 1. Further, in formula (b3-3), it is preferable that a 2-norbornyl group or 3-norbornyl group is bonded to the terminal of the carboxy group of the acrylic acid. The fluorinated alkyl alcohol is preferably bonded to the 5th or 6th position of the norbornyl group.

As the structural unit (b3), one type of structural unit may be used, or two or more types may be used in combination.

When the component (B1) contains the structural unit (b3), the amount of structural unit (b3) based on the combined total of all structural units constituting the component (B1) is preferably 5 to 50 mol %, more preferably 5 to 40 mol %, and still more preferably 5 to 25 mol %. When the amount of the structural unit (b3) is at least as large as the lower limit of the above-mentioned range, the effect of using the structural unit (b3) can be satisfactorily achieved. On the other hand, when the amount of the structural unit (b3) is no more than the upper limit of the above-mentioned range, a good balance can be achieved with the other structural units.

Structural Unit (b4)

The component (B1) may also have a structural unit (b4) which is other than the above-mentioned structural units (b1) to (b3), as long as the effects of the present invention are not impaired.

As the structural unit (b4), any other structural unit which cannot be classified as one of the above structural units (b1) to (b3) can be used without any particular limitation, and any of the multitude of conventional structural units used within resist resins for ArF excimer lasers or KrF excimer lasers (and particularly for ArF excimer lasers) can be used.

As the structural unit (b4), a structural unit which contains a non-acid-dissociable aliphatic polycyclic group, and is also derived from an acrylate ester is preferable. Examples of this polycyclic group include the same groups as those described above in connection with the aforementioned structural unit (b1), and any of the multitude of conventional polycyclic groups used within the resin component of resist compositions for ArF excimer lasers or KrF excimer lasers (and particularly for ArF excimer lasers) can be used.

In consideration of industrial availability and the like, at least one polycyclic group selected from amongst a tricyclodecanyl group, adamantyl group, tetracyclododecanyl group, isobornyl group, and norbornyl group is particularly desirable. These polycyclic groups may be substituted with a linear or branched alkyl group of 1 to 5 carbon atoms.

Specific examples of the structural unit (b4) include units with structures represented by general formulas (b4-1) to (b4-5) shown below.

[Chemical Formula 42]

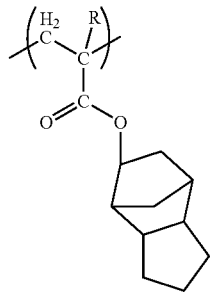
(b4-1)

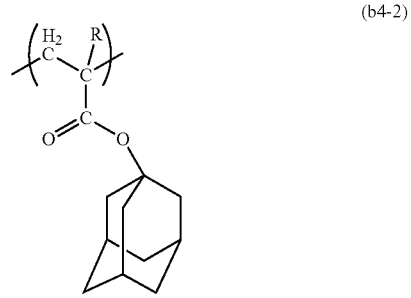
(b4-2)

-continued

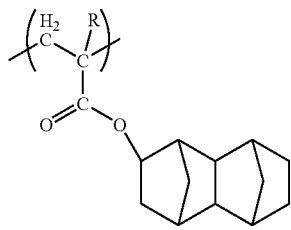
(b4-3)

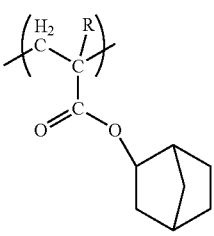
(b4-4)

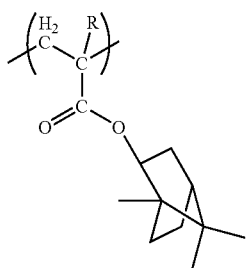
(b4-5)

In the formulas, R is the same as defined above.

When the structural unit (b4) is included in the component (B1), the amount of the structural unit (b4) based on the combined total of all the structural units that constitute the component (B1) is preferably within the range from 1 to 30 mol %, and more preferably from 10 to 20 mol %.

In a resist composition for immersion exposure containing the polymeric compound of the present invention, the component (B1) preferably contains a copolymer having the structural units (b1), (b2) and (b3). Examples of such a copolymer include a copolymer consisting of the structural units (b1) and (b2) and (b3), and a copolymer consisting of the structural units (b1), (b2), (b3) and (b4).

In the component (B), as the component (B1), one type of resin may be used, or two or more types of resins may be used in combination.

In the resist composition for immersion exposure, as the component (B1), a resin that includes a combination of structural units such as that shown below is particularly desirable.

[Chemical Formula 43]

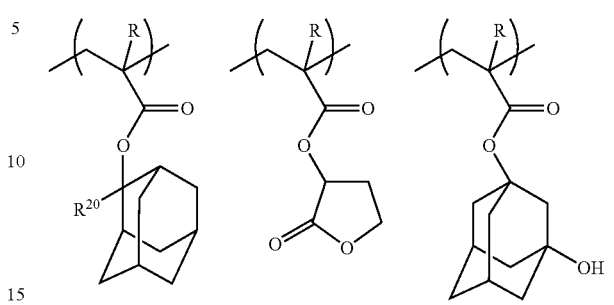
(B1-1)

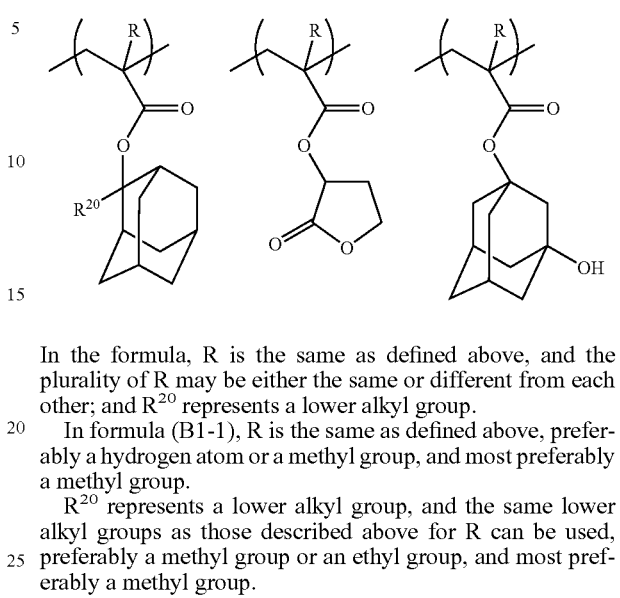

In the formula, R is the same as defined above, and the plurality of R may be either the same or different from each other; and $R^{20}$ represents a lower alkyl group.

In formula (B1-1), R is the same as defined above, preferably a hydrogen atom or a methyl group, and most preferably a methyl group.

$R^{20}$ represents a lower alkyl group, and the same lower alkyl groups as those described above for R can be used, preferably a methyl group or an ethyl group, and most preferably a methyl group.

The component (B1) can be obtained, for example, by a conventional radical polymerization or the like of the monomers corresponding with each of the structural units, using a radical polymerization initiator such as azobisisobutyronitrile (AIBN).

Furthermore, in the component (B1), by using a chain transfer agent such as HS—$CH_2$—$CH_2$—$CH_2$—$C(CF_3)_2$—OH, a —$C(CF_3)_2$—OH group can be introduced at the terminals of the component (B1). Such a copolymer having introduced a hydroxyalkyl group in which some of the hydrogen atoms of the alkyl group are substituted with fluorine atoms is effective in reducing developing defects and LER (line edge roughness: unevenness of the side walls of a line pattern).

The weight average molecular weight (Mw) (the polystyrene equivalent value determined by gel permeation chromatography) of the component (B1) is not particularly limited, but is preferably 2,000 to 50,000, more preferably 3,000 to 30,000, and most preferably 5,000 to 20,000. When the weight average molecular weight is no more than the upper limit of the above-mentioned range, the resist composition exhibits a satisfactory solubility in a resist solvent. On the other hand, when the weight average molecular weight is at least as large as the lower limit of the above-mentioned range, dry etching resistance and the cross-sectional shape of the resist pattern becomes satisfactory.

Further, the dispersity (Mw/Mn) is preferably 1.0 to 5.0, more preferably 1.0 to 3.0, and most preferably 1.2 to 2.5. Here, Mn is the number average molecular weight.

<Component (B2)>

As the component (B2), it is preferable to use a compound that has a molecular weight of at least 500 and less than 2,000, contains a hydrophilic group, and also contains an acid dissociable, dissolution inhibiting group described above in connection with the component (B1). Specific examples include compounds containing a plurality of phenol skeletons in which a part of the hydrogen atoms within hydroxyl groups have been substituted with the aforementioned acid dissociable, dissolution inhibiting groups.

Examples of the component (B2) include low molecular weight phenolic compounds in which a portion of the hydroxyl group hydrogen atoms have been substituted with an aforementioned acid dissociable, dissolution inhibiting group, and these types of compounds are known, for example, as sensitizers or heat resistance improvers for use in non-chemically amplified g-line or i-line resists.

Examples of these low molecular weight phenol compounds include bis(4-hydroxyphenyl)methane, bis(2,3,4-trihydroxyphenyl)methane, 2-(4-hydroxyphenyl)-2-(4'-hydroxyphenyl)propane, 2-(2,3,4-trihydroxyphenyl)-2-(2',3',4'-trihydroxyphenyl)propane, tris(4-hydroxyphenyl)methane, bis(4-hydroxy-3,5-dimethylphenyl)-2-hydroxyphenylmethane, bis(4-hydroxy-2,5-dimethylphenyl)-2-hydroxyphenylmethane, bis(4-hydroxy-3,5-dimethylphenyl)-3,4-dihydroxyphenylmethane, bis(4-hydroxy-2,5-dimethylphenyl)-3,4-dihydroxyphenylmethane, bis(4-hydroxy-3-methylphenyl)-3,4-dihydroxyphenylmethane, bis(3-cyclohexyl-4-hydroxy-6-methylphenyl)-4-hydroxyphenylmethane, bis(3-cyclohexyl-4-hydroxy-6-methylphenyl)-3,4-dihydroxyphenylmethane, 1-[1-(4-hydroxyphenyl)isopropyl]-4-[1,1-bis(4-hydroxyphenyl)ethyl]benzene, and dimers, trimers and tetramers of formalin condensation products of phenols such as phenol, m-cresol, p-cresol and xylenol. Needless to say, the low molecular weight phenol compound is not limited to these examples.

Also, there are no particular limitations on the acid dissociable, dissolution inhibiting group, and suitable examples include the groups described above.

As the component (B), one type may be used, or two or more types of compounds may be used in combination.

Among the above-mentioned examples, as the component (B), a base component that exhibits increased solubility in an alkali developing solution under action of acid is preferable, and it is particularly desirable that the component (B) contain the component (B1).

In the resist composition for immersion exposure containing the polymeric compound of the present invention, the amount of the component (B) can be appropriately adjusted depending on the thickness of the resist film to be formed, and the like.

<Component (C)>

As the component (C), there is no particular limitation, and any of the known acid generators used in conventional chemically amplified resist compositions can be used. Examples of these acid generators are numerous, and include onium salt acid generators such as iodonium salts and sulfonium salts; oxime sulfonate acid generators; diazomethane acid generators such as bisalkyl or bisaryl sulfonyl diazomethanes and poly(bis-sulfonyl)diazomethanes; nitrobenzylsulfonate acid generators; iminosulfonate acid generators; and disulfone acid generators.

As an onium salt acid generator, a compound represented by general formula (c-1) or (c-2) shown below can be used.

[Chemical Formula 44]

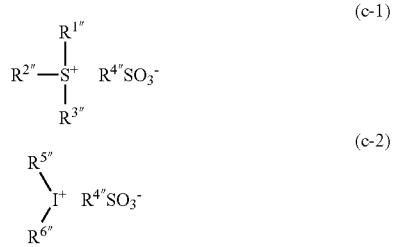

In the formulas above, $R^{1''}$ to $R^{3''}$, $R^{5''}$ and $R^{6''}$ each independently represent an aryl group or alkyl group, wherein two of $R^{1''}$ to $R^{3''}$ in formula (c-1) may be bonded to each other to form a ring with the sulfur atom; and $R^{4''}$ represents an alkyl group, a halogenated alkyl group, an aryl group or an alkenyl group which may have a substituent, with the provision that at least one of $R^{1''}$ to $R^{3''}$ represents an aryl group, and at least one of $R^{5''}$ and $R^{6''}$ represents an aryl group.

In formula (c-1), $R^{1''}$ to $R^{3''}$ each independently represents an aryl group or an alkyl group. In formula (c-1), two of $R^{1''}$ to $R^{3''}$ may be bonded to each other to form a ring with the sulfur atom.

Further, among $R^{1''}$ to $R^{3''}$, at least one group represents an aryl group. Among $R^{1''}$ to $R^{3''}$, two or more groups are preferably aryl groups, and it is particularly desirable that all of $R^{1''}$ to $R^{3''}$ are aryl groups.

The aryl group for $R^{1''}$ to $R^{3''}$ is not particularly limited. For example, an aryl group having 6 to 20 carbon atoms may be used in which part or all of the hydrogen atoms of the aryl group may or may not be substituted with alkyl groups, alkoxy groups, halogen atoms or hydroxyl groups.

The aryl group is preferably an aryl group having 6 to 10 carbon atoms because it can be synthesized at a low cost. Specific examples thereof include a phenyl group and a naphthyl group.

The alkyl group, with which hydrogen atoms of the aryl group may be substituted, is preferably an alkyl group having 1 to 5 carbon atoms, and most preferably a methyl group, an ethyl group, a propyl group, an n-butyl group, or a tert-butyl group.

The alkoxy group, with which hydrogen atoms of the aryl group may be substituted, is preferably an alkoxy group having 1 to 5 carbon atoms, more preferably a methoxy group, an ethoxy group, an n-propoxy group, an iso-propoxy group, an n-butoxy group or a tert-butoxy group, and most preferably a methoxy group or an ethoxy group.

The halogen atom, with which hydrogen atoms of the aryl group may be substituted, is preferably a fluorine atom.

The alkyl group for $R^{1''}$ to $R^{3''}$ is not particularly limited and includes, for example, a linear, branched or cyclic alkyl group having 1 to 10 carbon atoms. In terms of achieving excellent resolution, the alkyl group preferably has 1 to 5 carbon atoms. Specific examples thereof include a methyl group, an ethyl group, an n-propyl group, an isopropyl group, an n-butyl group, an isobutyl group, an n-pentyl group, a cyclopentyl group, a hexyl group, a cyclohexyl group, a nonyl group, and a decanyl group, and a methyl group is most preferable because it is excellent in resolution and can be synthesized at a low cost.

When two of $R^{1''}$ to $R^{3''}$ in formula (c-1) are bonded to each other to form a ring with the sulfur atom, it is preferable that the two of $R^{1''}$ to $R^{3''}$ form a 3- to 10-membered ring including the sulfur atom, and it is particularly desirable that the two of $R^{1''}$ to $R^{3''}$ form a 5- to 7-membered ring including the sulfur atom.

When two of $R^{1''}$ to $R^{3''}$ in formula (c-1) are bonded to each other to form a ring with the sulfur atom, the remaining one of $R^{1''}$ to $R^{3''}$ is preferably an aryl group. As examples of the aryl group, the same as the above-mentioned aryl groups for $R^{1''}$ to $R^{3''}$ can be given.

$R^{4''}$ represents an alkyl group, a halogenated alkyl group, an aryl group or an alkenyl group which may have a substituent.

The alkyl group for $R^{4''}$ may be any of linear, branched or cyclic.

The linear or branched alkyl group preferably has 1 to 10 carbon atoms, more preferably 1 to 8 carbon atoms, and most preferably 1 to 4 carbon atoms.

The cyclic alkyl group preferably has 4 to 15 carbon atoms, more preferably 4 to 10 carbon atoms, and most preferably 6 to 10 carbon atoms.

As an example of the halogenated alkyl group for $R^{4''}$, a group in which part of or all of the hydrogen atoms of the aforementioned linear, branched or cyclic alkyl group have been substituted with halogen atoms can be given. Examples of the aforementioned halogen atom include a fluorine atom, a chlorine atom, a bromine atom and an iodine atom, and a fluorine atom is preferable.

In the halogenated alkyl group, the percentage of the number of halogen atoms based on the total number of halogen atoms and hydrogen atoms (halogenation ratio (%)) is preferably 10 to 100%, more preferably 50 to 100%, and most preferably 100%. Higher halogenation ratio is preferable because the acid strength increases.

The aryl group for $R^{4''}$ is preferably an aryl group of 6 to 20 carbon atoms.

The alkenyl group for $R^{4''}$ is preferably an alkenyl group of 2 to 10 carbon atoms.

With respect to $R^{4''}$, the expression "may have a substituent" means that part of or all of the hydrogen atoms within the aforementioned linear, branched or cyclic alkyl group, halogenated alkyl group, aryl group or alkenyl group may be substituted with substituents (atoms other than hydrogen atoms, or groups).

$R^{4''}$ may have one substituent, or two or more substituents.

Examples of the substituent include a halogen atom, a hetero atom, an alkyl group, a group represented by the formula $R^5$—O— (in the formula, $R^5$ represents a monovalent aromatic organic group, a monovalent aliphatic hydrocarbon group or a hydroxyalkyl group) and a group represented by the formula $R^{51}$—O—C(O)— (in the formula, $R^{51}$ represents a monovalent aliphatic hydrocarbon group which may contain a hetero atom).

Examples of halogen atoms and alkyl groups as substituents for $R^{4''}$ include the same halogen atoms and alkyl groups as those described above with respect to the halogenated alkyl group for $R^{4''}$.

Examples of hetero atoms include an oxygen atom, a nitrogen atom, and a sulfur atom.

In the group represented by the formula $R^5$—O—, examples of the monovalent aromatic organic group for $R^5$ include an aryl group which is an aromatic hydrocarbon ring having one hydrogen atom removed therefrom, such as a phenyl group, a biphenyl group, a fluorenyl group, a naphthyl group, an anthryl group or a phenanthryl group; a heteroaryl group in which part of the carbon atoms constituting the aforementioned aryl group has been substituted with a hetero atom such as an oxygen atom, a sulfur atom or a nitrogen atom; and an arylalkyl group, such as a benzyl group, a phenethyl group, a 1-naphthylmethyl group, a 2-naphthylmethyl group, a 1-naphthylethyl group or a 2-naphthylethyl group.

The alkyl chain within the arylalkyl group preferably has 1 to 4 carbon atom, more preferably 1 or 2, and most preferably 1.

These aryl groups, heteroaryl groups and arylalkyl groups may have a substituent such as an alkyl group of 1 to 10 carbon atoms, a halogenated alkyl group, an alkoxy group, a hydroxyl group or a halogen atom. The alkyl group or halogenated alkyl group as a substituent preferably has 1 to 8 carbon atoms, and more preferably 1 to 4 carbon atoms. Further, the halogenated alkyl group is preferably a fluorinated alkyl group. Examples halogen atoms include a fluorine atom, a chlorine atom, an iodine atom and a bromine atom, and a fluorine atom is preferable.

As the monovalent aromatic organic group for $R^5$, an arylalkyl group is preferable, an arylmethyl group is more preferable, and a naphthylmethyl group is most preferable.

Examples of the monovalent aliphatic hydrocarbon group for $R^5$ include a linear, branched or cyclic, monovalent saturated hydrocarbon group of 1 to 15 carbon atoms and a linear or branched, monovalent unsaturated hydrocarbon group of 2 to 5 carbon atoms.

Examples of the linear, monovalent saturated hydrocarbon group include a methyl group, an ethyl group, a propyl group, a butyl group, a pentyl group, a hexyl group, a heptyl group, an octyl group, a nonyl group and a decyl group.

Examples of the branched, monovalent saturated hydrocarbon group include a 1-methylethyl group, a 1-methylpropyl group, a 2-methylpropyl group, a 1-methylbutyl group, a 2-methylbutyl group, a 3-methylbutyl group, a 1-ethylbutyl group, a 2-ethylbutyl group, a 1-methylpentyl group, a 2-methylpentyl group, a 3-methylpentyl group and a 4-methylpentyl group.

The cyclic, monovalent saturated hydrocarbon group may be either a polycyclic group or a monocyclic group, and examples thereof include groups in which one hydrogen atom has been removed from monocycloalkane or a polycycloalkane (e.g., a bicycloalkane, a tricycloalkane or a tetracycloalkane). More specific examples include groups in which one hydrogen atom has been removed from a monocycloalkane such as cyclopentane, cyclohexane, cycloheptane or cyclooctane; and groups in which one hydrogen atom has been removed from a polycycloalkane such as adamantane, norbornane, isobornane, tricyclodecane or tetracyclododecane.

Examples of linear monovalent unsaturated hydrocarbon groups include a vinyl group, a propenyl group (an allyl group) and a butynyl group.

Examples of branched monovalent unsaturated hydrocarbon groups include a 1-methylpropenyl group and a 2-methylpropenyl group.

The monovalent hydrocarbon group for $R^5$ preferably has 2 to 4 carbon atoms, and most preferably 3 carbon atoms.

The hydroxyalkyl group for $R^5$ is a linear, branched or cyclic, monovalent saturated hydrocarbon group in which at least one hydrogen atom has been substituted with a hydroxy group. The hydroxyalkyl group is preferably a linear or branched, monovalent saturated hydrocarbon group in which one or two hydrogen atoms have been substituted with a hydroxy group. Specific examples thereof include a hydroxymethyl group, a hydroxyethyl group, a 1-hydroxypropyl group, a 2-hydroxypropyl group, a 3-hydroxypropyl group and a 2,3-dihydroxypropyl group.

The monovalent hydroxyalkyl group for $R^5$ preferably has 1 to 10 carbon atoms, more preferably 1 to 8 carbon atoms, still more preferably 1 to 6 carbon atoms, and most preferably 1 to 3 carbon atoms.

In the group represented by the formula $R^{51}$—O—C(O)—, the monovalent aliphatic hydrocarbon group represented by $R^{51}$ is the same as defined for the monovalent aliphatic hydrocarbon group represented by $R^5$, and a cyclic alkyl group is particularly desirable. The cyclic alkyl group may have a substituent. Examples of the substituent include a lower alkyl group of 1 to 5 carbon atoms, a fluorine atom, a fluorinated lower alkyl group of 1 to 5 carbon atoms, and an oxygen atom (=O).

The monovalent aliphatic hydrocarbon group may contain a hetero atom. Examples of cyclic alkyl groups containing a hetero atom include groups represented by formulas (L1) to (L5) and (S1) to (54) shown below.

[Chemical Formula 45]

(L1) 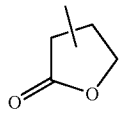

(L2) 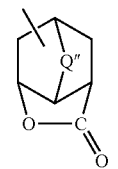

(L3) 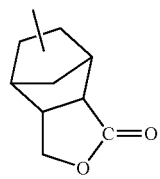

(L4) 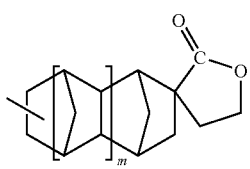

(L5) 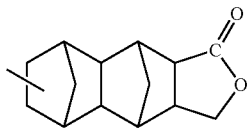

(S1) 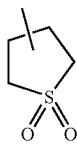

(S2) 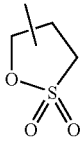

(S3) 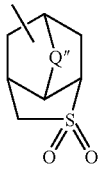

(S4) 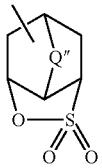

In the formula, Q" represents an alkylene group of 1 to 5 carbon atoms, —O—, —S—, —O—$R^{94}$— or —S—$R^{95}$— (wherein each of $R^{94}$ and $R^{95}$ independently represents an alkylene group of 1 to 5 carbon atoms); and m represents 0 or 1.

In formula (c-2), $R^{5'''}$ and $R^{6'''}$ each independently represents an aryl group or an alkyl group. At least one of $R^{5'''}$ and $R^{6'''}$ represents an aryl group. It is preferable that both of $R^{5'''}$ and $R^{6'''}$ represent an aryl group.

As the aryl group for $R^{5'''}$ and $R^{6'''}$, the same as the aryl groups for $R^{1'''}$ to $R^{3'''}$ can be used.

As the alkyl group for $R^{5'''}$ and $R^{6'''}$, the same as the alkyl groups for $R^{1'''}$ to $R^{3'''}$ can be used.

It is particularly desirable that both of $R^{5'''}$ and $R^{6'''}$ represents a phenyl group.

As $R^{4'''}$ in formula (c-2), the same groups as those mentioned above for $R^{4'''}$ in formula (c-1) can be used.

Specific examples of suitable onium salt acid generators represented by formula (c-1) or (c-2) include diphenyliodonium trifluoromethanesulfonate or nonafluorobutanesulfonate; bis(4-tert-butylphenyl)iodonium trifluoromethanesulfonate or nonafluorobutanesulfonate; triphenylsulfonium trifluoromethanesulfonate, heptafluoropropanesulfonate or nonafluorobutanesulfonate; tri(4-methylphenyl)sulfonium trifluoromethanesulfonate, heptafluoropropanesulfonate or nonafluorobutanesulfonate; dimethyl(4-hydroxynaphthyl)sulfonium trifluoromethanesulfonate, heptafluoropropanesulfonate or nonafluorobutanesulfonate; monophenyldimethylsulfonium trifluoromethanesulfonate, heptafluoropropanesulfonate or nonafluorobutanesulfonate; diphenylmonomethylsulfonium trifluoromethanesulfonate, heptafluoropropanesulfonate or nonafluorobutanesulfonate; (4-methylphenyl)diphenylsulfonium trifluoromethanesulfonate, heptafluoropropanesulfonate or nonafluorobutanesulfonate; (4-methoxyphenyl)diphenylsulfonium trifluoromethanesulfonate, heptafluoropropanesulfonate or nonafluorobutanesulfonate; tri(4-tert-butyl)phenylsulfonium trifluoromethanesulfonate, heptafluoropropanesulfonate or nonafluorobutanesulfonate; diphenyl(1-(4-methoxy)naphthyl)sulfonium trifluoromethanesulfonate, heptafluoropropanesulfonate or nonafluorobutanesulfonate; di(1-naphthyl)phenylsulfonium trifluoromethanesulfonate, heptafluoropropanesulfonate or nonafluorobutanesulfonate; 1-phenyltetrahydrothiophenium trifluoromethanesulfonate, heptafluoropropanesulfonate or nonafluorobutanesulfonate; 1-(4-methylphenyl)tetrahydrothiophenium trifluoromethanesulfonate, heptafluoropropanesulfonate or nonafluorobutanesulfonate; 1-(3,5-dimethyl-4-hydroxyphenyl)tetrahydrothiophenium trifluoromethanesulfonate, heptafluoropropanesulfonate or nonafluorobutanesulfonate; 1-(4-methoxynaphthalene-1-yl)tetrahydrothiophenium trifluoromethanesulfonate, heptafluoropropanesulfonate or nonafluorobutanesulfonate; 1-(4-ethoxynaphthalene-1-yl)tetrahydrothiophenium trifluoromethanesulfonate, heptafluoropropanesulfonate or nonafluorobutanesulfonate; 1-(4-n-butoxynaphthalene-1-yl)tetrahydrothiophenium trifluoromethanesulfonate, heptafluoropropanesulfonate or nonafluorobutanesulfonate; 1-phenyltetrahydrothiopyranium trifluoromethanesulfonate, heptafluoropropanesulfonate or nonafluorobutanesulfonate; 1-(4-hydroxyphenyl)tetrahydrothiopyranium trifluoromethanesulfonate, heptafluoropropanesulfonate or nonafluorobutanesulfonate; 1-(3,5-dimethyl-4-hydroxyphenyl)tetrahydrothiopyranium trifluoromethanesulfonate, heptafluoropropanesulfonate or nonafluorobutanesulfonate; and 1-(4-methylphenyl)tetrahydrothiopyranium trifluoromethanesulfonate, heptafluoropropanesulfonate or nonafluorobutanesulfonate.

It is also possible to use onium salts in which the anion moiety of these onium salts are replaced by methanesulfonate, n-propanesulfonate, n-butanesulfonate, or n-octanesulfonate.

Further, onium salt-based acid generators in which the anion moiety in general formula (c-1) or (c-2) is replaced by an anion moiety represented by general formula (c-3) or (c-4) shown below (the cation moiety the same as (c-1) or (c-2)) may also be used.

[Chemical Formula 46]

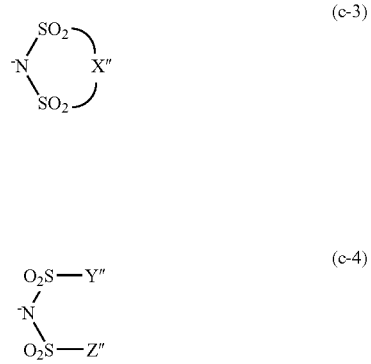

(c-3)

(c-4)

In the formulas, X" represents an alkylene group of 2 to 6 carbon atoms in which at least one hydrogen atom has been substituted with a fluorine atom; and each of Y" and Z" independently represents an alkyl group of 1 to 10 carbon atoms in which at least one hydrogen atom has been substituted with a fluorine atom.

X" represents a linear or branched alkylene group in which at least one hydrogen atom has been substituted with a fluorine atom, and the alkylene group has 2 to 6 carbon atoms, preferably 3 to 5 carbon atoms, and most preferably 3 carbon atoms.

Each of Y" and Z" independently represents a linear or branched alkyl group in which at least one hydrogen atom has been substituted with a fluorine atom, and the alkyl group has 1 to 10 carbon atoms, preferably 1 to 7 carbon atoms, and most preferably 1 to 3 carbon atoms.

The smaller the number of carbon atoms of the alkylene group for X" or those of the alkyl group for Y" and Z" within the above-mentioned range of the number of carbon atoms, the more the solubility in a resist solvent is improved.

Further, in the alkylene group for X" or the alkyl group for Y" and Z", it is preferable that the number of hydrogen atoms substituted with fluorine atoms is as large as possible because the acid strength increases and the transparency to high energy radiation of 200 nm or less or electron beam is improved. The fluorination ratio of the alkylene group or alkyl group is preferably from 70 to 100%, more preferably from 90 to 100%, and it is particularly desirable that the alkylene group or alkyl group be a perfluoroalkylene group or perfluoroalkyl group in which all hydrogen atoms are substituted with fluorine atoms.

Furthermore, as an onium salt-based acid generator, a sulfonium salt having a cation moiety represented by general formula (c-5) or (c-6) shown below may be used.

[Chemical Formula 47]

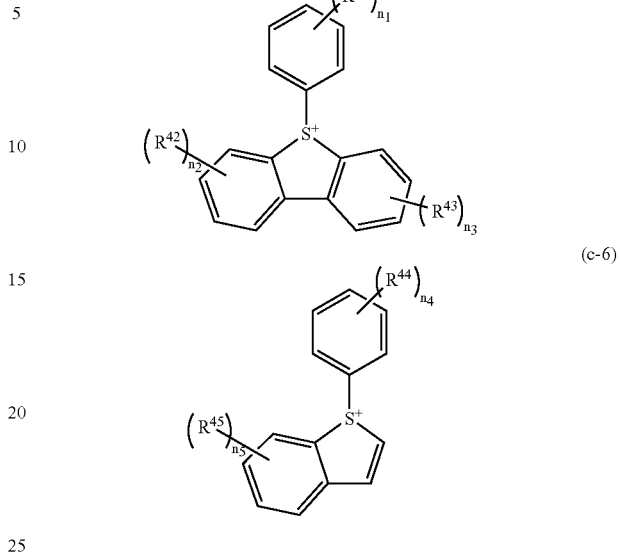

In the formulas, each of $R^{41}$ to $R^{46}$ independently represents an alkyl group, an acetyl group, an alkoxy group, a carboxy group, a hydroxyl group or a hydroxyalkyl group; each of $n_1$ to $n_5$ independently represents an integer of 0 to 3; and $n_6$ represents an integer of 0 to 2.

With respect to $R^{41}$ to $R^{46}$, the alkyl group is preferably an alkyl group of 1 to 5 carbon atoms, more preferably a linear or branched alkyl group, and most preferably a methyl group, ethyl group, propyl group, isopropyl group, n-butyl group or tert-butyl group.

The alkoxy group is preferably an alkoxy group of 1 to 5 carbon atoms, more preferably a linear or branched alkoxy group, and most preferably a methoxy group or ethoxy group.

The hydroxyalkyl group is preferably the aforementioned alkyl group in which one or more hydrogen atoms have been substituted with hydroxy groups, and examples thereof include a hydroxymethyl group, a hydroxyethyl group and a hydroxypropyl group.

If there are two or more of an individual $R^{41}$ to $R^{46}$ group, as indicated by the corresponding value of $n_1$ to $n_6$, then the two or more of the individual $R^{41}$ to $R^{46}$ group may be the same or different from each other.

$n_1$ is preferably 0 to 2, more preferably 0 or 1, and still more preferably 0.

It is preferable that $n_2$ and $n_3$ each independently represent 0 or 1, and more preferably 0.

$n_4$ is preferably 0 to 2, and more preferably 0 or 1.

$n_5$ is preferably 0 or 1, and more preferably 0.

$n_6$ is preferably 0 or 1, and more preferably 1.

The anion moiety of the sulfonium salt having a cation moiety represented by general formula (c-5) or (c-6) is not particularly limited, and the same anion moieties for onium salt-based acid generators which have been proposed may be used. Examples of such anion moieties include fluorinated alkylsulfonic acid ions such as anion moieties ($R^{4"}SO_3^-$) for onium salt-based acid generators represented by general formula (c-1) or (c-2) shown above; and anion moieties represented by general formula (c-3) or (c-4) shown above.

In the present description, an oximesulfonate-based acid generator is a compound having at least one group represented by general formula (C-1) shown below, and has a feature of generating acid by irradiation. Such oxime-sulfonate acid generators are widely used for a chemically amplified resist composition, and can be appropriately selected.

[Chemical Formula 48]

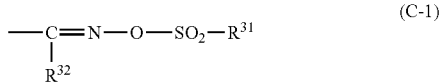

(C-1)

In formula (C-1), each of $R^{31}$ and $R^{32}$ independently represents an organic group.

The organic group for $R^{31}$ and $R^{32}$ refers to a group containing a carbon atom, and may include atoms other than carbon atoms (e.g., a hydrogen atom, an oxygen atom, a nitrogen atom, a sulfur atom, a halogen atom (such as a fluorine atom and a chlorine atom) and the like).

As the organic group for $R^{31}$, a linear, branched, or cyclic alkyl group or aryl group is preferable. The alkyl group or the aryl group may have a substituent. The substituent is not particularly limited, and examples thereof include a fluorine atom and a linear, branched, or cyclic alkyl group having 1 to 6 carbon atoms. The alkyl group or the aryl group "has a substituent" means that part or all of the hydrogen atoms of the alkyl group or the aryl group is substituted with a substituent.

The alkyl group preferably has 1 to 20 carbon atoms, more preferably 1 to 10 carbon atoms, still more preferably 1 to 8 carbon atoms, still more preferably 1 to 6 carbon atoms, and most preferably 1 to 4 carbon atoms. As the alkyl group, a partially or completely halogenated alkyl group (hereinafter, sometimes referred to as a "halogenated alkyl group") is particularly desirable. The "partially halogenated alkyl group" refers to an alkyl group in which part of the hydrogen atoms are substituted with halogen atoms and the "completely halogenated alkyl group" refers to an alkyl group in which all of the hydrogen atoms are substituted with halogen atoms. Examples of halogen atoms include fluorine atoms, chlorine atoms, bromine atoms and iodine atoms, and fluorine atoms are particularly desirable. In other words, the halogenated alkyl group is preferably a fluorinated alkyl group.

The aryl group preferably has 4 to 20 carbon atoms, more preferably 4 to 10 carbon atoms, and most preferably 6 to 10 carbon atoms. As the aryl group, partially or completely halogenated aryl group is particularly desirable. The "partially halogenated aryl group" refers to an aryl group in which some of the hydrogen atoms are substituted with halogen atoms and the "completely halogenated aryl group" refers to an aryl group in which all of hydrogen atoms are substituted with halogen atoms.

As $R^{31}$, an alkyl group of 1 to 4 carbon atoms which has no substituent or a fluorinated alkyl group of 1 to 4 carbon atoms is particularly desirable.

As the organic group for $R^{32}$, a linear, branched, or cyclic alkyl group, aryl group, or cyano group is preferable. Examples of the alkyl group and the aryl group for $R^{32}$ include the same alkyl groups and aryl groups as those described above for $R^{31}$.

As $R^{32}$, a cyano group, an alkyl group of 1 to 8 carbon atoms having no substituent or a fluorinated alkyl group of 1 to 8 carbon atoms is particularly desirable.

Preferred examples of the oxime sulfonate acid generator include compounds represented by general formula (C-2) or (C-3) shown below.

[Chemical Formula 49]

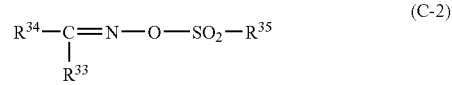

(C-2)

In formula (C-2), $R^{33}$ represents a cyano group, an alkyl group having no substituent or a halogenated alkyl group; $R^{34}$ represents an aryl group; and $R^{35}$ represents an alkyl group having no substituent or a halogenated alkyl group.

[Chemical Formula 50]

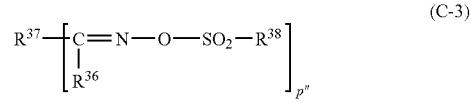

(C-3)

In formula (C-3), $R^{36}$ represents a cyano group, an alkyl group having no substituent or a halogenated alkyl group; $R^{37}$ represents a divalent or trivalent aromatic hydrocarbon group; $R^{38}$ represents an alkyl group having no substituent or a halogenated alkyl group; and p" represents 2 or 3.

In general formula (C-2), the alkyl group having no substituent or the halogenated alkyl group for $R^{33}$ preferably has 1 to 10 carbon atoms, more preferably 1 to 8 carbon atoms, and most preferably 1 to 6 carbon atoms.

As $R^{33}$, a halogenated alkyl group is preferable, and a fluorinated alkyl group is more preferable.

The fluorinated alkyl group for $R^{33}$ preferably has 50% or more of the hydrogen atoms thereof fluorinated, more preferably 70% or more, and most preferably 90% or more.

Examples of the aryl group for $R^{34}$ include groups in which one hydrogen atom has been removed from an aromatic hydrocarbon ring, such as a phenyl group, a biphenyl group, a fluorenyl group, a naphthyl group, an anthryl group, and a phenanthryl group, and heteroaryl groups in which some of the carbon atoms constituting the ring(s) of these groups are substituted with hetero atoms such as an oxygen atom, a sulfur atom, and a nitrogen atom. Of these, a fluorenyl group is preferable.

The aryl group for $R^{34}$ may have a substituent such as an alkyl group of 1 to 10 carbon atoms, a halogenated alkyl group, or an alkoxy group. The alkyl group and halogenated alkyl group as the substituent preferably has 1 to 8 carbon atoms, and more preferably 1 to 4 carbon atoms. Further, the halogenated alkyl group is preferably a fluorinated alkyl group.

The alkyl group having no substituent or the halogenated alkyl group for $R^{35}$ preferably has 1 to 10 carbon atoms, more preferably 1 to 8 carbon atoms, and most preferably 1 to 6 carbon atoms.

As $R^{35}$, a halogenated alkyl group is preferable, and a fluorinated alkyl group is more preferable.

In terms of enhancing the strength of the acid generated, the fluorinated alkyl group for $R^{35}$ preferably has 50% or more of the hydrogen atoms fluorinated, more preferably 70% or more, still more preferably 90% or more. A completely fluorinated alkyl group in which 100% of the hydrogen atoms are substituted with fluorine atoms is particularly desirable.

In general formula (C-3), as the alkyl group having no substituent and the halogenated alkyl group for $R^{36}$, the same alkyl group having no substituent and the halogenated alkyl group described above for $R^{33}$ can be used.

Examples of the divalent or trivalent aromatic hydrocarbon group for $R^{37}$ include groups in which one or two hydrogen atoms have been removed from the aryl group for $R^{34}$.

As the alkyl group having no substituent or the halogenated alkyl group for $R^{38}$, the same one as the alkyl group having no substituent or the halogenated alkyl group for $R^{35}$ can be used.

p" is preferably 2.

Specific examples of suitable oxime sulfonate acid generators include α-(p-toluenesulfonyloxyimino)-benzyl cyanide, α-(p-chlorobenzenesulfonyloxyimino)-benzyl cyanide, α-(4-nitrobenzenesulfonyloxyimino)-benzyl cyanide, α-(4-nitro-2-trifluoromethylbenzenesulfonyloxyimino)-benzyl cyanide, α-(benzenesulfonyloxyimino)-4-chlorobenzyl cyanide, α-(benzenesulfonyloxyimino)-2,4-dichlorobenzyl cyanide, α-(benzenesulfonyloxyimino)-2,6-dichlorobenzyl cyanide, α-(benzenesulfonyloxyimino)-4-methoxybenzyl cyanide, α-(2-chlorobenzenesulfonyloxyimino)-4-methoxybenzyl cyanide, α-(benzenesulfonyloxyimino)-thien-2-yl acetonitrile, α-(4-dodecylbenzenesulfonyloxyimino)benzyl cyanide, α-[(p-toluenesulfonyloxyimino)-4-methoxyphenyl]acetonitrile, α-[(dodecylbenzenesulfonyloxyimino)-4-methoxyphenyl]acetonitrile, α-(tosyloxyimino)-4-thienyl cyanide, α-(methylsulfonyloxyimino)-1-cyclopentenyl acetonitrile, α-(methylsulfonyloxyimino)-1-cyclohexenyl acetonitrile, α-(methylsulfonyloxyimino)-1-cycloheptenyl acetonitrile, α-(methylsulfonyloxyimino)-1-cyclooctenyl acetonitrile, α-(trifluoromethylsulfonyloxyimino)-1-cyclopentenyl acetonitrile, α-(trifluoromethylsulfonyloxyimino)-cyclohexyl acetonitrile, α-(ethylsulfonyloxyimino)-ethyl acetonitrile, α-(propylsulfonyloxyimino)-propyl acetonitrile, α-(cyclohexylsulfonyloxyimino)-cyclopentyl acetonitrile, α-(cyclohexylsulfonyloxyimino)-cyclohexyl acetonitrile, α-(cyclohexylsulfonyloxyimino)-1-cyclopentenyl acetonitrile, α-(ethylsulfonyloxyimino)-1-cyclopentenyl acetonitrile, α-(isopropylsulfonyloxyimino)-1-cyclopentenyl acetonitrile, α-(n-butylsulfonyloxyimino)-1-cyclopentenyl acetonitrile, α-(ethylsulfonyloxyimino)-1-cyclohexenyl acetonitrile, α-(isopropylsulfonyloxyimino)-1-cyclohexenyl acetonitrile, α-(n-butylsulfonyloxyimino)-1-cyclohexenyl acetonitrile, α-(methylsulfonyloxyimino)-phenyl acetonitrile, α-(methylsulfonyloxyimino)-p-methoxyphenyl acetonitrile, α-(trifluoromethylsulfonyloxyimino)-phenyl acetonitrile, α-(trifluoromethylsulfonyloxyimino)-p-methoxyphenyl acetonitrile, α-(ethylsulfonyloxyimino)-p-methoxyphenyl acetonitrile, α-(propylsulfonyloxyimino)-p-methylphenyl acetonitrile, and α-(methylsulfonyloxyimino)-p-bromophenyl acetonitrile.

Further, oxime sulfonate-based acid generators disclosed in Japanese Unexamined Patent Application, First Publication No. Hei 9-208554 (Chemical Formulas 18 and 19 shown in paragraphs [0012] to [0014]) and oxime sulfonate-based acid generators disclosed in WO 2004/074242A2 (Examples 1 to 40 described at pages 65 to 85) may be preferably used.

Furthermore, as preferable examples, the following can be used.

[Chemical Formula 51]

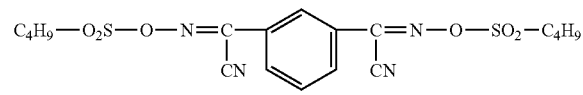

-continued

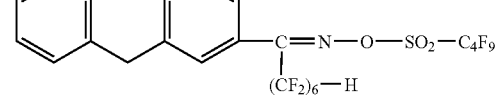
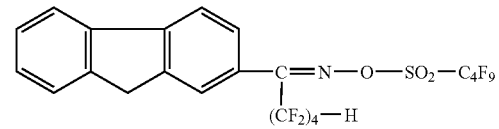

Of the aforementioned diazomethane acid generators, specific examples of suitable bisalkyl or bisaryl sulfonyl diazomethanes include bis(isopropylsulfonyl)diazomethane, bis(p-toluenesulfonyl)diazomethane, bis(1,1-dimethylethylsulfonyl)diazomethane, bis(cyclohexylsulfonyl)diazomethane, and bis(2,4-dimethylphenylsulfonyl)diazomethane.

Further, diazomethane acid generators disclosed in Japanese Unexamined Patent Application, First Publication No. Hei 11-035551, Japanese Unexamined Patent Application, First Publication No. Hei 11-035552 and Japanese Unexamined Patent Application, First Publication No. Hei 11-035573 may be preferably used.

Furthermore, as examples of poly(bis-sulfonyl)diazomethanes, those disclosed in Japanese Unexamined Patent Application, First Publication No. Hei 11-322707, including 1,3-bis(phenylsulfonyldiazomethylsulfonyl)propane, 1,4-bis(phenylsulfonyldiazomethylsulfonyl)butane, 1,6-bis(phenylsulfonyldiazomethylsulfonyl)hexane, 1,10-bis(phenylsulfonyldiazomethylsulfonyl)decane, 1,2-bis(cyclohexylsulfonyldiazomethylsulfonyl)ethane, 1,3-bis(cyclohexylsulfonyldiazomethylsulfonyl)propane, 1,6-bis(cyclohexylsulfonyldiazomethylsulfonyl)hexane, and 1,10-bis(cyclohexylsulfonyldiazomethylsulfonyl)decane, may be given.

As the component (C), one type of acid generator may be used, or two or more types of acid generators may be used in combination.

In the present invention, as the component (C), it is preferable to use an onium salt having a triarylsulfonium ion as the cation moiety and a fluorinated alkylsulfonic acid ion which may have a substituent as the anion moiety.

In the resist composition for immersion exposure containing the polymeric compound of the present invention, the amount of the component (C) relative to 100 parts by weight of the component (B) is preferably 0.5 to 30 parts by weight, and more preferably 1 to 10 parts by weight. When the amount of the component (B) is within the above-mentioned range, formation of a resist pattern can be satisfactorily performed. Further, by virtue of the above-mentioned range, a uniform solution can be obtained and the storage stability becomes satisfactory.

<Optional Components>

In the resist composition for immersion exposure, in order to improve the resist pattern shape and the post exposure stability of the latent image formed by the pattern-wise exposure of the resist layer, it is preferable to add a nitrogen-containing organic compound (D) (hereafter referred to as "component (D)") as an optional component.

A multitude of these components (D) have already been proposed, and any of these known compounds may be used, although an aliphatic amine, and particularly a secondary aliphatic amine or tertiary aliphatic amine is preferable. An aliphatic amine is an amine having one or more aliphatic groups, and the aliphatic groups preferably have 1 to 12 carbon atoms.

Examples of these aliphatic amines include amines in which at least one hydrogen atom of ammonia ($NH_3$) has been substituted with an alkyl group or hydroxyalkyl group of no more than 12 carbon atoms (i.e., alkylamines or alkylalcoholamines), and cyclic amines.

Specific examples of alkylamines and alkylalcoholamines include monoalkylamines such as n-hexylamine, n-heptylamine, n-octylamine, n-nonylamine, and n-decylamine; dialkylamines such as diethylamine, di-n-propylamine, di-n-heptylamine, di-n-octylamine, and dicyclohexylamine; trialkylamines such as trimethylamine, triethylamine, tri-n-propylamine, tri-n-butylamine, tri-n-hexylamine, tri-n-pentylamine, tri-n-heptylamine, tri-n-octylamine, tri-n-nonylamine, tri-n-decanylamine, and tri-n-dodecylamine; and alkyl alcohol amines such as diethanolamine, triethanolamine, diisopropanolamine, triisopropanolamine, di-n-octanolamine, and tri-n-octanolamine. Among these, trialkylamines of 5 to 10 carbon atoms are preferable, and tri-n-pentylamine is particularly desirable.

Examples of the cyclic amine include heterocyclic compounds containing a nitrogen atom as a hetero atom. The heterocyclic compound may be a monocyclic compound (aliphatic monocyclic amine), or a polycyclic compound (aliphatic polycyclic amine).

Specific examples of the aliphatic monocyclic amine include piperidine, and piperazine.

The aliphatic polycyclic amine preferably has 6 to 10 carbon atoms, and specific examples thereof include 1,5-diazabicyclo[4.3.0]-5-nonene, 1,8-diazabicyclo[5.4.0]-7-undecene, hexamethylenetetramine, and 1,4-diazabicyclo[2.2.2]octane.

These compounds can be used either alone, or in combinations of two or more different compounds.

The component (D) is typically used in an amount within a range from 0.01 to 5.0 parts by weight, relative to 100 parts by weight of the component (B).

Furthermore, in the resist composition for immersion exposure, for preventing any deterioration in sensitivity, and improving the resist pattern shape and the post exposure stability of the latent image formed by the pattern-wise exposure of the resist layer, at least one compound (E) (hereafter referred to as "component (E)") selected from the group consisting of an organic carboxylic acid, or a phosphorus oxo acid or derivative thereof can be added.

Examples of suitable organic carboxylic acids include acetic acid, malonic acid, citric acid, malic acid, succinic acid, benzoic acid, and salicylic acid.

Examples of phosphorus oxo acids or derivatives thereof include phosphoric acid, phosphonic acid and phosphinic acid. Among these, phosphonic acid is particularly desirable.

Examples of oxo acid derivatives include esters in which a hydrogen atom within the above-mentioned oxo acids is substituted with a hydrocarbon group. Examples of the hydrocarbon group include an alkyl group of 1 to 5 carbon atoms and an aryl group of 6 to 15 carbon atoms.

Examples of phosphoric acid derivatives include phosphoric acid esters such as di-n-butyl phosphate and diphenyl phosphate.

Examples of phosphonic acid derivatives include phosphonic acid esters such as dimethyl phosphonate, di-n-butyl phosphonate, phenylphosphonic acid, diphenyl phosphonate and dibenzyl phosphonate.

Examples of phosphinic acid derivatives include phosphinic acid esters such as phenylphosphinic acid.

As the component (E), one type may be used alone, or two or more types may be used in combination.

As the component (E), an organic carboxylic acid is preferable, and salicylic acid is particularly desirable.

The component (E) is typically used in an amount within a range from 0.01 to 5.0 parts by weight, relative to 100 parts by weight of the component (B).

If desired, other miscible additives can also be added to the resist composition for immersion exposure. Examples of such miscible additives include additive resins for improving the performance of the resist film, surfactants for improving the applicability, dissolution inhibitors, plasticizers, stabilizers, colorants, halation prevention agents, and dyes.

<Organic Solvent (S)>

The resist composition for immersion exposure can be prepared by dissolving the materials for the resist composition in an organic solvent (hereafter, frequently referred to as "component (S)").

The component (S) may be any organic solvent which can dissolve the respective components to give a uniform solution, and one or more kinds of any organic solvent can be appropriately selected from those which have been conventionally known as solvents for a chemically amplified resist.

Examples thereof include lactones such as γ-butyrolactone;

ketones such as acetone, methyl ethyl ketone, cyclohexanone, methyl-n-pentyl ketone, methyl isopentyl ketone, and 2-heptanone;

polyhydric alcohols, such as ethylene glycol, diethylene glycol, propylene glycol and dipropylene glycol;

compounds having an ester bond, such as ethylene glycol monoacetate, diethylene glycol monoacetate, propylene glycol monoacetate, and dipropylene glycol monoacetate; polyhydric alcohol derivatives including compounds having an ether bond, such as a monoalkylether (e.g., monomethylether, monoethylether, monopropylether or monobutylether) or monophenylether of any of these polyhydric alcohols or compounds having an ester bond (among these, propylene glycol monomethyl ether acetate (PGMEA) and propylene glycol monomethyl ether (PGME) are preferable);

cyclic ethers such as dioxane; esters such as methyl lactate, ethyl lactate (EL), methyl acetate, ethyl acetate, butyl acetate, methyl pyruvate, ethyl pyruvate, methyl methoxypropionate, and ethyl ethoxypropionate;

and aromatic organic solvents such as anisole, ethylbenzylether, cresylmethylether, diphenylether, dibenzylether, phenetole, butylphenylether, ethylbenzene, diethylbenzene, pentylbenzene, isopropylbenzene, toluene, xylene, cymene and mesitylene.

These solvents can be used individually, or in combination as a mixed solvent.

Among these, propylene glycol monomethyl ether acetate (PGMEA), propylene glycol monomethyl ether (PGME) and ethyl lactate (EL) are preferable.

Further, among the mixed solvents, a mixed solvent obtained by mixing PGMEA with a polar solvent is preferable. The mixing ratio (weight ratio) of the mixed solvent can be appropriately determined, taking into consideration the compatibility of the PGMEA with the polar solvent, but is preferably in the range of 1:9 to 9:1, more preferably from 2:8 to 8:2.

Specifically, when EL is mixed as the polar solvent, the PGMEA:EL weight ratio is preferably from 1:9 to 9:1, and more preferably from 2:8 to 8:2. Alternatively, when PGME is mixed as the polar solvent, the PGMEA:PGME is preferably from 1:9 to 9:1, more preferably from 2:8 to 8:2, and still more preferably 3:7 to 7:3.

Further, as the component (S), a mixed solvent of at least one of PGMEA and EL with γ-butyrolactone is also preferable. The mixing ratio (former:latter) of such a mixed solvent is preferably from 70:30 to 95:5.

The amount of the organic solvent is not particularly limited, and is appropriately adjusted to a concentration which enables coating of a coating solution to a substrate, depending on the thickness of the coating film. In general, the organic solvent is used in an amount such that the solid content of the resist composition becomes within the range from 2 to 20% by weight, and preferably from 5 to 15% by weight.

Dissolving of the materials for a resist composition in the component (S) can be conducted by simply mixing and stirring each of the above components together using conventional methods, and where required, the composition may also be mixed and dispersed using a dispersion device such as a dissolver, a homogenizer, or a triple roll mill. Furthermore, following mixing, the composition may also be filtered using a mesh, or a membrane filter or the like.

The resist composition for immersion exposure containing the component (A) exhibits excellent lithography properties and other properties favorable for immersion exposure (both of hydrophobicity and hydrophilicity), which are properties required for a resist composition for immersion exposure. Therefore, the resist composition of the present invention can be preferably used for immersion exposure.

A resist film formed using the resist composition for immersion exposure containing the polymeric compound of the present invention contains the component (A), i.e., the fluorine-containing compound (A1) represented by general formula (a-i).

As described above, since the component (A) contains a fluorine atom, the hydrophobicity of a resist film formed using the resist composition for immersion exposure containing the component (A) is high, as compared to the case where the component (A) contains no fluorine atom.

As described above, a resist film formed using the resist composition for immersion exposure containing the component (A) exhibits high hydrophobicity during immersion exposure. Therefore, the resist film exhibits an excellent water tracking ability (tracking ability of water with respect to the movement of the lens) which is required when immersion exposure is conducted using a scanning-type immersion exposure apparatus as disclosed in Non-Patent Document 1.

Further, by using the resist composition for immersion exposure containing the component (A), elution of a substance from the resist film during immersion exposure can be suppressed.

As described above, immersion exposure is a method in which exposure (immersion exposure) is conducted in a state where the region between the lens and the resist layer formed on a wafer (which was conventionally filled with air or an inert gas such as nitrogen) is filled with a solvent (a immersion medium) that has a larger refractive index than the refractive index of air. In immersion exposure, when the resist film comes into contact with the immersion medium, elution of substances within the resist film (component (C), component (D), and the like) into the immersion medium occurs. This elution of a substance causes phenomenon such as degeneration of the resist film and change in the refractive index of the immersion medium, thereby adversely affecting the lithography properties.

The amount of the eluted substance is affected by the properties of the resist film surface (e.g., hydrophilicity, hydrophobicity and the like). Therefore, it is presumed that the amount of eluted substance can be reduced by enhancing the hydrophobicity of the resist film surface.

By virtue of a resist composition for immersion exposure containing the component (A), a resist film formed using the resist composition exhibits high hydrophobicity prior to conducting exposure and developing, as compared to a resist composition containing no component (A). Therefore, it is presumed that the resist composition for immersion exposure containing the component (A) can suppress substance elution during immersion exposure.

Since substance elution can be suppressed, by using the resist composition for immersion exposure containing the component (A), phenomena such as degeneration of the resist film and change in the refractive index of the immersion medium, which occur during immersion exposure, can be suppressed. Further, as variation in the refractive index of the immersion medium can be suppressed, a resist pattern having an excellent shape can be formed. Furthermore, the level of contamination of the lens within the exposure apparatus can be lowered. Therefore, there is no need for protection against these disadvantages, and hence, the present invention can contribute to simplifying the process and the exposure apparatus.

In addition, a resist film formed using the resist composition for immersion exposure containing the component (A) hardly swells by water. Therefore, a very fine resist pattern can be formed with a high precision.

Also, the resist composition for immersion exposure containing the component (A) exhibits excellent lithography properties with respect to sensitivity, resolution, etching resistance and the like, and is capable of forming a resist pattern without any practical problems when used as a resist for immersion exposure. For example, by using the resist composition for immersion exposure containing the component (A), a very fine resist pattern with a size of 120 nm or smaller can be formed.

The hydrophobicity of a resist film can be evaluated by measuring the contact angle thereof against water, for example, the static contact angle (the contact angle between the surface of a water droplet on the resist film in a horizontal state and the resist film surface), the dynamic contact angle (the contact angle at which a water droplet starts to slide when the resist film is inclined (sliding angle), the contact angle at the front-end point of the water droplet in the sliding direction (advancing angle) and the contact angle at the rear-end point of the water droplet in the sliding direction (receding angle)). For example, the higher the hydrophobicity of a resist film, the higher the static angle, advancing angle, and receding angle and the smaller the sliding angle.

As shown in FIG. 1, when a droplet 1 is placed on a plane 2 and the plane 2 is gradually inclined, the advancing angle is the angle $\theta_1$ formed between the lower end 1a of the droplet 1 and the plane 2 as the droplet 1 starts to move (slide) on the plane 2. Further, at this time (when the droplet 1 starts to move (slide) on the plane 2), the receding angle is the angle $\theta_2$ formed between the upper end 1b of the droplet 1 and the plane 2, and the sliding angle is the inclination angle $\theta_3$ of the plane 2.

In the present description, the advancing angle, receding angle and sliding angle are measured in the following manner.

First, a resist composition solution is spin-coated onto a silicon substrate, and then heated at a temperature of 110° C. for 60 seconds to form a resist film.

Subsequently, the contact angles can be measured using commercially available measurement apparatuses such as DROP MASTER-700 (product name; manufactured by Kyowa Interface Science Co. Ltd.), AUTO SLIDING ANGLE: SA-30 DM (product name; manufactured by Kyowa Interface Science Co. Ltd.), and AUTO DISPENSER: AD-31 (product name; manufactured by Kyowa Interface Science Co. Ltd.).

With respect to a resist film formed using the resist composition for immersion exposure containing the component (A), it is preferable that the receding angle as measured prior to conducting immersion exposure and developing is 50 degrees or more, more preferably 50 to 150 degrees, still more preferably 50 to 130 degrees, and most preferably 53 to 100 degrees. When the receding angle is at least as large as the lower limit of the above-mentioned range, the effect of suppressing the elution of a substance during immersion exposure is enhanced. The reason for this has not been elucidated yet, but it is presumed that one of the main reasons is related to the hydrophobicity of the resist film. More specifically, it is presumed that since an aqueous substance such as water is used as the immersion medium, higher hydrophobicity has an influence on the swift removal of the immersion medium from the surface of the resist film after the immersion exposure. On the other hand, when the receding angle is no more than the upper limit of the above-mentioned range, the lithography properties become satisfactory.

For the same reasons as described above, with respect to a resist film formed using the resist composition for immersion exposure containing the component (A), it is preferable that the static contact angle as measured prior to conducting immersion exposure and developing is 60 degrees or more, more preferably 63 to 97 degrees, and most preferably 65 to 97 degrees.

Further, with respect to a resist film formed using the resist composition for immersion exposure containing the component (A), it is preferable that the sliding angle as measured prior to conducting immersion exposure and developing is 36 degrees or lower, more preferably 10 to 36 degrees, still more preferably 7 to 30 degrees, and most preferably 14 to 27 degrees. When the receding angle is no more than the upper limit of the above-mentioned range, the effect of suppressing the elution of a substance during immersion exposure is enhanced. On the other hand, when the sliding angle is at least as large as the lower limit of the above-mentioned range, the lithography properties become satisfactory.

The level of the above-mentioned various angles (dynamic contact angle (advancing angle, receding angle and sliding angle) and static contact angle) can be adjusted by the formulation of the resist composition for immersion exposure, for example, the type and amount of the component (A), and the type of the component (B). For example, by increasing the amount of the component (A), the hydrophobicity of the obtained resist composition can be enhanced, and the advancing angle, receding angle and static contact angle becomes large, whereas the sliding angle becomes small.

Further, since the component (A) has an acid dissociable portion, the structure thereof is unchanged at unexposed portions, and when acid is generated from the component (C) upon exposure, the bond between the acid dissociable portion within X in the component (A) and the atom to which the acid dissociable portion is bonded is broken, and a group including "—C(=O)—O—R$^1$" is dissociated. As a result, the alkali solubility of the resist film is increased. Thus, when the resist composition for immersion exposure containing the component (A) is a positive resist composition, the component (A) exhibits the effect of suppressing dissolution in an alkali developing solution at unexposed portions of the resist film, and promoting dissolution at exposed portions, thereby enabling a high contrast of exposed portions/unexposed portions.

Furthermore, since the component (A) represented by general formula (a-i) has a carbonyloxy group (—C(=O)—O—) exhibiting a relatively high polarity, the component (A) exhibits improved compatibility with other components of the resist composition. Therefore, the resist composition for immersion exposure containing the component (A) is expected to exhibit improved post exposure stability.

As described above, the resist composition for immersion exposure containing the component (A) exhibits various properties required for a resist material for use in immersion exposure. Therefore, the resist composition can be preferably used for immersion exposure.

<<Method of Forming a Resist Pattern>>

The method of forming a resist pattern includes: applying a resist composition for immersion exposure containing the component (A) to a substrate to form a resist film on the substrate; subjecting the resist film to immersion exposure; and alkali developing the resist film to form a resist pattern.

A preferable example of the method of forming a resist pattern is described below.

Firstly, a resist composition for immersion exposure containing the polymeric compound of the present invention is applied onto a substrate using a spinner or the like, and a prebake (post applied bake (PAB)) is conducted to form a resist film.

The substrate is not specifically limited and a conventionally known substrate can be used. For example, substrates for electronic components, and such substrates having wiring patterns formed thereon can be used. Specific examples of the material of the substrate include metals such as silicon wafer, copper, chromium, iron and aluminum; and glass. Suitable materials for the wiring pattern include copper, aluminum, nickel, and gold.

Further, as the substrate, any one of the above-mentioned substrates provided with an inorganic and/or organic film on the surface thereof may be used. As the inorganic film, an inorganic antireflection film (inorganic BARC) can be used. As the organic film, an organic antireflection film (organic BARC) and an organic film such as a lower-layer organic film used in a multilayer resist method can be used.

Here, a "multilayer resist method" is method in which at least one layer of an organic film (lower-layer organic film) and at least one layer of a resist film (upper resist film) are provided on a substrate, and a resist pattern formed on the upper resist film is used as a mask to conduct patterning of the lower-layer organic film. This method is considered as being capable of forming a pattern with a high aspect ratio. More specifically, in the multilayer resist method, a desired thickness can be ensured by the lower-layer organic film, and as a result, the thickness of the resist film can be reduced, and an extremely fine pattern with a high aspect ratio can be formed.

The multilayer resist method is broadly classified into a method in which a double-layer structure consisting of an upper-layer resist film and a lower-layer organic film is formed (double-layer resist method), and a method in which a multilayer structure having at least three layers consisting of an upper-layer resist film, a lower-layer organic film and at least one intermediate layer (thin metal film or the like) provided between the upper-layer resist film and the lower-layer organic film (triple-layer resist method).

After formation of a resist film, an organic antireflection film may be provided on the resist film, thereby forming a triple layer laminate consisting of the substrate, the resist film and the antireflection film. The anti-reflection film provided on top of the resist film is preferably soluble in an alkali developing solution.

The steps up until this point can be conducted by using conventional techniques. The operating conditions and the like are preferably selected appropriately in accordance with the formulation and the characteristics of the resist composition for immersion exposure being used.

Subsequently, the obtained resist film is subjected to selective immersion exposure (liquid immersion lithography) through a desired mask pattern. At this time, the region between the resist film and the lens at the lowermost point of the exposure apparatus is pre-filled with a solvent (immersion medium) that has a larger refractive index than the refractive index of air, and the exposure (immersion exposure) is conducted in this state.

There are no particular limitations on the wavelength used for the exposure, and an ArF excimer laser, KrF excimer laser or $F_2$ excimer laser or the like can be used. The resist composition according to the present invention is effective for KrF or ArF excimer lasers, and is particularly effective for ArF excimer lasers.

The immersion medium preferably exhibits a refractive index larger than the refractive index of air but smaller than the refractive index of the resist film formed from the resist composition for immersion exposure containing the polymeric compound of the present invention. The refractive index of the immersion medium is not particularly limited as long at it satisfies the above-mentioned requirements.

Examples of this immersion medium which exhibits a refractive index that is larger than the refractive index of air but smaller than the refractive index of the resist film include water, fluorine-based inert liquids, silicon-based solvents and hydrocarbon-based solvents.

Specific examples of the fluorine-based inert liquids include liquids containing a fluorine-based compound such as $C_3HCl_2F_5$, $C_4F_9OCH_3$, $C_4F_9OC_2H_5$ or $C_5H_3F_7$ as the main component, which have a boiling point within a range from 70 to 180° C. and preferably from 80 to 160° C. A fluorine-based inert liquid having a boiling point within the above-mentioned range is advantageous in that the removal of the immersion medium after the exposure can be conducted by a simple method.

As a fluorine-based inert liquid, a perfluoroalkyl compound in which all of the hydrogen atoms of the alkyl group are substituted with fluorine atoms is particularly desirable. Examples of these perfluoroalkyl compounds include perfluoroalkylether compounds and perfluoroalkylamine compounds.

Specifically, one example of a suitable perfluoroalkylether compound is perfluoro(2-butyl-tetrahydrofuran) (boiling point 102° C.), and an example of a suitable perfluoroalkylamine compound is perfluorotributylamine (boiling point 174° C.).

A resist composition for immersion containing the polymeric compound of the present invention is particularly resistant to any adverse effects caused by water, and because the resulting lithography properties such as sensitivity and shape of the resist pattern are excellent, water is preferably used as the immersion medium which exhibits a refractive index that is larger than the refractive index of air. Furthermore, water is also preferred in terms of cost, safety, environmental friendliness, and versatility.

Subsequently, following completion of the immersion exposure step, post exposure baking (PEB) is conducted, followed by a developing treatment using an alkali developing solution containing an alkali aqueous solution. Thereafter, water rinse is preferably conducted with pure water. This water rinse can be conducted by dripping or spraying water onto the surface of the substrate while rotating the substrate, and washes away the developing solution and those portions of the resist composition for immersion exposure that have been dissolved by the developing solution. Further, by drying, a resist pattern is obtained in which the resist film (coating of the resist composition for immersion exposure) has been patterned into a shape corresponding to the mask pattern.

EXAMPLES

As follows is a description of examples of the present invention, although the scope of the present invention is in no way limited by these examples.

Example 1

Synthesis of Compound (1-a)

[Chemical Formula 52]

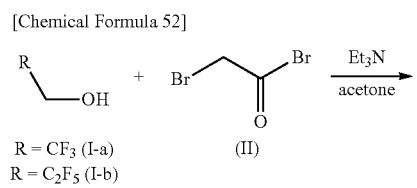

R = CF$_3$ (I-a)
R = C$_2$F$_5$ (I-b)

(II)

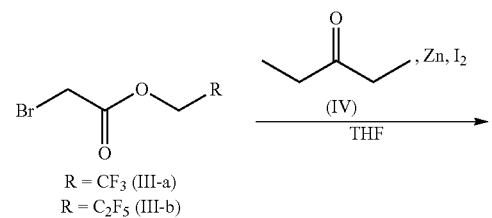

R = CF$_3$ (III-a)
R = C$_2$F$_5$ (III-b)

(IV)

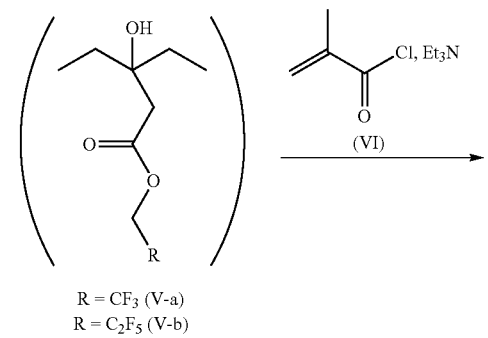

R = CF$_3$ (V-a)
R = C$_2$F$_5$ (V-b)

(VI)

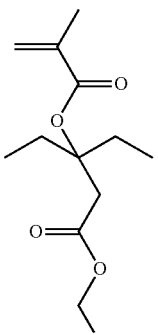

R = CF₃ (1-a)
R = C₂F₅ (1-b)

First step: synthesis of 2,2,2-trifluoroethyl bromoacetate (compound (III-a))

400 g of acetone, 100 g of 2,2,2-trifluoroethanol (compound (I-a)) and 121.3 g of triethylamine were added to a four-necked flask equipped with a stirrer, a nitrogen-feeding pipe, a dropping funnel and a thermometer. The four-necked flask was purged with nitrogen, and cooled to 0° C. Then, 86.1 g of bromoacetylbromide (compound (II)) was dropwise added thereto at 0 to 5° C. over 3 hours, followed by stirring at 0° C. for 2 hours. Thereafter, 300 g of saturated sodium hydrogencarbonate aqueous solution was added thereto to stop the reaction, and extraction was conducted using ethyl acetate. The obtained organic phase was washed with water, followed by drying with anhydrous magnesium sulfate and concentration under reduced pressure. The resulting concentrate was purified by distillation under reduced pressure, thereby obtaining 72.4 g of 2,2,2-trifluoroethyl bromoacetate (compound (III-a)).

Second step and third step: synthesis of 1,1-diethyl-2-(2,2,2-trifluoroethoxycarbonyl)ethyl methacrylate (compound (1-a))

125.6 g of tetrahydrofuran, 243 g of 3-pentanone (compound (IV)) and 23.6 g of a zinc powder were added to a four-necked flask equipped with a stirrer, a nitrogen-feeding pipe, a dropping funnel and a thermometer. Then, the flask was purged with nitrogen, and iodine was added thereto in a catalyst amount, and 6.2 g of the compound (III-a) obtained in the first step was further added at 45° C. Thereafter, 55.3 g of the compound (III-a) obtained in the first step was dropwise added at 55° C. over 30 minutes, followed by stirring for 90 minutes.

Subsequently, the reaction solution was cooled to room temperature, and 31.7 g of triethylamine was added thereto. Then, 32.8 g of methacrylic acid chloride (compound (VI)) was dropwise added thereto at 20° C. for 40 minutes, followed by stirring for 2 hours. Thereafter, 250 g of a 10% sodium hydrogencarbonate aqueous solution was added to stop the reaction, and extraction was conducted with ethyl acetate. The obtained organic phase was washed with a 10% sodium hydrogencarbonate aqueous solution and water in this order, followed by drying with anhydrous magnesium sulfate and concentration under reduced pressure. The resulting concentrate was purified by distillation under reduced pressure, thereby obtaining 57.5 g of 1,1-diethyl-2-(2,2,2-trifluoroethoxycarbonyl)ethyl methacrylate (compound (1-a)) as a fluorine-containing compound (A1).

The obtained compound (1-a) was analyzed by $^1$H-NMR. The results are shown below.

$^1$H-NMR (CDCl$_3$) δ: 0.92 (tr, 6H, —CH$_3$), 1.90 (s, 3H, =C—CH$_3$), 1.86-2.08 (m, 4H, —C—CH$_2$—), 3.09 (s, 2H, —CH$_2$—C(=O)—), 4.49 (q, 2H, CF$_3$—CH$_2$—), 5.51 (m, 1H, C=CH$_2$), 6.03 (s, 1H, C=CH$_2$)

From the results, it was confirmed that the compound (1-a) had a structure as shown above.

Example 2

Synthesis of Compound (1-b)

First step: synthesis of 2,2,3,3,3-pentafluoropropyl bromoacetate (compound (III-b))

400 g of acetone, 100 g of 2,2,3,3,3-pentafluoropropanol (compound (I-b)) and 121.3 g of triethylamine were added to a four-necked flask equipped with a stirrer, a nitrogen-feeding pipe, a dropping funnel and a thermometer, and synthesis was conducted in the same manner as in the synthesis of compound (III-a), thereby obtaining 49.6 g of 2,2,3,3,3-pentafluoropropyl bromoacetate (compound (III-b)).

Second step and third step: synthesis of 1,1-diethyl-2-(2,2,3,3,3-pentafluoropropoxycarbonyl)ethyl methacrylate (compound (1-b))

224.7 g of tetrahydrofuran, 24.7 g of 3-pentanone (compound (IV)) and 23.6 g of a zinc powder were added to a four-necked flask equipped with a stirrer, a nitrogen-feeding pipe, a dropping funnel and a thermometer. Then, the flask was purged with nitrogen, and iodine was added thereto in a catalyst amount, and 7.6 g of the compound (III-b) obtained in the first step was further added at 45° C. Thereafter, 68.3 g of the compound (III-b) obtained in the first step was dropwise added at 55° C. over 30 minutes, followed by stirring for 90 minutes.

Subsequently, the reaction solution was cooled to room temperature, and 42.5 g of triethylamine was added thereto. Then, 41.0 g of methacrylic acid chloride (compound (VI)) was dropwise added thereto at 20° C. for 40 minutes, and the same procedure as in the synthesis of the compound (1-a) was performed, thereby obtaining 51.1 g of 1,1-diethyl-2-(2,2,3,3-pentafluoropropoxycarbonyl)ethyl methacrylate (compound (1-b)) as a fluorine-containing compound (A1).

The obtained compound (1-b) was analyzed by $^1$H-NMR. The results are shown below.

$^1$H-NMR (CDCl$_3$) δ: 0.90 (tr, 6H, —CH$_3$), 1.90 (s, 3H, =C—CH$_3$), 1.86-2.08 (m, 4H, —C—CH$_2$—), 3.08 (s, 2H, —CH$_2$—C(=O)—), 4.53 (q, 2H, CF$_3$—CH$_2$—), 5.52 (m, 1H, C=CH$_2$), 6.03 (s, 1H, C=CH$_2$)

Example 3

Synthesis of Polymeric Compound (2-a)

[Chemical Formula 53]

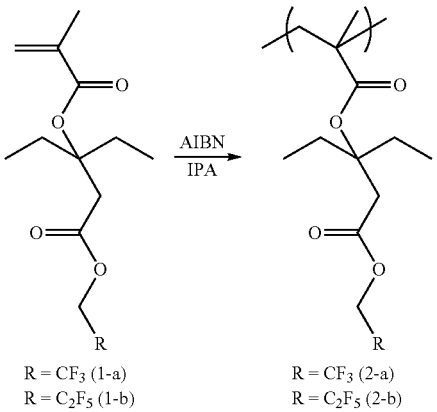

R = CF₃ (1-a)
R = C₂F₅ (1-b)

R = CF₃ (2-a)
R = C₂F₅ (2-b)

3.84 g of isopropylalcohol was added to a four-necked flask equipped with a nitrogen-feeding pipe, a reflux condenser, a dropping funnel and a thermometer, and the flask was purged with nitrogen. Then, the flask was heated to 80° C., and a solution obtained by dissolving 15.0 g of the compound (1-a) and 0.582 g of azobisisobutyronitrile in 10.0 g of isopropylalcohol was dropwise added over 2 hours. Thereafter, stirring was conducted for 4 hours while maintaining the temperature at 80° C., and then the resultant was cooled to room temperature. The obtained polymerization reaction solution was dropwise added to an excess amount of an isopropylalcohol/water mixed solution to obtain a precipitate. The obtained precipitate was dissolved in tetrahydrofuran, and the resultant was dropwise added to an excess amount of an isopropylalcohol/water mixed solution. The precipitated resin was separated by filtration, followed by washing and drying, thereby obtaining, as a polymeric compound (A2), 7.1 g of a polymeric compound (2-a) in the form of a white solid. The obtained polymeric compound (2-a) had a weight average molecular weight (Mw) of 7,300 and a molecular weight distribution (Mw/Mn) of 1.4 (polystyrene equivalent value determined by gel permeation chromatography (GPC)).

Example 4

Synthesis of Polymeric Compound (2-b)

4.16 g of isopropylalcohol was added to a four-necked flask equipped with a nitrogen-feeding pipe, a reflux condenser, a dropping funnel and a thermometer, and the flask was purged with nitrogen. Then, the flask was heated to 80° C., and a solution obtained by dissolving 18.0 g of the compound (1-b) and 0.682 g of azobisisobutyronitrile in 12.0 g of isopropylalcohol was dropwise added over 2 hours. Thereafter, stirring was conducted for 4 hours while maintaining the temperature at 80° C., and then the resultant was cooled to room temperature. The obtained polymerization reaction solution was dropwise added to an excess amount of an isopropylalcohol/water mixed solution to obtain a precipitate. The obtained precipitate was dissolved in tetrahydrofuran, and the resultant was dropwise added to an excess amount of an isopropylalcohol/water mixed solution. The precipitated resin was separated by filtration, followed by washing and drying, thereby obtaining, as a polymeric compound (A2), 7.1 g of a polymeric compound (2-b) in the form of a white solid. The obtained polymeric compound (2-b) had a weight average molecular weight (Mw) of 7,300 and a molecular weight distribution (Mw/Mn) of 1.4 (polystyrene equivalent value determined by gel permeation chromatography (GPC)).

Production of Resist Composition

Test Examples 1 to 3

The components shown in Table 1 were mixed together and dissolved in the amounts shown in Table 1 to obtain positive resist compositions.

TABLE 1

| | (A) | (B) | (C) | (D) | (E) | (S) | |
|---|---|---|---|---|---|---|---|
| Test Example 1 | (A)-1 [1.0] | (B)-1 [100] | (C)-1 [8.0] | (D)-1 [0.12] | (E)-1 [1.32] | (S)-1 [10] | (S)-2 [2500] |
| Test Example 2 | (A)-1 [2.0] | (B)-1 [100] | (C)-1 [8.0] | (D)-1 [0.12] | (E)-1 [1.32] | (S)-1 [10] | (S)-2 [2500] |
| Test Example 3 | — | (B)-1 [100] | (C)-1 [8.0] | (D)-1 [0.12] | (E)-1 [1.32] | (S)-1 [10] | (S)-2 [2500] |

In Table 1, the reference characters indicate the following. Further, the values in brackets [ ] indicate the amount (in terms of parts by weight) of the component added.

(A)-1: the aforementioned polymeric compound (2-a)
(B)-1: a copolymer represented by chemical formula (B)-1 shown below, having an Mw of 7,000 and Mw/Mn of 1.8
(C)-1: (4-methylphenyl)diphenylsulfonium nonafluoro-n-butanesulfonate
(D)-1: tri-n-pentylamine
(E)-1: salicylic acid
(S)-1: γ-butyrolactone
(S)-2: a mixed solvent of PGMEA/EL=8/2 (weight ratio)

[Chemical Formula 54]

(B)-1

(B)-1 was produced by copolymerizing the monomers for obtaining the corresponding structural units by a conventional dropwise polymerization method. In chemical formula (B)-1, the subscript numerals represent the proportion (mol %) of the respective structural units. This compositional ratio was determined by $^{13}$C-NMR. Further, the Mw and the Mw/Mn were determined by gel permeation chromatography (GPC) in terms of the polystyrene equivalent value.

Using the obtained resist compositions, the static contact angle and the dynamic contact angle (sliding angle and receding angle) of the resist film surface prior to exposure were measured as follows, to thereby evaluate the hydrophobicity of the resist film.

<Evaluation of Hydrophobicity>

Each of the resist compositions of Test Examples 1 to 3 was applied to an 8-inch silicon wafer using a spinner, and was then prebaked (PAB) on a hotplate at 110° C. for 60 seconds and dried, thereby forming a resist film having a film thickness of 120 nm.

Subsequently, 50 μl of water was dropped onto the surface of the resist film (prior to exposure), and the contact angles were measured using DROP MASTER-700 (manufactured by Kyowa Interface Science Co. Ltd.). The results are shown in Table 2.

<Evaluation of Eluted Substance>

Using the resist compositions of Test Examples 2 and 3, a resist film having a film thickness of 120 nm was formed in the same manner as described above. Then, using VRC310S (product name; manufactured by S.E.S CO., LTD.), one droplet of pure water (50 μl) was moved from the center of the wafer in a circular manner at room temperature at a constant linear velocity (total area of the resist film that came in contact with the droplet: 221.56 cm$^2$).

Thereafter, the droplet was collected, and analyzed by an analyzing apparatus Agilent-HP1100 LC-MSD (product name; manufactured by Agilent Technologies), and the amount of component (C) elution ($\times 10^{-12}$ mol/cm$^2$·s) was determined. The results are shown in Table 3.

TABLE 2

|  | Static contact angle (°) | Sliding angle (°) | Receding angle (°) |
|---|---|---|---|
| Test Example 1 | 86.4 | 19 | 66.1 |
| Test Example 2 | 90.1 | 14 | 75 |
| Test Example 3 | 67.5 | 20.0 | 56.3 |

TABLE 3

|  | Amount of elution ($\times 10^{-12}$ mol/cm$^2$ · sec) |
|---|---|
| Test Example 2 | 0.21 |
| Test Example 3 | 55.85 |

From the results shown above, it was confirmed that the resist film obtained using the resist compositions of Test Examples 1 and 2 exhibited a large static contact angle, a large receding angle and a small sliding angle prior to exposure, as compared to the resist film obtained using the resist composition of Test Example 3. Thus, it was confirmed that a highly hydrophobic resist film can be obtained by addition of such a polymeric compound (2-a).

With respect to the resist film obtained using the resist composition of Test Example 2, the amount of the component (C) eluted to the immersion medium (i.e., water) prior to exposure was small, and hence, it was confirmed that a resist film in which substance elution is significantly suppressed can be obtained by addition of such a polymeric compound (2-a).

<Evaluation of Lithography Properties>

An organic anti-reflection film composition (product name: ARC29A, manufactured by Brewer Science Ltd.) was applied to an 12-inch silicon wafer using a spinner, and the composition was then baked at 205° C. for 60 seconds, thereby forming an organic anti-reflection film having a film thickness of 89 nm. Then, each of the resist compositions shown in Table 1 was applied to the anti-reflection film using a spinner, and was then prebaked (PAB) on a hotplate at 110° C. for 60 seconds and dried, thereby forming a resist film having a film thickness of 100 nm.

Subsequently, the resist film was selectively irradiated with an ArF excimer laser (193 nm) through a mask pattern, using an ArF immersion exposure apparatus NSR-S609B (manufactured by Nikon Corporation, NA (numerical aperture)= 1.07, σ0.97). Thereafter, a post exposure bake (PEB) treatment was conducted at 110° C. for 60 seconds, followed by development for 30 seconds at 23° C. in a 2.38% by weight aqueous solution of tetramethylammonium hydroxide (TMAH). Then, the resist was washed for 30 seconds with pure water, followed by drying by shaking, thereby forming a resist pattern.

As a result, in each of the examples, a line and space pattern with a line width of 55 nm and a pitch of 110 nm was formed on the resist film.

From the results shown above, it was confirmed that the resist compositions of Test Examples 1 and 2 were preferable for immersion exposure.

Production of Resist Composition

Test Examples 4 and 5

The components shown in Table 4 were mixed together and dissolved in the amounts shown in Table 4 to obtain positive resist compositions.

TABLE 4

|  | (A) | (B) | (C) | (D) | (E) | (S) | |
|---|---|---|---|---|---|---|---|
| Test Example 4 | (A)-2 [1.9] | (B)-1 [100] | (C)-1 [8.0] | (D)-1 [0.12] | (E)-1 [1.32] | (S)-1 [10] | (S)-2 [2500] |
| Test Example 5 | (A)-3 [1.0] | (B)-1 [100] | (C)-1 [8.0] | (D)-1 [0.12] | (E)-1 [1.32] | (S)-1 [10] | (S)-2 [2500] |

In Table 4, (A)-2 denotes the aforementioned polymeric compound (2-b), and (A)-3 denotes a polymeric compound represented by formula (A)-3 shown below (Mw: 8,200, dispersity: 1.5). Further, the values in brackets [ ] indicate the amount (in terms of parts by weight) of the component added. In Table 4, (B)-1, (C)-1, (D)-1, (E)-1, (S)-1 and (S)-2 are the same as defined in Table 1.

[Chemical Formula 55]

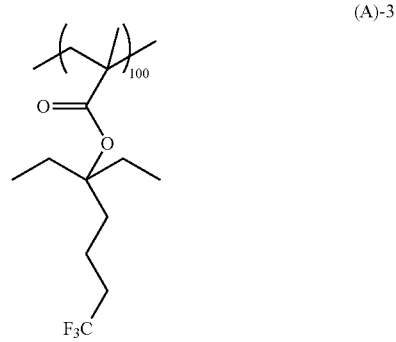

(A)-3

Using the resist composition obtained in Test Example 4, "evaluation of hydrophobicity" and "evaluation of eluted substance" were performed in the same manner as in Test Example 1. The results are shown in Tables 5 and 6.

TABLE 5

|  | Static contact angle (°) | Sliding angle (°) | Receding angle (°) |
|---|---|---|---|
| Test Example 4 | 94.8 | 19.0 | 66.1 |

TABLE 6

|  | Amount of elution ($\times 10^{-12}$ mol/cm$^2$ · sec) |
|---|---|
| Test Example 4 | 2.24 |

From the results shown above, it was confirmed that the resist film obtained using the resist composition of Test Example 4, like the resist film obtained using the resist compositions of Test Examples 1 and 2, exhibited a large static contact angle, a large receding angle and a small sliding angle prior to exposure, as compared to the resist film obtained using the resist composition of Test Example 3. Further, it was confirmed that substance elution could be significantly suppressed.

<Evaluation of Defects>

An organic anti-reflection film composition (product name: ARC29A, manufactured by Brewer Science Ltd.) was applied to a 12-inch silicon wafer using a spinner, and the composition was then baked at 205° C. for 60 seconds, thereby forming an organic anti-reflection film having a film thickness of 89 nm. Then, each of the resist compositions shown in Table 4 was applied to the anti-reflection film using a spinner, and was then prebaked (PAB) on a hotplate at 110° C. for 60 seconds and dried, thereby forming a resist film having a film thickness of 100 nm.

Subsequently, the resist film was selectively irradiated with an ArF excimer laser (193 nm) through a mask pattern, using an ArF immersion exposure apparatus NSR-S609B (manufactured by Nikon Corporation, NA (numerical aperture)= 1.07, σ0.97). Thereafter, a post exposure bake (PEB) treatment was conducted at 110° C. for 60 seconds, followed by development for 30 seconds at 23° C. in a 2.38% by weight aqueous solution of tetramethylammonium hydroxide (TMAH). Then, the resist was washed for 30 seconds with pure water, followed by drying by shaking, thereby forming a resist pattern.

As a result, in each of the examples, a line and space pattern with a line width of 55 nm and a pitch of 110 nm was formed on the resist film.

The obtained resist pattern was observed at an exposed portion and an unexposed portion using a surface defect observation apparatus (product name: KLA; manufactured by KLA-TENCOR CORPORATION), and the number of defects was determined. The results are shown in Table 7 in terms of percentage based on the number of defects observed with respect to the resist film of Test Example 5.

TABLE 7

|  | Percentage of defects (%) | |
|---|---|---|
|  | Exposed portion | Unexposed portion |
| Test Example 4 | 63 | 5 |
| Test Example 5 | 100 | 100 |

From the results shown in Table 7, it was confirmed that the resist composition of Test Example 4 was excellent in reducing defects at both the exposed portion and the unexposed portion, as compared to the resist composition of Test Example 5. In particular, defects were significantly reduced at the unexposed portion.

From the results shown above, it was confirmed that the resist composition of Test Example 4 was preferable for immersion exposure.

Example 5

Synthesis of Compound (3-a)

[Chemical Formula 56]

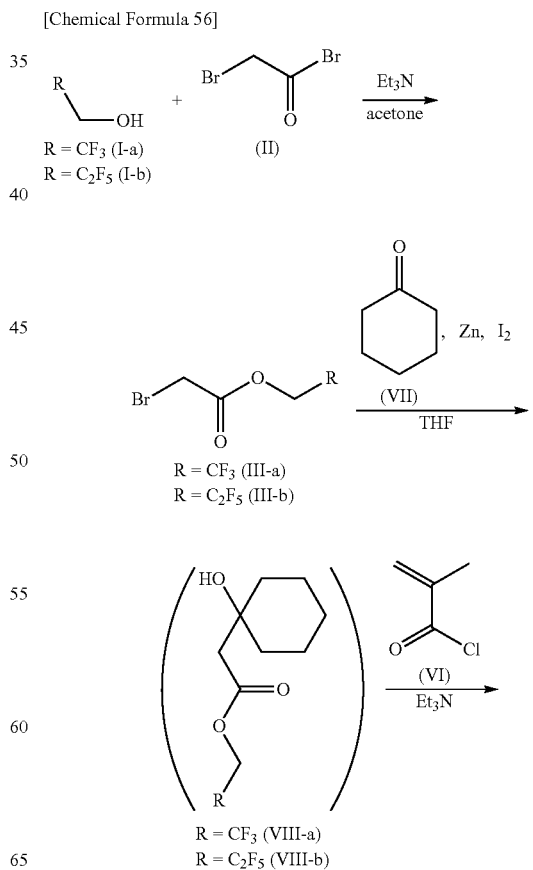

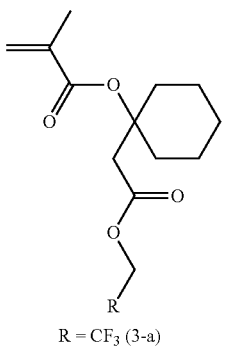

R = CF$_3$ (3-a)
R = C$_2$F$_5$ (3-b)

296.0 g of tetrahydrofuran, 48.9 g of cyclohexanone (compound (VII)) and 35.0 g of a zinc powder were added to a four-necked flask equipped with a stirrer, a nitrogen-feeding pipe, a dropping funnel and a thermometer. Then, the flask was purged with nitrogen, and iodine was added thereto in a catalyst amount, and 10.0 g of the compound (III-a) obtained in Example 1 was further added at 55° C. Thereafter, 90.0 g of the compound (III-a) was added at 60° C. over 30 minutes, followed by stirring for 120 minutes.

Subsequently, the reaction solution was cooled to room temperature, and 59.5 g of triethylamine was added thereto. Then, 56.8 g of methacrylic acid chloride (compound (VI)) was dropwise added thereto at 20° C. for 40 minutes, and the same procedure as in the synthesis of the compound (1-a) was performed, thereby obtaining 56.6 g of 1-cyclohexyl-2-(2,2,2-trifluoroethoxycarbonyl)ethyl methacrylate (compound (3-a)) as a fluorine-containing compound (A1).

The obtained compound (3-a) was analyzed by $^1$H-NMR. The results are shown below.

$^1$H-NMR (CDCl$_3$) δ: 1.20-1.38 (m, 1H, c-C$_6$H$_{10}$), 1.48-1.71 (m, 7H, c-C$_6$H$_{10}$), 1.93 (s, 3H, =C—CH$_3$), 2.30-2.38 (m, 2H, c-C$_6$—H$_{10}$), 3.12 (s, 2H, —CH$_2$—C(=O)—), 4.44 (q, 2H, CF$_3$—CH$_2$—), 5.56 (m, 1H, C=CH$_2$), 6.09 (s, 1H, C=CH$_2$)

Example 6

Synthesis of Compound (3-b)

444.0 g of tetrahydrofuran, 70.6 g of cyclohexanone (compound (VII)) and 51.0 g of a zinc powder were added to a four-necked flask equipped with a stirrer, a nitrogen-feeding pipe, a dropping funnel and a thermometer. Then, the flask was purged with nitrogen, and iodine was added thereto in a catalyst amount, and 15.0 g of the compound (III-b) obtained in Example 2 was further added at 55° C. Thereafter, 135.0 g of the compound (III-b) was added at 60° C. over 30 minutes, followed by stirring for 90 minutes.

Subsequently, the reaction solution was cooled to room temperature, and 72.8 g of triethylamine was added thereto. Then, 69.4 g of methacrylic acid chloride (compound (VI)) was dropwise added thereto at 20° C. for 40 minutes, and the same procedure as in the synthesis of the compound (1-a) was performed, thereby obtaining 38.1 g of 1-cyclohexane-2-(2,2,3,3,3-pentafluoropropoxycarbonyl)ethyl methacrylate (compound (3-b)) as a fluorine-containing compound (A1).

The obtained compound (3-b) was analyzed by $^1$H-NMR. The results are shown below.

$^1$H-NMR (CDCl$_3$) δ: 1.21-1.38 (m, 1H, c-C$_6$H$_{10}$), 1.48-1.72 (m, 7H, c-C$_6$H$_{10}$), 1.94 (s, 3H, =C—CH$_3$), 2.28-2.39 (m, 2H, c-C$_6$—H$_{10}$), 3.13 (s, 2H, —CH$_2$C(=O)—), 4.51 (t, 2H, —CF$_2$—CH$_2$—), 5.55 (m, 1H, C=CH$_2$), 6.07 (s, 1H, C=CH$_2$)

Example 7

Synthesis of Polymeric Compound (4-a)

[Chemical Formula 57]

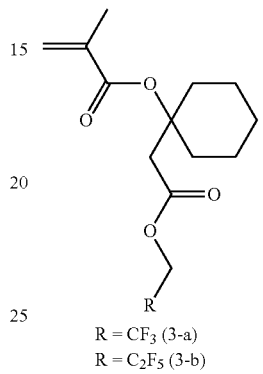

R = CF$_3$ (3-a)
R = C$_2$F$_5$ (3-b)

Dimethyl-2,2'-azobis(2-methylpropionate)
─────────────→
IPA

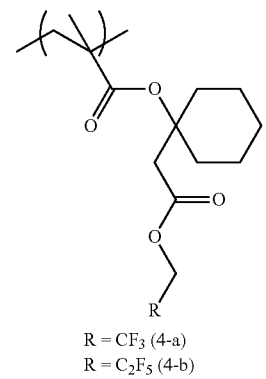

R = CF$_3$ (4-a)
R = C$_2$F$_5$ (4-b)

3.84 g of isopropylalcohol was added to a four-necked flask equipped with a nitrogen-feeding pipe, a reflux condenser, a dropping funnel and a thermometer, and the flask was purged with nitrogen. Then, the flask was heated to 80° C., and a solution obtained by dissolving 15.0 g of the compound (3-a) and 0.960 g of dimethyl-2,2'-azobis(2-methylpropionate) in 10.0 g of isopropylalcohol was dropwise added over 2 hours. Thereafter, stirring was conducted for 4 hours while maintaining the temperature at 80° C., and then the resultant was cooled to room temperature. The obtained polymerization reaction solution was dropwise added to an excess amount of an isopropylalcohol/water mixed solution to obtain a precipitate. The obtained precipitate was dissolved in tetrahydrofuran, and the resultant was dropwise added to an excess amount of an isopropylalcohol/water mixed solution. The precipitated resin was separated by filtration, followed by washing and drying, thereby obtaining, as a polymeric compound (A2), 8.9 g of a polymeric compound (4-a) in the form of a white solid. The obtained polymeric compound (4-a) had a weight average molecular weight (Mw) of 7,800 and a molecular weight distribution (Mw/Mn) of 1.5 (polystyrene equivalent values determined by gel permeation chromatography (GPC)).

Example 8

Synthesis of Polymeric Compound (4-b)

3.84 g of isopropylalcohol was added to a four-necked flask equipped with a nitrogen-feeding pipe, a reflux condenser, a dropping funnel and a thermometer, and the flask was purged with nitrogen. Then, the flask was heated to 80° C., and a solution obtained by dissolving 15.0 g of the compound (3-b) and 0.916 g of dimethyl-2,2'-azobis(2-methylpropionate) in 10.0 g of isopropylalcohol was dropwise added over 2 hours. Thereafter, stirring was conducted for 4 hours while maintaining the temperature at 80° C., and then the resultant was cooled to room temperature. The obtained polymerization reaction solution was dropwise added to an excess amount of an isopropylalcohol/water mixed solution to obtain a precipitate. The obtained precipitate was dissolved in tetrahydrofuran, and the resultant was dropwise added to an excess amount of an isopropylalcohol/water mixed solution. The precipitated resin was separated by filtration, followed by washing and drying, thereby obtaining, as a polymeric compound (A2), 9.6 g of a polymeric compound (4-b) in the form of a white solid. The obtained polymeric compound (4-b) had a weight average molecular weight (Mw) of 8,000 and a molecular weight distribution (Mw/Mn) of 1.5 (polystyrene equivalent values determined by gel permeation chromatography (GPC)).

Production of Resist Composition

Test Examples 6 to 8

The components shown in Table 8 were mixed together and dissolved in the amounts shown in Table 8 to obtain positive resist compositions.

TABLE 8

| | (A) | (B) | (C) | (D) | (E) | (S) |
|---|---|---|---|---|---|---|
| Test Example 6 | (A)-4 [2.0] | (A)-1 [100] | (C)-1 [8.0] | (D)-1 [0.12] | (E)-1 [1.32] | (S)-3 [2500] |
| Test Example 7 | (A)-5 [2.0] | (B)-1 [100] | (C)-1 [8.0] | (D)-1 [0.12] | (E)-1 [1.32] | (S)-3 [2500] |
| Test Example 8 | (A)-3 [2.0] | (B)-1 [100] | (C)-1 [8.0] | (D)-1 [0.12] | (E)-1 [1.32] | (S)-3 [2500] |

In Table 8, the reference characters indicate the following. Further, the values in brackets [ ] indicate the amount (in terms of parts by weight) of the component added. (A)-4 denotes the aforementioned polymeric compound (4-a), and (A)-5 denotes the aforementioned polymeric compound (4-b). (B)-1, (C)-1, (D)-1, and (E)-1 are the same as defined in Table 1. (A)-3 is the same as defined in Table 4.

(S)-3 denotes a mixed solvent of PGMEA/PGME=6/4 (weight ratio).

Using the obtained resist compositions, the static contact angle and the dynamic contact angle (sliding angle and receding angle) of the resist film surface prior to exposure were measured as follows, to thereby evaluate the hydrophobicity of the resist film.

<Evaluation of Hydrophobicity>

Each of the resist compositions of Test Examples 6 and 7 was applied to an 8-inch silicon wafer using a spinner, and was then prebaked (PAB) on a hotplate at 110° C. for 60 seconds and dried, thereby forming a resist film having a film thickness of 120 nm.

Subsequently, 50 µl of water was dropped onto the surface of the resist film (prior to exposure), and the contact angles were measured using DROP MASTER-700 (manufactured by Kyowa Interface Science Co. Ltd.). The results are shown in Table 9.

<Evaluation of Eluted Substance>

Using the resist compositions of Test Examples 6 and 7, a resist film having a film thickness of 120 nm was formed in the same manner as described above. Then, using VRC310S (product name; manufactured by S.E.S CO., LTD.), one droplet of pure water (50 µl) was moved from the center of the wafer in a circular manner at room temperature at a constant linear velocity (total area of the resist film that came in contact with the droplet: 221.56 cm$^2$).

Thereafter, the droplet was collected, and analyzed by an analyzing apparatus Agilent-HP 1100 LC-MSD (product name; manufactured by Agilent Technologies), and the amount of component (C) elution ($\times 10^{-12}$ mol/cm$^2$·s) was determined. The results are shown in Table 10.

TABLE 9

| | Static contact angle (°) | Sliding angle (°) | Receding angle (°) |
|---|---|---|---|
| Test Example 6 | 86 | 15 | 74.6 |
| Test Example 7 | 95.3 | 20.5 | 75.8 |

TABLE 10

| | Amount of elution ($\times 10^{-12}$ mol/cm$^2$ · sec) |
|---|---|
| Test Example 6 | 2.35 |
| Test Example 7 | 3.21 |

<Evaluation of Defects>

An organic anti-reflection film composition (product name: ARC29A, manufactured by Brewer Science Ltd.) was applied to a 12-inch silicon wafer using a spinner, and the composition was then baked at 205° C. for 60 seconds, thereby forming an organic anti-reflection film having a film thickness of 89 nm. Then, each of the resist compositions shown in Table 8 was applied to the anti-reflection film using a spinner, and was then prebaked (PAB) on a hotplate at 110° C. for 60 seconds and dried, thereby forming a resist film having a film thickness of 100 nm.

Subsequently, the resist film was selectively irradiated with an ArF excimer laser (193 nm) through a mask pattern, using an ArF immersion exposure apparatus NSR-S609B (manufactured by Nikon Corporation, NA (numerical aperture)= 1.07, σ0.97). Thereafter, a post exposure bake (PEB) treatment was conducted at 110° C. for 60 seconds, followed by development for 30 seconds at 23° C. in a 2.38% by weight aqueous solution of tetramethylammonium hydroxide (TMAH). Then, the resist was washed for 30 seconds with pure water, followed by drying by shaking, thereby forming a resist pattern.

As a result, in each of the examples, a line and space pattern with a line width of 55 nm and a pitch of 110 nm was formed on the resist film.

The obtained resist pattern was observed at an exposed portion and an unexposed portion using a surface defect observation apparatus (product name: KLA; manufactured by KLA-TENCOR CORPORATION), and the number of defects was determined. The results are shown in Table 11 in terms of percentage based on the number of defects observed with respect to the resist film of Test Example 8.

TABLE 11

| | Percentage of defects (%) | |
|---|---|---|
| | Exposed portion | Unexposed portion |
| Test Example 6 | 70 | 20 |
| Test Example 7 | 79 | 29 |
| Test Example 8 | 100 | 100 |

From the results shown in Table 11, it was confirmed that the resist compositions of Test Examples 6 and 7 were excellent in reducing defects at both the exposed portion and the unexposed portion, as compared to the resist composition of Test Example 8. In particular, defects were significantly reduced at the unexposed portion.

While preferred embodiments of the invention have been described and illustrated above, it should be understood that these are exemplary of the invention and are not to be considered as limiting. Additions, omissions, substitutions, and other modifications can be made without departing from the spirit or scope of the present invention. Accordingly, the invention is not to be considered as being limited by the foregoing description, and is only limited by the scope of the appended claims.

What is claimed is:

1. A fluorine-containing compound represented by general formula (a-i) shown below:

[Chemical Formula 1]

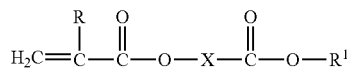

(a-i)

wherein R represents a hydrogen atom, a lower alkyl group or a halogenated lower alkyl group; X represents a divalent organic group represented by general formula (x-1) shown below; and R$^1$ represents an organic group having a fluorine atom,

[Chemical Formula 2]

(x-1)

wherein each of R$^{21}$ and R$^{22}$ independently represents an alkyl group which may be mutually bonded to form a ring; and X$^1$ represents an alkylene group or a divalent aliphatic cyclic group.

2. A polymeric compound comprising a structural unit derived from the fluorine-containing compound of claim 1.

3. A polymeric compound comprising a structural unit represented by general formula (a-ii) shown below:

[Chemical Formula 3]

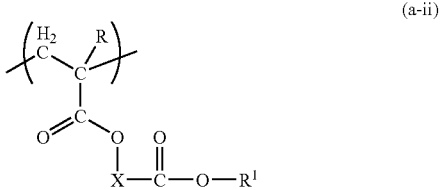

(a-ii)

wherein R represents a hydrogen atom, a lower alkyl group or a halogenated lower alkyl group; X represents a divalent organic group represented by general formula (x-1) shown below; and R$^1$ represents an organic group having a fluorine atom,

[Chemical Formula 4]

(x-1)

wherein each of R$^{21}$ and R$^{22}$ independently represents an alkyl group which may be mutually bonded to form a ring; and X$^1$ represents an alkylene group or a divalent aliphatic cyclic group.

* * * * *